(12) United States Patent
Schneider et al.

(10) Patent No.: US 8,778,940 B2
(45) Date of Patent: *Jul. 15, 2014

(54) CHEMICAL INDUCERS OF NEUROGENESIS

(75) Inventors: Jay Schneider, Coppell, TX (US);
Jenny Hsieh, Irving, TX (US); Douglas Frantz, Flower Mound, TX (US);
Steven L. McKnight, Dallas, TX (US);
Joseph M. Ready, Carrollton, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/487,963

(22) Filed: Jun. 4, 2012

(65) Prior Publication Data

US 2013/0143885 A1 Jun. 6, 2013

Related U.S. Application Data

(63) Continuation of application No. 11/974,479, filed on Oct. 12, 2007, now Pat. No. 8,193,225.

(60) Provisional application No. 60/829,338, filed on Oct. 13, 2006, provisional application No. 60/953,182, filed on Jul. 31, 2007.

(51) Int. Cl.
| | | |
|---|---|---|
| *A61K 31/422* | (2006.01) | |
| *A61K 31/427* | (2006.01) | |
| *A61K 31/4439* | (2006.01) | |
| *A61K 31/496* | (2006.01) | |
| *A61K 31/5377* | (2006.01) | |
| *A61K 31/415* | (2006.01) | |
| *A61K 31/4155* | (2006.01) | |
| *A61K 31/42* | (2006.01) | |

(52) U.S. Cl.
CPC ............ *A61K 31/415* (2013.01); *A61K 31/4155* (2013.01); *A61K 31/42* (2013.01); *A61K 31/422* (2013.01); *A61K 31/427* (2013.01); *A61K 31/4439* (2013.01); *A61K 31/496* (2013.01); *A61K 31/5377* (2013.01)
USPC ................... 514/236.8; 514/254.04; 514/340; 514/365; 514/378; 514/406

(58) Field of Classification Search
None
See application file for complete search history.

(56) References Cited

U.S. PATENT DOCUMENTS 5,201,932 A 4/1993 Maywald et al. ............. 504/271
2010/0331295 A1* 12/2010 Busch et al. ............. 514/210.18

FOREIGN PATENT DOCUMENTS

| DE | 10 2004 054 666 | 5/2006 |
|---|---|---|
| EP | 0 418 667 | 3/1991 |
| JP | 08-027130 | 1/1996 |
| WO | WO 03/013517 | 2/2003 |
| WO | WO 2009/006267 | 1/2009 |

OTHER PUBLICATIONS

Chandrasekhar et al., "Direct conversion of tosylhydrazones to tert-butyl ethers under bamford-stevens reaction conditions," *Synlett.*, 1779-1780, 2001.
Chi et al., Production of green fluorescent protein transgenic embryonic stem cells using the GENSAT bacterial artificial chromosome library, *PNAS*, 102:13490-13495, 2005.
Creemers et al., "Myocardin is a direct transcriptional target of Mef2, Tead and Foxo proteins during cardiovascular development," *Development*, 133:4245-4256, 2006.
Database Chemcats Chemical Abstract Service, XP002509165 retrieved from STN order Nos. AKL-P-1661072, AKL-P-1660956, AKL-P-1661210, AKL-P-1413044, AKL-P-1660951, AKL-P-1753501, Feb. 7, 2006.
Elliott et al., "A tyrosine-rich domain within homeodomain transcription factor Nkx2-5 is an essential element in the early cardiac transcriptional regulatory machinery," *Development*, 133:1311-22, 2006.
Hidaka et al., "Chamber-specific differentiation of Nkx2.5-positive cardiac precursor cells from murine embryonic stem cells," *The FASEB Journal*, published online Feb. 19, 2003.
Hsieh et al., "Histone deacetylase inhibition-mediated neuronal differentiation of multipotent adult neural progenitor cells," *Proc. Natl. Acad. Sci. USA*, 101:16659-16664, 2004.
Hsieh et al., "IGF-I instructs multipotent adult neural progenitor cells to become oligodendrocytes," *J. Cell Biol.*, 164:111-122, 2004.
Larabi et al., "Synthesis, structural study and electrochemical properties of copper(II) complexes derived from benzene- and p-toluenesulphonylhydrazones," *J. Serb. Chem. Soc.*, 68:85-95, 2003.
Leopoldo et al., "Design, synthesis, and binding affinities of potential positron emission tomography (PET) ligands for visualization of brain dopamine D-3 receptors," *J. Med. Chem.*, 49:358-365, 2006.
Machine translation of DE 10 2004 054 666, obtained from http://worldwide.espacenet.com/, accessed Aug. 11, 2011.
Machine translation of JP 08-027130, Jan. 30, 1996.
Morissette et al., "High-throughput crystallization: polymorphs, salts, co-crystals and solvates of pharmaceutical solids," *Advanced Drug Delivery Review*, 56:275-300, 2004.
Munshi et al., "Synthesis of aryl sulphonyl hydrazones and I-aryl sulphonyl 4-substituted thiosemicarbzaides," *Indian J Chem.*, 1:311-313, 1963.
Office Action issued in U.S. Appl. No. 11/974,479, mailed Aug. 16, 2011.
Office Action issued in U.S. Appl. No. 11/974,479, mailed Dec. 17, 2009.
Office Action issued in U.S. Appl. No. 11/974,479, mailed May 1, 2009.

(Continued)

*Primary Examiner* — Alicia L Otton
(74) *Attorney, Agent, or Firm* — Parker Highlander PLLC

(57) ABSTRACT

The present invention relates to compounds and methods for inducing neuronal differentiation in normal neural stem cells and brain cancer stem cells. The methods may take place in vitro, such as in isolates from the adult mammalian brain, or in vivo. Compounds and methods described herein may find use in the treatment of neurodegenerative and psychiatric diseases, the repair and regeneration of the nervous system, and in treatment of neurologic malignancy.

15 Claims, 32 Drawing Sheets
(13 of 32 Drawing Sheet(s) Filed in Color)

(56) References Cited

OTHER PUBLICATIONS

Office Action issued in U.S. Appl. No. 11/974,479, mailed Sep. 1, 2010.
Office Action issued in U.S. Appl. No. 12/183,884, mailed Sep. 3, 2010.
Office Action issued in U.S. Appl. No. 12/183,884, mailed Jan. 10, 2011.
Office Action issued in U.S. Appl. No. 13/116,574, mailed Jan. 26, 2012.
Office Action issued in U.S. Patent Appl. No. 13/116,574, dated Nov. 10, 2011.
Ozmen et al., "Synthesis, characterization and antibacterial activity of new sulfonyl hydrazine derivatives and their nickel (II) complexes," *Spectrochimica Acta*, Part A, 70:641-645, 2008.
PCT International Preliminary Report on Patentability issued in International Application No. PCT/US2007/081304, mailed Apr. 23, 2009.
PCT International Preliminary Report on Patentability issued in International Application No. PCT/US2008/071843, mailed Feb. 11, 2010.
PCT International Search Report and Written Opinion issued in International Application No. PCT/US2007/081304, mailed Oct. 7, 2008.
PCT International Search Report and Written Opinion issued in International Application No. PCT/US2008/071843, mailed Apr. 28, 2009.
PCT Invitation to Pay Additional Fees issued in International Application No. PCT/US2008/071843, dated Jan. 26, 2009.
PCT Invitation to Pay Additional Fees issued in International Application No. PCT/US2007/081304, mailed Jul. 8, 2008.
Pipes et al., "The myocardia family of transcriptional coactivators: versatile regulators of cell growth, migration, and myogenesis," *Genes and Develop.*, 20:1545-1556, 2006.
Rawat et al., "Study of photochomism in benzenesulfonylhydrazones," *Chemical Abstracts*, 110:74706, 1989.
Registry No. 857283-79-5, entered into Registry file on STN on Jul. 27, 2005.
Registry No. 921177-00-6, entered into Registry file on STN on Feb. 15, 2007.
Registry No. 922343-19-9, entered into Registry file on STN on Feb. 22, 2007.
Sasaki et al., "Novel generation and cycloaddition reactivity of n-phenylsulfonylbenzonitrilimine via thermal decomposition of n-(phenylsulfonyl)benzohydrazonoyl chloride," *Tetrahedrom*, 36:1565-1569, 1980.
Schneider and Olson, "Small molecules and the pharmacology of cardiac cell fate," Circulation Research 99 (5): pE37, Conference/meeting—3rd Annual Symposium of the American-Heart-Association-Council-on-Basic-Cardiovascular-Sciences, Keystone, CO, USA, Jul. 31-Aug. 3, 2006.
Shyam et al., "Antitumor 2-(Aminocarbonyl)-1,2-bis(methylsulfonyl)-1-(2-chloroethyl)-hydrazines," *Journal of Medicinal Chemistry*, 39:796-801, 1996.
Siemann et al., "N-arylsulfonyl hydrazones as inhibitors of IMP-1 metallo-β-lactamase," *Antimicrobial Agents and Chemotherapy*, 46:2450-2457, 2002.
Souillac et al., "Characterization of delivery systems, differential scanning calorimetry," *Encyclopedia of Controlled Drug Delivery*, John Wiley & Sons, pp. 212-227, 1999.
Suk Kim et al., "Expression of ErbB receptors in ES cell-derived cardiomyocytes," *Biochem. Biophys. Res. Commun.*, 309:241-6, 2003.
Takahashi et al., "Ascorbic acid enhances differentiation of embryonic stem cells into cardiac myocytes," *Circulation*, 107:1912-1916, 2003.
Tomishima et al., "Production of green fluorescent protein transgenic embryonic stem cells using the GENSAT bacterial artificial chromosome library," *Stem Cells.*, 25:39-45, 2007.
Vippagunta et al., "Crystalline solids," *Advanced Drug Delivery Reviews*, 48:3-26, 2001.
Yamashita et al., "Prospective identification of cardiac progenitors by a novel single cell-based cardiomyocyte induction," *FASEB J.*, 19:1534-1536, 2005.

\* cited by examiner

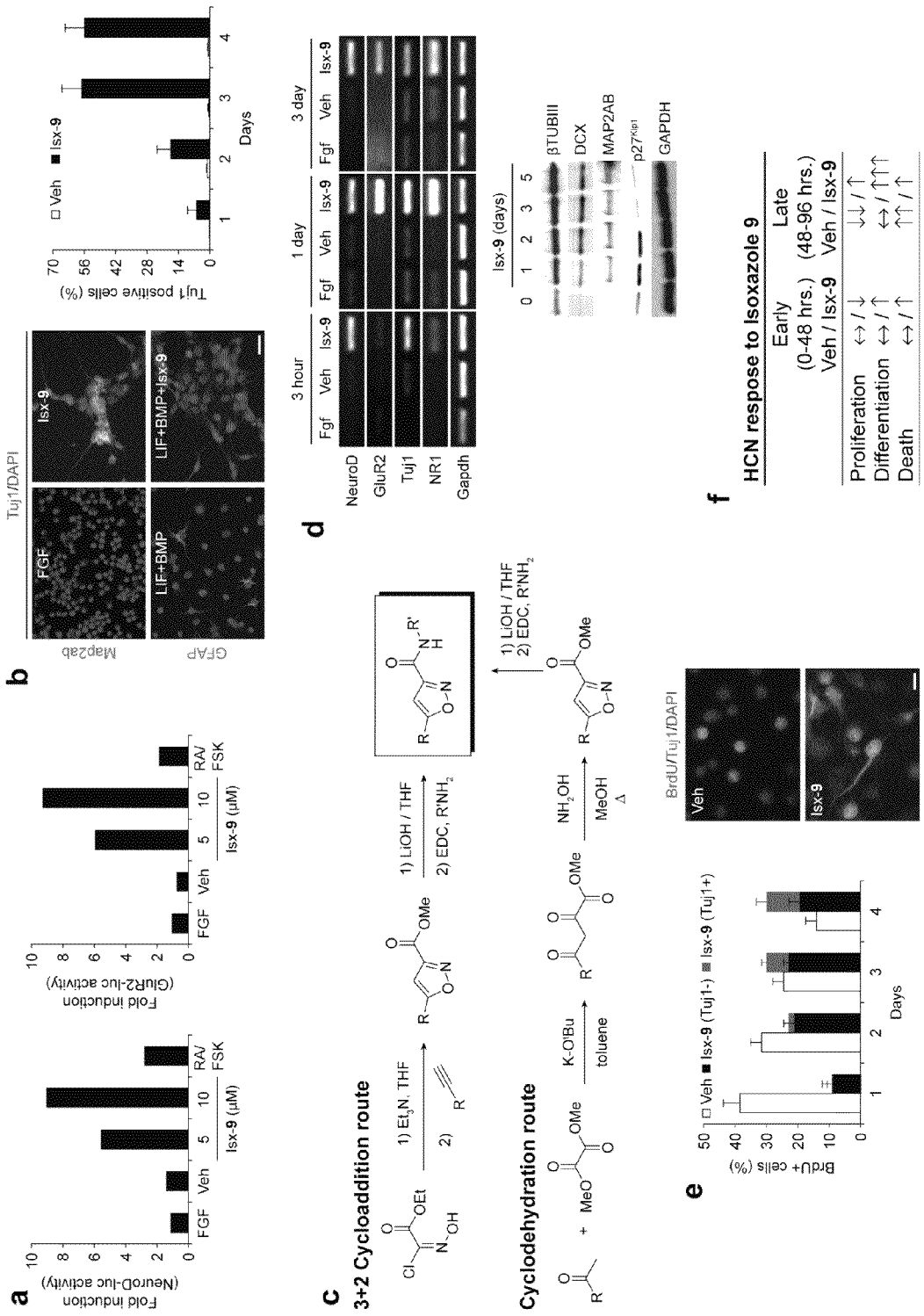
FIGS. 1a-f

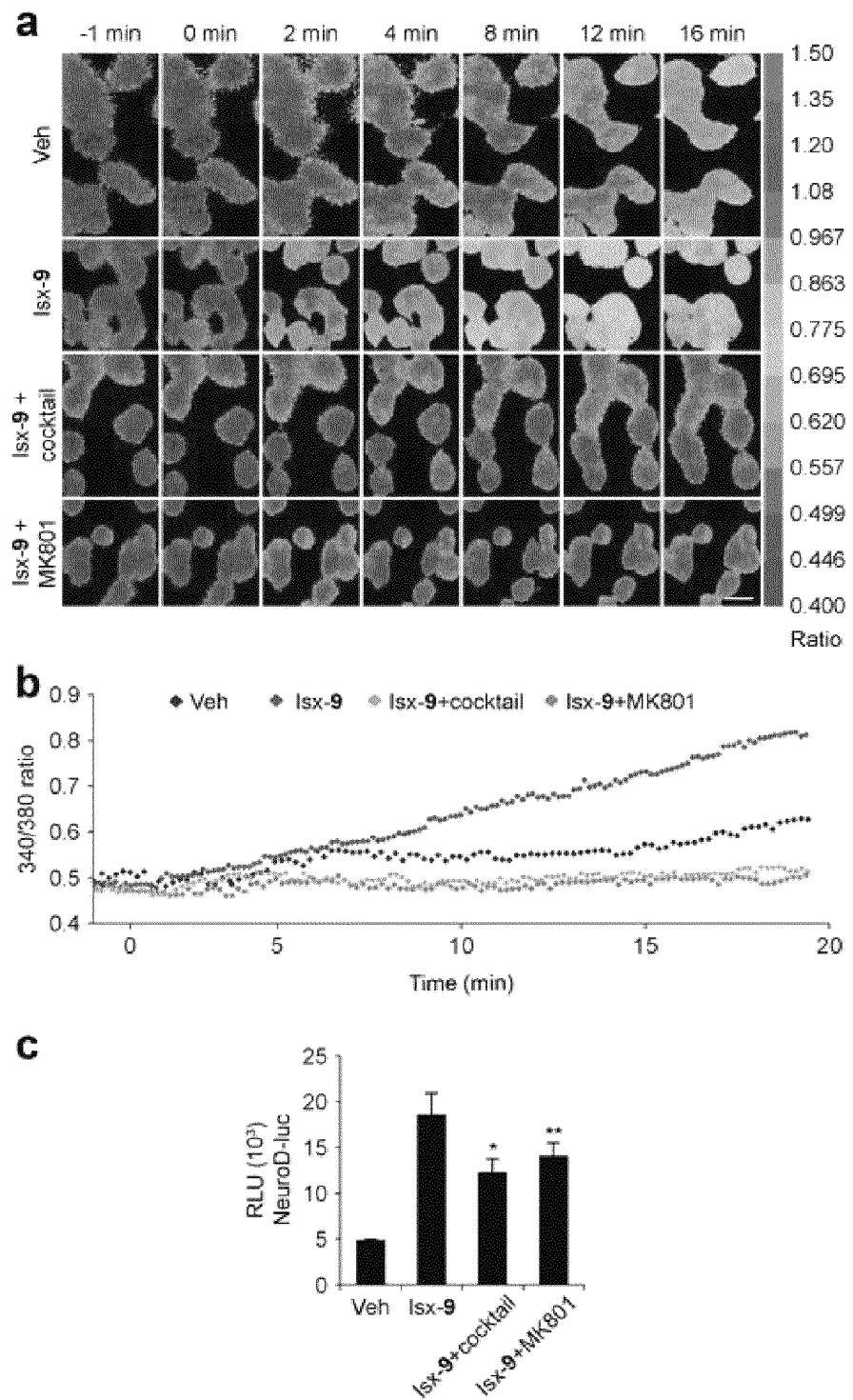
FIGS. 3a-c

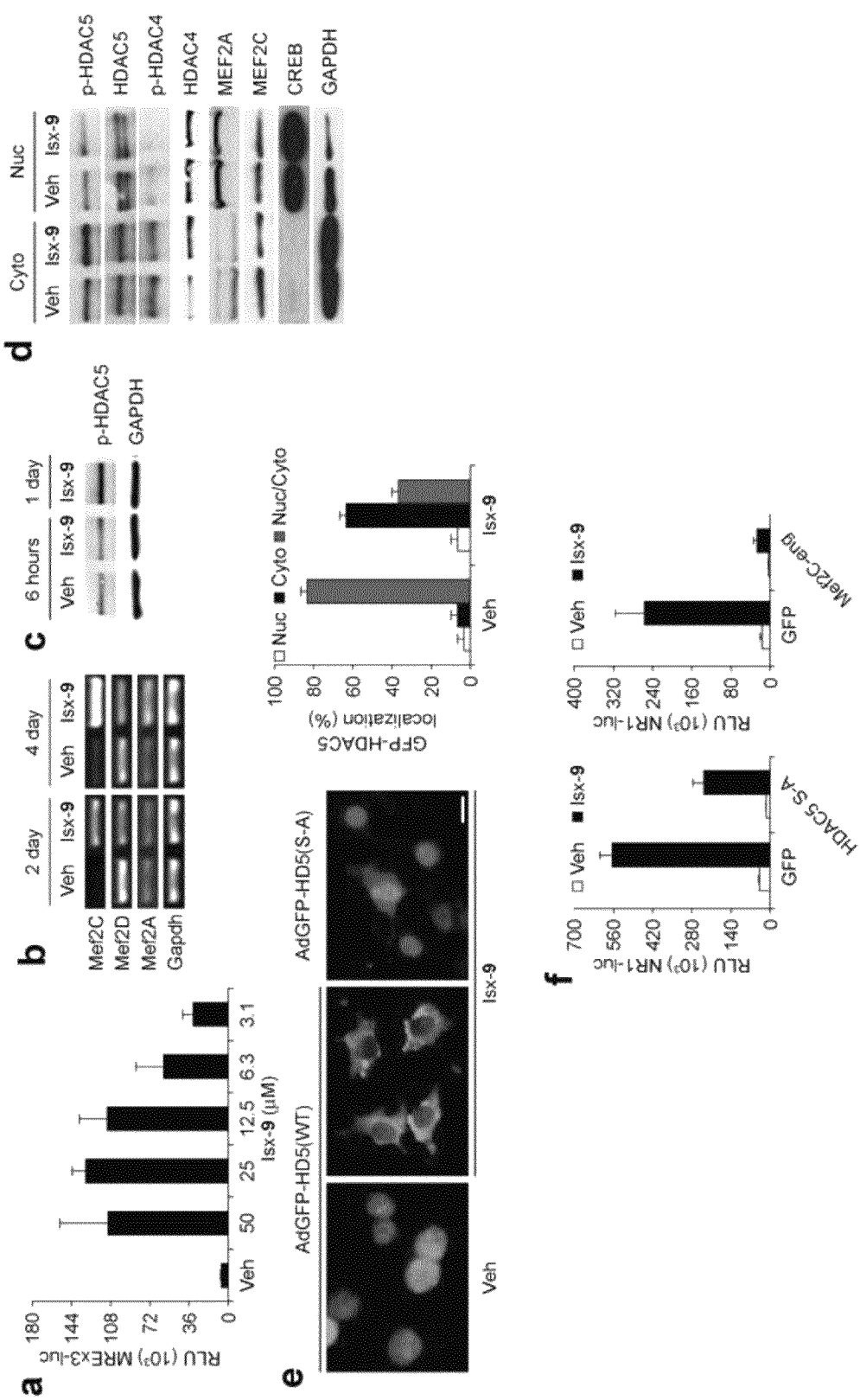
FIGS. 4a-f

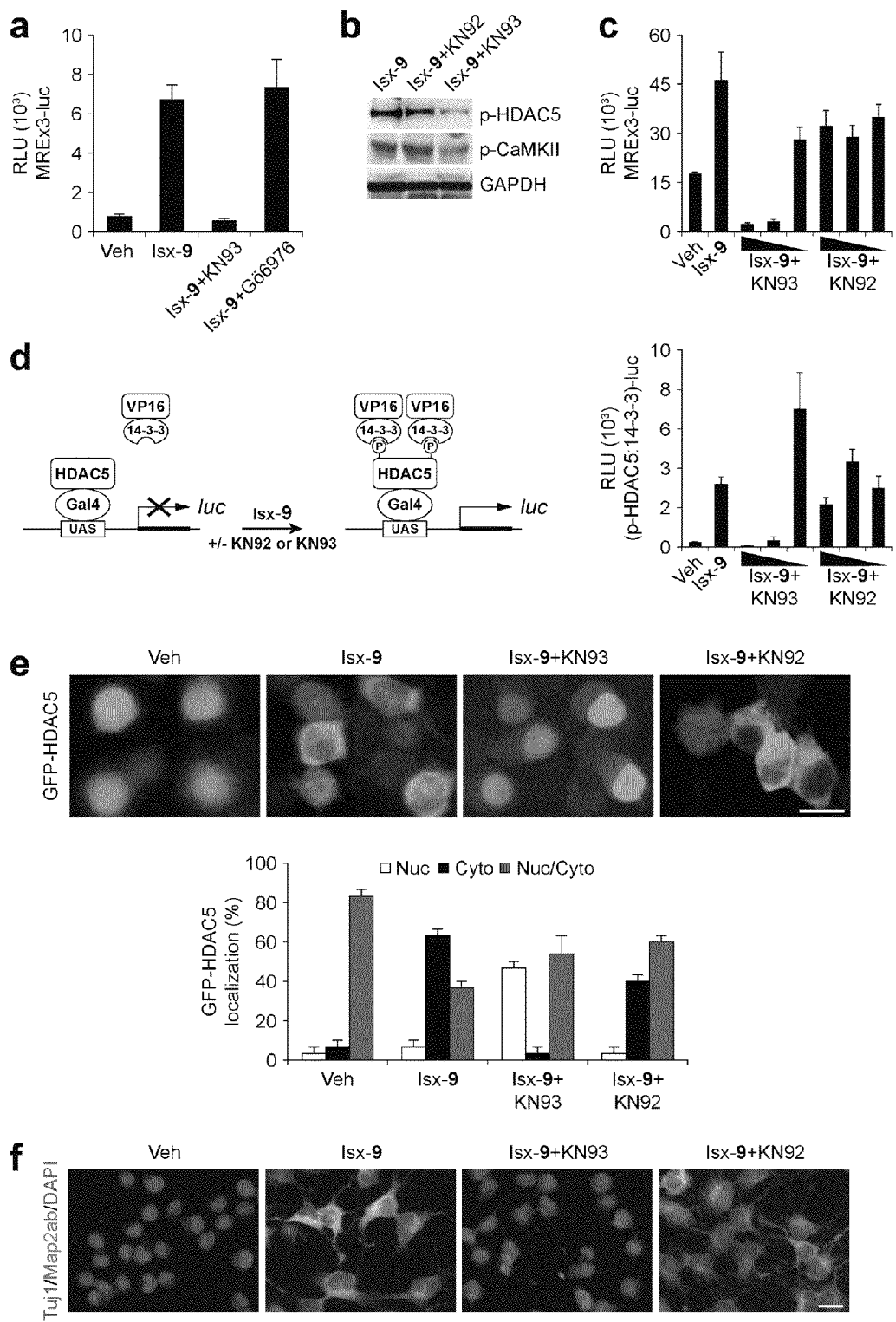
FIGS. 5a-f

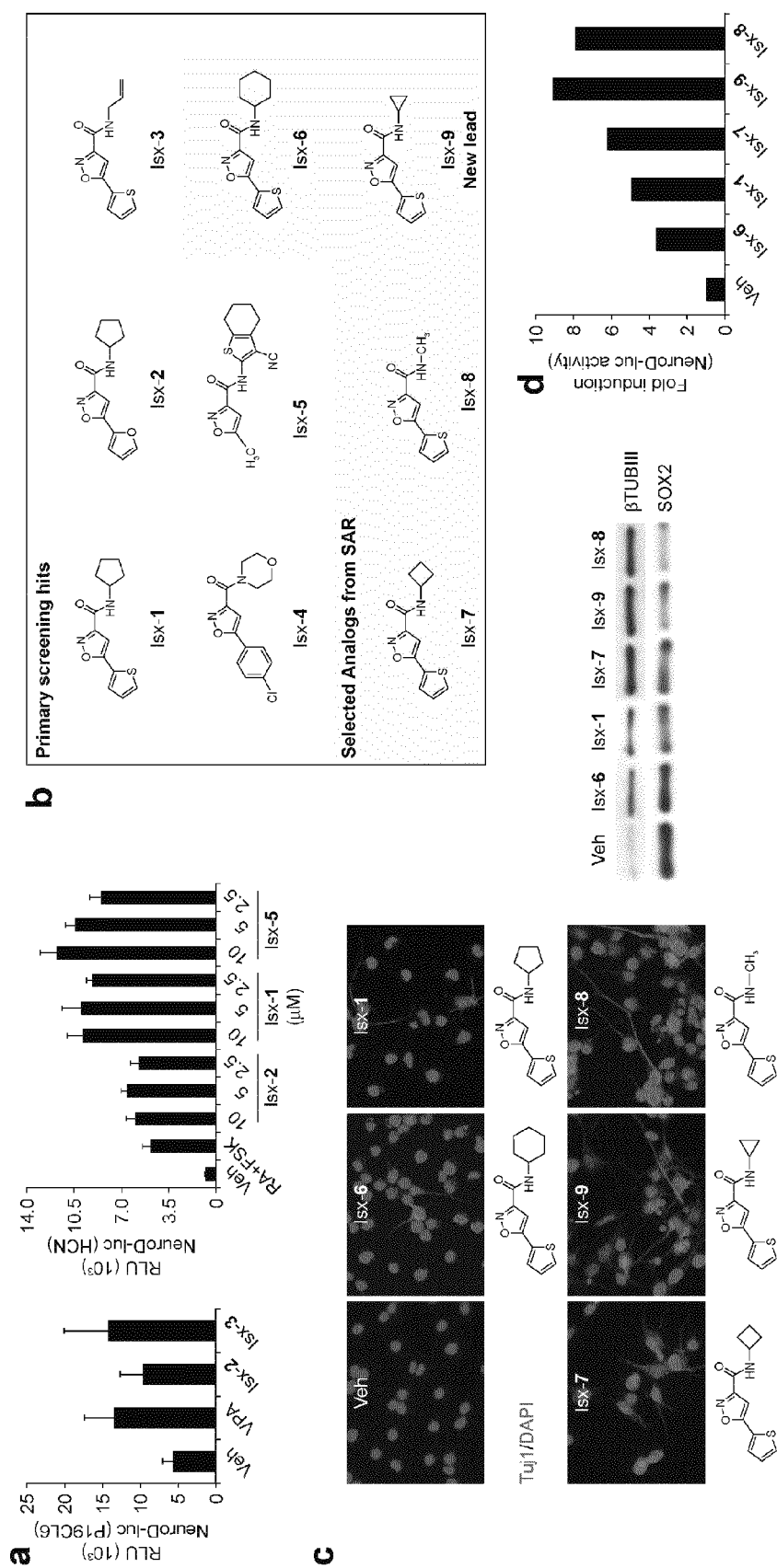
FIGS. 6a-d

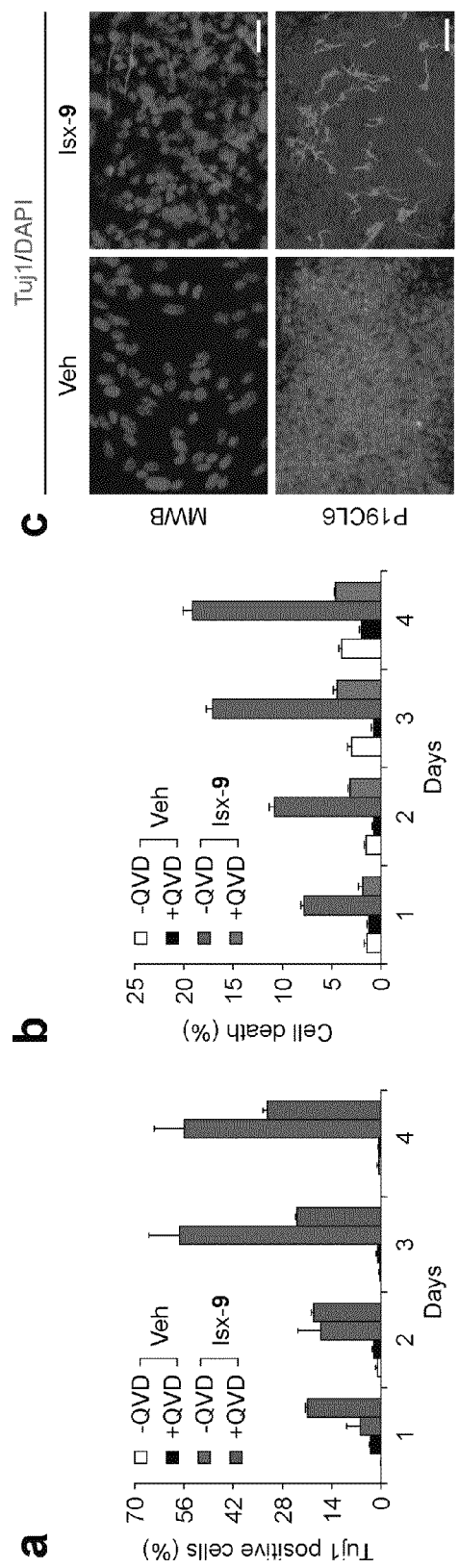
FIGS. 7a-c

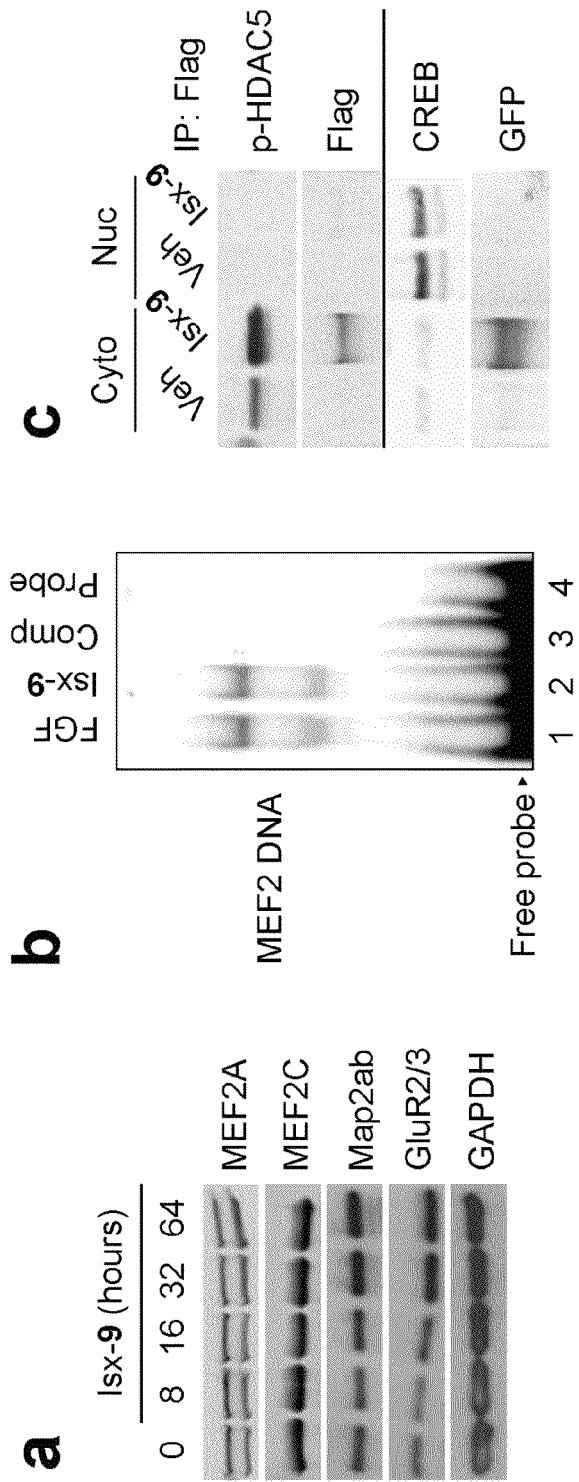
FIGS. 8a-c

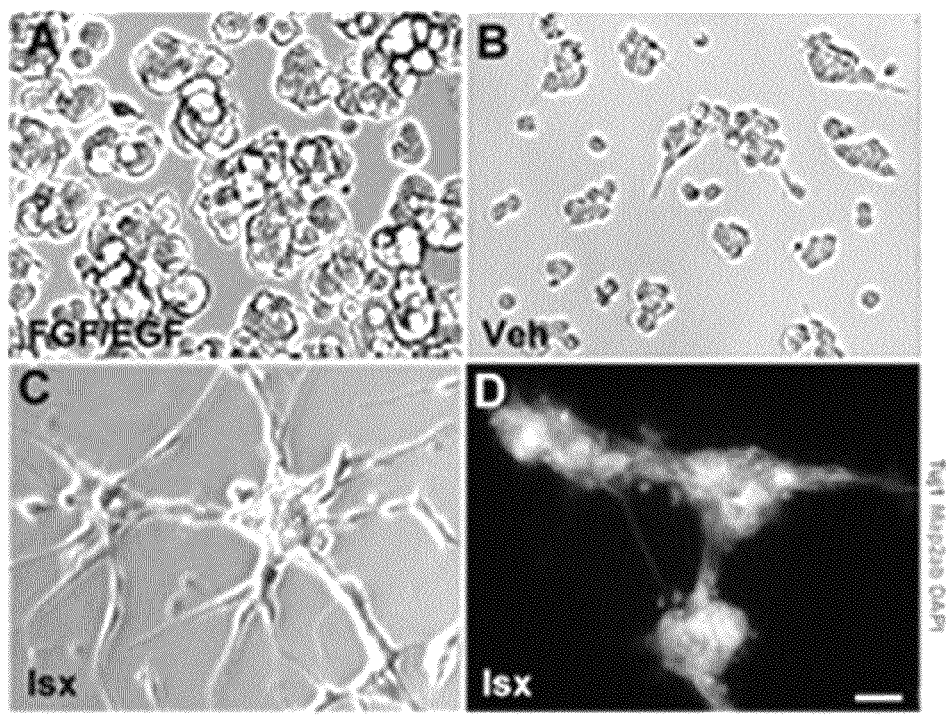
FIGS. 9 A-D

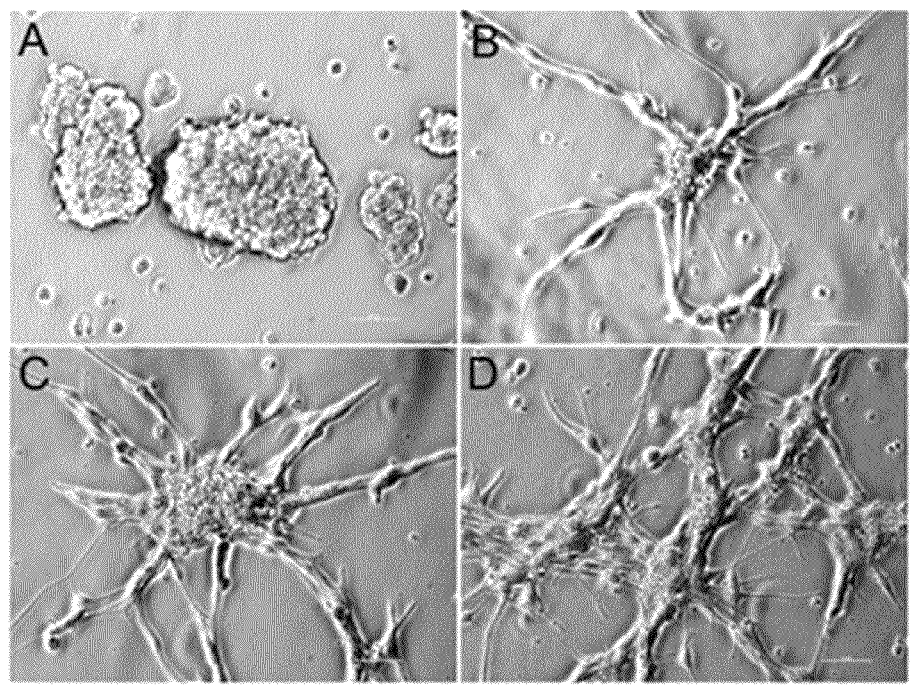
FIGS. 10 A-D

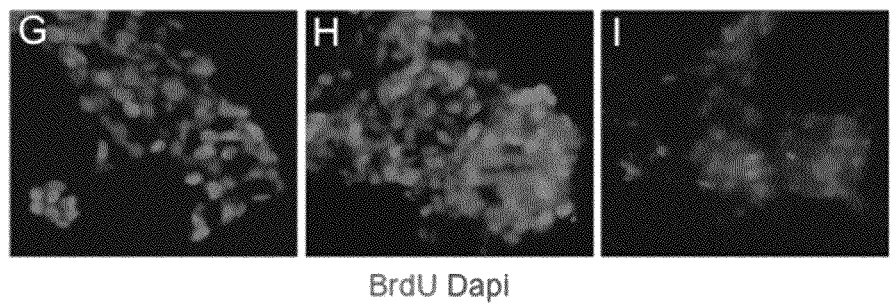
FIGS. 10 G-I

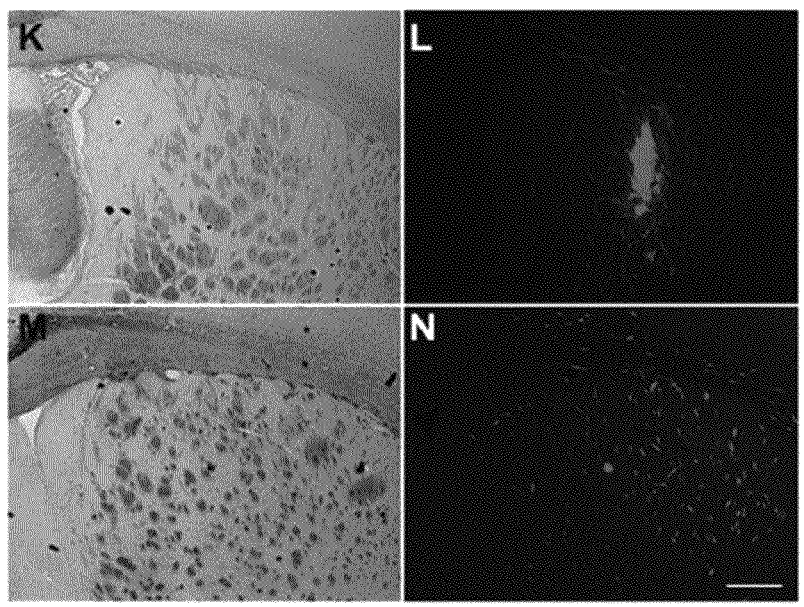
FIGS. 10 K-N

| Structure | Molecular Weight | Normalized to DF-279-10 (10 uM) | Fold Induction Above Vehicle | Fold Induction Above Media |
|---|---|---|---|---|
| 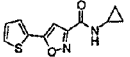 | 234.27 | | | |
| 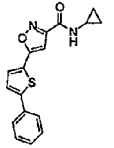 | 310.27 | 0.2366 | 1.6372 | 1.5889 |
| 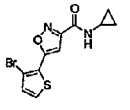 | 313.17 | 0.3375 | 2.3358 | 2.2668 |
| 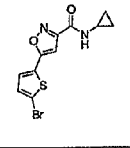 | 313.17 | 0.3059 | 2.1170 | 2.0544 |
| 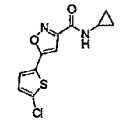 | 268.72 | 0.2883 | 1.9951 | 1.9361 |
| 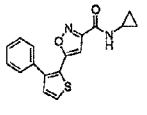 | 310.37 | 0.1566 | 1.0839 | 1.0519 |
| 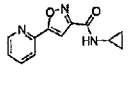 | 229.23 | 0.2397 | 1.6588 | 1.6098 |
| 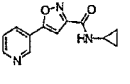 | 229.23 | 0.2204 | 1.5258 | 1.4807 |
FIG. 12A

| Structure | Molecular Weight | Normalized to DF-279-10 (10 uM) | Fold Induction Above Vehicle | Fold Induction Above Media |
|---|---|---|---|---|
| 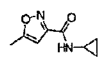 | 166.18 | 0.1295 | 0.8963 | 0.8698 |
| 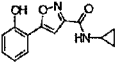 | 244.25 | 0.4303 | 2.5380 | 2.5531 |
| 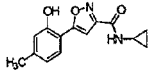 | 258.27 | 0.3546 | 2.0916 | 2.1041 |
| 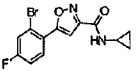 | 325.13 | 0.2291 | 1.3512 | 1.3593 |
| 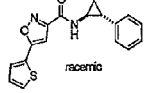 | 310.37 | 0.1458 | 0.8598 | 0.8649 |
| 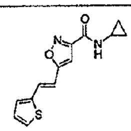 | 260.31 | 0.2888 | 1.7034 | 1.7136 |
| 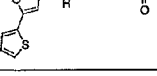 | 322.38 | 0.1894 | 1.1171 | 1.1237 |
| 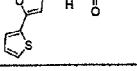 | 322.38 | 0.1644 | 0.9696 | 0.9754 |
| 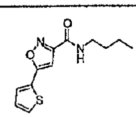 | 250.32 | 0.9213 | 5.4341 | 5.4665 |
| 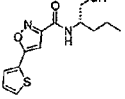 | 280.34 | 0.2349 | 1.5966 | 1.6412 |
FIG. 12B

| Structure | Molecular Weight | Normalized to DF-279-10 (10 uM) | Fold Induction Above Vehicle | Fold Induction Above Media |
|---|---|---|---|---|
| 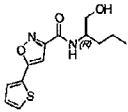 | 280.34 | 0.2960 | 2.0114 | 2.0676 |
| 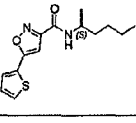 | 278.37 | 0.2249 | 1.5283 | 1.5710 |
| 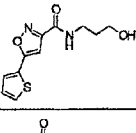 | 252.29 | 0.9076 | 6.1677 | 6.3402 |
| 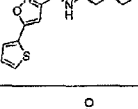 | 280.34 | 1.3873 | 9.4273 | 9.6908 |
| 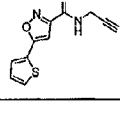 | 232.26 | 0.5984 | 4.0662 | 4.1799 |
| 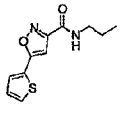 | 236.29 | 0.6061 | 4.1189 | 4.2341 |
| 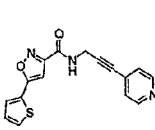 | 309.34 | 0.2647 | 1.7989 | 1.8491 |
| 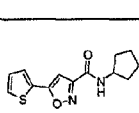 | 262.33 | 0.7539 | 3.3766 | 3.3602 |
| 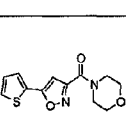 | 264.30 | 0.7075 | 1.6288 | 1.8732 |
FIG. 12C

| Structure | Molecular Weight | Normalized to DF-279-10 (10 uM) | Fold Induction Above Vehicle | Fold Induction Above Media |
|---|---|---|---|---|
| 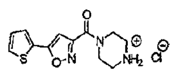 | 298.77 | 0.6387 | 1.4705 | 1.6912 |
| 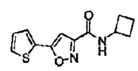 | 248.30 | 0.5647 | 1.3001 | 1.4952 |
| 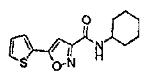 | 276.35 | 0.3426 | 1.5346 | 1.5271 |
| 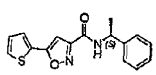 | 298.36 | 0.3940 | 0.9072 | 1.0433 |
| 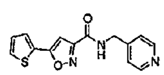 | 285.32 | 0.6282 | 1.4463 | 1.6633 |
| 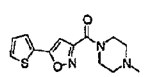 | 277.34 | 0.5913 | 1.3614 | 1.5657 |
| 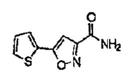 | 194.21 | 0.4915 | 1.1315 | 1.3013 |
| 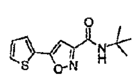 | 250.32 | 0.3963 | 0.9124 | 1.0493 |
| 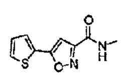 | 208.24 | 0.5659 | 1.4854 | 1.4206 |
| 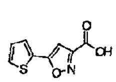 | 195.20 | 0.4021 | 1.0555 | 1.0094 |

FIG. 12D

| Structure | Molecular Weight | Normalized to DF-279-10 (10 uM) | Fold Induction Above Vehicle | Fold Induction Above Media |
|---|---|---|---|---|
| 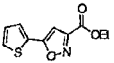 | 223.25 | 0.2072 | 0.9989 | 0.9237 |
| 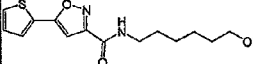 | 294.37 | 1.0702 | 2.8091 | 2.6865 |
| 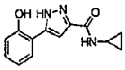 | 243.36 | 0.4524 | 1.1875 | 1.1356 |
| 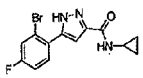 | 324.15 | 0.4926 | 1.2931 | 1.2367 |
| 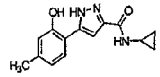 | 257.29 | 0.4836 | 1.2694 | 1.2139 |
| 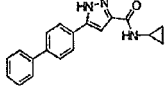 | 303.36 | 0.4460 | 1.1706 | 1.1195 |
| 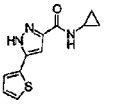 | 233.29 | 0.3004 | 0.7886 | 0.7542 |
| 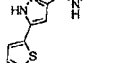 | 289.40 | 0.3719 | 1.3273 | 1.2885 |
| 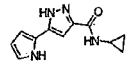 | 216.24 | 0.3832 | 1.3676 | 1.3276 |
| 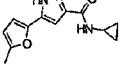 | 231.25 | 0.2973 | 1.0612 | 1.0302 |
FIG. 12E

| Structure | Molecular Weight | Normalized to DF-279-10 (10 uM) | Fold Induction Above Vehicle | Fold Induction Above Media |
|---|---|---|---|---|
| 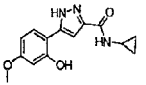 | 273.29 | 0.0738 | 0.2635 | 0.2558 |
| 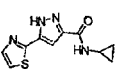 | 234.28 | 0.1827 | 0.6520 | 0.6329 |
| 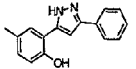 | 250.30 | 0.1576 | 0.5624 | 0.5459 |
| 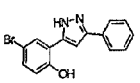 | 315.16 | 0.2866 | 1.0228 | 0.9929 |
| 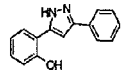 | 236.27 | 0.1795 | 0.6408 | 0.6221 |
| 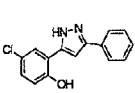 | 270.71 | 1.0151 | 4.5465 | 4.5245 |
| 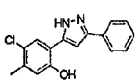 | 284.74 | 0.2985 | 1.3368 | 1.3303 |
| 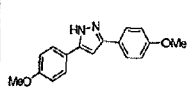 | 280.32 | 0.3922 | 1.7567 | 1.7482 |
| 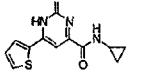 | 261.30 | 0.2267 | 1.0156 | 1.0107 |
| 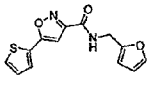 | 274.30 | 0.4200 | 2.0478 | 1.8566 |
FIG. 12F

| Structure | Molecular Weight | Normalized to DF-279-10 (10 uM) | Fold Induction Above Vehicle | Fold Induction Above Media |
|---|---|---|---|---|
| 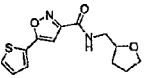 | 278.33 | 0.5429 | 2.6474 | 2.4002 |
| 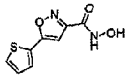 | 210.21 | 0.4187 | 1.5375 | 1.6885 |
| 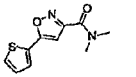 | 222.26 | 0.1303 | 0.4784 | 0.5254 |
| 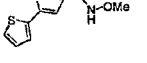 | 224.24 | 0.0099 | 0.0483 | 0.0438 |
| 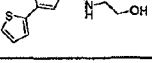 | 238.26 | 0.1016 | 0.4955 | 0.4493 |
| 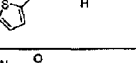 | 238.26 | 0.0303 | 0.1478 | 0.1340 |
| 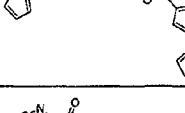 | 415.44 | 0.3276 | 1.5973 | 1.4482 |
| 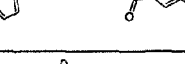 | 414.46 | 0.1266 | 0.6596 | 0.5106 |
| 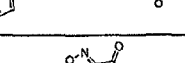 | 491.54 | 0.1637 | 0.8527 | 0.6601 |
| 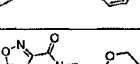 | 284.33 | 0.2731 | 1.3319 | 1.2075 |
| 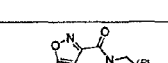 | 307.37 | 0.4462 | 1.6388 | 1.7998 |
| 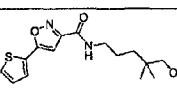 | 252.29 | 0.4134 | 1.5181 | 1.6672 |
| 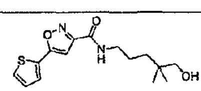 | 308.40 | 0.1349 | 0.6578 | 0.5964 |
FIG. 12G

| Structure | Molecular Weight | Normalized to DF-279-10 (10 uM) | Fold Induction Above Vehicle | Fold Induction Above Media |
|---|---|---|---|---|
| 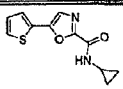 | 234.27 | 0.1971 | 0.8589 | 0.8903 |
| 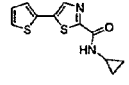 | 250.34 | 0.1079 | 0.4704 | 0.4875 |
| 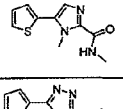 | 221.28 | 0.0216 | 0.1272 | 0.1136 |
| 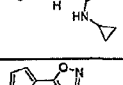 | 234.28 | 0.0137 | 0.0803 | 0.0717 |
| 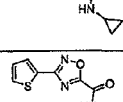 | 235.26 | 0.0230 | 0.1351 | 0.1206 |
| 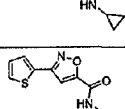 | 235.26 | 0.0636 | 0.3740 | 0.3339 |
| 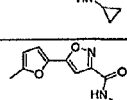 | 234.27 | 0.1771 | 1.0407 | 0.9292 |
| 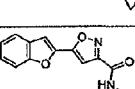 | 232.24 | 0.0282 | 0.1656 | 0.1479 |
| 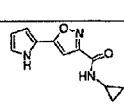 | 268.27 | 0.0199 | 0.1168 | 0.1043 |
| 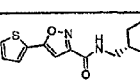 | 217.22 | 0.1422 | 0.8358 | 0.7462 |
| 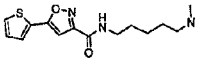 | 306.38 | 0.2151 | 0.9377 | 0.9719 |
| 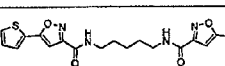 | 307.41 | 0.3971 | 2.1742 | 1.7943 |
| 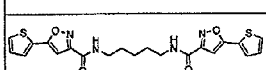 | 456.54 | 0.1449 | 0.7932 | 0.6546 |
| 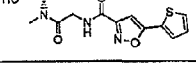 | 399.46 | 0.0334 | 0.1455 | 0.1509 |
FIG. 12H

| Structure | Molecular Weight | Normalized to DF-279-10 (10 uM) | Fold Induction Above Vehicle | Fold Induction Above Media |
|---|---|---|---|---|
| 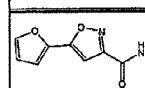 | 264.28 | 1.5713 | 6.8490 | 7.0990 |
| 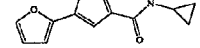 | 218.21 | 0.9304 | 4.0558 | 4.2038 |
| 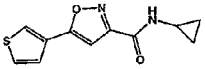 | 234.27 | 0.6943 | 2.5497 | 2.8001 |
| 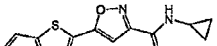 | 284.33 | 0.2448 | 0.8991 | 0.9874 |
These solutions were originally made in 10 mM solutions in amber 1.8 mL vials compared to the 100 mM solutions in 3.7 mL clear vials.
FIG. 12I

SEQUENCE LISTING

```
<160> NUMBER OF SEQ ID NOS: 1

<210> SEQ ID NO 1
<211> LENGTH: 12
<212> TYPE: DNA
<213> ORGANISM: Artificial
<220> FEATURE:
<223> OTHER INFORMATION: Synthetic primer

<400> SEQUENCE: 1
ttatttattt ag                                                         12
```

CHEMICAL INDUCERS OF NEUROGENESIS

This application is a continuation of U.S. application Ser. No. 11/974,479 filed Oct. 12, 2007, which claims the benefit of the filing dates of U.S. Provisional Application 60/829,338, filed Oct. 13, 2006 and U.S. Provisional Application 60/953,182, filed Jul. 31, 2007, the entire contents of each of these applications being hereby incorporated by reference.

BACKGROUND OF THE INVENTION

1. Field of the Invention

The present invention relates generally to the fields of cell biology, developmental biology and neurobiology. More particularly, it concerns methods and compositions relating to the induction of neural differentiation in stem cells.

2. Description of Related Art

Extensive evidence suggests that new neurons originate from stem cells in the adult mammalian hippocampus, a region of the brain that is important for learning and memory. The differentiation of stem cells into neurons begins within a month of the birth of a cell and continues throughout the adult life of the mammal (Gage et al. 1995). Hippocampal neurogenesis is a mechanism for maintaining cellular homeostasis in the adult brain and plays an important functional role in higher cerebral activities like learning and memory. While exercise and exposure to an enriched environment promote adult hippocampal neurogenesis, chronic stress, depression, sleep deprivation and aging can decrease neural stem/progenitor cell proliferation in the adult hippocampus.

In the mammalian central nervous system, adult multipotent neural progenitor cells cultured in the presence of retinoic acid (RA) differentiate into neurons (Palmer et al., 2001; Ray and Gage, 2006). By contrast, when such cells are cultured in the presence of insulin-like growth factor I (IGF-I) or leukemia inhibitory factor (LIF) plus bone-morphogenetic protein (BMP), they differentiate into oligodendrocytes and astrocytes, respectively (Hsieh et al. 2004). The cellular and molecular mechanisms that control the differentiation of adult hippocampal neural progenitor cells into neurons, oligodendrocytes and astrocytes are not completely understood.

Compounds that selectively direct stem cell fate could be useful for the treatment of neurodegenerative and psychiatric diseases and in the repair and regeneration of the nervous system. Chemicals can be identified that not only strongly favor neuronal differentiation, but also actively suppress astrocyte and oligodendrocyte differentiation. In addition, neurons whose differentiation has been induced in vitro could be used for stem cell grafting and transplantation. Ultimately, the study of multipotent neural progenitor cells in culture can be applied to studies of neurogenesis and gliogenesis in vivo, both in normal and in diseased and malignant states. Accordingly, potent inducers of neuronal differentiation of neural stem cells merit investigation.

As a corollary to the ability of a chemical compound to induce neurogenesis in a neural stem/progenitor cell, such a compound might also be an effective differentiation-inducing anti-neoplastic agent. Increasing evidence indicates that stem cells lie at the root of brain tumors like glioblastoma multiforme (GBM). Small-molecules that are active in neural stem/progenitor cells might therefore also have bioactivity against the brain tumor stem cell. Thus, small-molecules that induce neural stem cell differentiation might also be useful for arresting growth, killing, or differentiating GBM cancer stem cells, currently thought to be the cause of one of the most devastating and incurable of human malignancies.

Moreover, evidence is accumulating that primitive cancerous stem cells for hematopoietic cancers and several types of solid tumors exist. See, e.g., Cooper; 1992; Bonnet and Dick, 1997; Park et al., 1971; Hamburger and Salmon, 1977; and U.S. Pat. No. 4,411,990. Current methods for diagnosing or treating cancer, removing cancer cells from transplant grafts prior to injection into a patient, or methods to screen the efficacy of anti-cancer agents in completely eliminating cancer cells, do not account for the presence of cancer stem cells, which can propagate, differentiate into mature cancer cells and self-renew, thereby reforming cancers and leading to remissions. Accordingly, there exists a need for new methods for treating cancer which account for and/or are specifically directed to cancer stem cells.

SUMMARY OF THE INVENTION

The present invention is based on the discovery that certain compounds induce neuronal differentiation of stem cells. Accordingly, the present invention provides compounds, pharmaceutical compositions and methods relating to the induction of neuronal differentiation in a variety of stem cells. The compounds, compositions and methods of the present invention may be employed in vitro or in vivo. Neurologic malignancies, neurodegenerative and psychiatric diseases may be treated using the compounds and methods described herein. Certain cancers and cancer stem cells may also be targeted using compounds and methods of the present invention. Aspects of the present invention may also find use in the repair and regeneration of the nervous system.

Accordingly, certain aspects of the present invention contemplate a compound of formula (I):

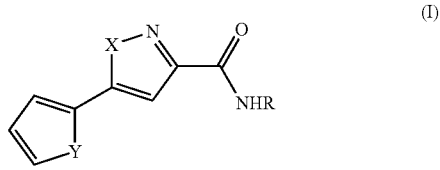

wherein X is O or NH, Y is S or O and R is H, a substituted or unsubstituted alkyl, such as $C_1$-$C_6$ alkyl or $C_3$-$C_6$ cycloalkyl, or a substituted or unsubstituted alkenyl, such as $C_2$-$C_6$ alkenyl, a substituted or unsubstituted alkynyl, such as $C_2$-$C_6$ alkynyl, or a stereoisomer, solvate, hydrate, or pharmaceutically acceptable salt thereof. In certain embodiments regarding compounds of formula (I), the proviso exists such that with the provisos that if X is O, then R must be a substituted or unsubstituted $C_3$-$C_6$ cycloalkyl; and/or if X is NH, then R must not be pyrazinyl substituted $C_1$-$C_6$ alkyl. Compounds of formula (I) may be employed in methods of the present invention, such as a method of inducing neuronal differentiation or treating cancer.

In certain embodiments regarding compounds of formula (I), Y is S and R is a substituted or unsubstituted $C_1$-$C_6$ alkyl. In certain embodiments, Y is S and R is a substituted or unsubstituted $C_3$-$C_6$ cycloalkyl. In certain embodiments, Y is O and R is a substituted or unsubstituted $C_3$-$C_6$ cycloalkyl. In certain embodiments, Y is O and R is a substituted or unsubstituted $C_1$-$C_6$ alkyl. In certain embodiments, R is a substituted or unsubstituted $C_2$-$C_6$ alkenyl. In certain embodiments, R is a substituted or unsubstituted $C_2$-$C_6$ alkynyl. In certain embodiments, R is H. In certain embodiments, X is O, Y is O and R is a substituted or unsubstituted cycloalkyl. In certain embodiments, X is O, Y is S and R is a substituted or unsubstituted cycloalkyl.

Other aspects of the present invention contemplate a compound of formula (Ia), (Ib), or (Ic):

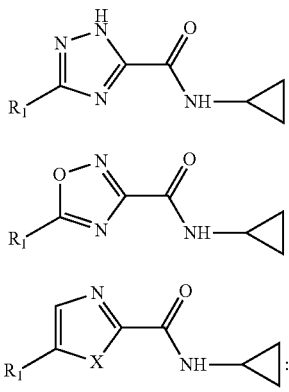

wherein R$_1$ is substituted or unsubstituted phenyl, unsubstituted pyrrolyl, unsubstituted pyridyl, unsubstituted furanyl, unsubstituted thienyl, unsubstituted benzofuranyl, unsubstituted benzo[b]thiophenyl, or unsubstituted thiazolyl. Any of these R$_1$ substituents may be substituted as well. Any one or more of compounds (Ia), (Ib) and (Ic) are contemplated in methods of the present invention, such as methods of inducing neuronal differentiation or treating cancer.

Also contemplated by the present invention are methods of inducing neuronal differentiation in a stem cell comprising contacting said stem cell with a compound of formula (II):

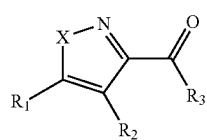

wherein: R$_1$ is substituted or unsubstituted thiophenyl or a substituent of formula (A):

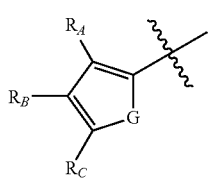

wherein: R$_A$, R$_B$ and R$_C$ are each independently selected from the group consisting of hydrogen, halogen, C$_1$-C$_6$ alkyl, C$_3$-C$_6$ cycloalkyl, aryl, cyano, nitro, and a carbonyl group; and G is O, —NH, or S; R$_2$ is hydrogen, hydroxy, halogen, nitro, aryl, alkyl, alkoxy, alkenyl, alkenyloxy, alkynyl, alkynyloxy, aralkyl, —CHO, —C(O)R$_9$, —OC(O)R$_9$, —OC(O)OR$_9$, —O(CN)OR$_9$, —C(O)NR$_9$R$_{10}$, —OC(O)NR$_9$R$_{10}$, —NR$_9$OR$_5$, or —SO$_3$R$_9$; wherein R$_9$ and R$_{10}$ are each independently hydrogen, alkyl, aryl, or aralkyl; R$_3$ is —NH—O-alkyl, —NH—OH, —OR$_{11}$ or —NR$_{11}$R$_{12}$, wherein R$_{11}$ and R$_{12}$ are each independently hydrogen, alkyl, alkenyl, alkynyl, aryl, or aralkyl; or R$_{11}$ and R$_{12}$ together form a cyclic group; or R$_{11}$ and R$_{12}$ together with the nitrogen to which they are bound form a cyclic group; X is O or —NR$_{13}$, wherein R$_{13}$ is hydrogen, alkyl, aryl, or aralkyl; or a stereoisomer, solvate, hydrate, or pharmaceutically acceptable salt thereof.

As used herein, the phrase "method of inducing neuronal differentiation in a stem cell" refers to, in certain embodiments, morphological change in a neural stem/progenitor cell or other cell contemplated by the present invention (described herein), flattening of such cells, and/or the extension of neuronal-like processes as associated with the contacting of such cells with a compound of the present invention. Induction of neuronal differentiation may also be associated with increased neuronal expression as detected by, for example, mRNA levels, protein levels, and/or neuronal markers. The terms "neuronal differentiation" and "neurogenic differentiation" are used interchangeably herein.

In certain embodiments regarding compounds of formula (II), any alkyl group comprised in any of R$_2$, R$_9$, R$_{10}$, R$_{11}$, R$_{12}$, or R$_{13}$ (such as alkyl, alkoxy, aralkyl, etc.) is lower alkyl. In certain embodiments, higher alkyls are contemplated in this context. In certain embodiments, any aryl group within a compound of formula (II) is mono-substituted. In certain embodiments, any aryl group within a compound of formula (II) is di-substituted (e.g., R$_1$, R$_A$, R$_B$, R$_C$, R$_2$, R$_9$, R$_{10}$, R$_{11}$, R$_{12}$, and/or R$_{13}$). In certain embodiments, any aryl group within a compound of formula (II) is tri-substituted. In certain embodiments, any aryl group within a compound of formula (II) is tetra-substituted. In certain embodiments, the cyclic group formed by R$_{11}$ and R$_{12}$ is cyclopropyl, cyclobutyl, or cyclopentyl. In certain embodiments, the cyclic group formed by R$_{11}$ and R$_{12}$ and the nitrogen to which it is bound to the rest of the molecule is piperazinyl or a salt thereof, or morpholino. In certain embodiments, R$_3$ is —OH. In certain embodiments, R$_3$ is alkoxy, such as ethoxy. In certain embodiments, R$_3$ is —NH$_2$. In certain embodiments, R$_3$ is —NH-alkyl-OH. In embodiments, R$_3$ is —NH-lower unsubstituted alkyl, including lower unsubstituted cycloalkyl (e.g., cyclopropyl). In certain embodiments, R$_3$ is —NH-substituted lower alkyl; in certain embodiments, such substitution may be by a hydroxy group, an —NH$_2$ group, or a lower alkoxy group. In certain embodiments, any aralkyl group of the compound of formula (II) is —CH$_2$-aryl. In certain embodiments, R$_3$ is —NH—O-alkyl.

In particular embodiments, a compound of formula (II) is further defined as a compound of formula (III):

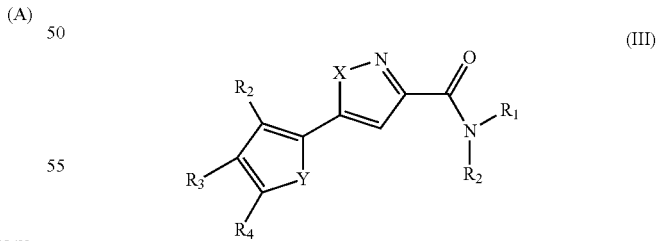

wherein: R$_1$ and R$_2$ are both hydrogen; or R$_1$ is hydrogen and R$_2$ is selected from the group consisting of substituted or unsubstituted C$_1$-C$_6$ alkyl, C$_3$-C$_6$ cycloalkyl, C$_2$-C$_6$ alkenyl, C$_2$-C$_6$ alkynyl and benzyl; or R$_1$ and R$_2$ may be joined together to form cyclic group, such as a ring selected from azetidinyl, pyrrolidinyl, piperidinyl, piperazinyl and morpholinyl; R$_2$, R$_3$ and R$_4$ are independently selected from the group consisting of hydrogen, halogen, alkyl, such as C$_1$-C$_6$ alkyl or $C_3$-$C_6$ cycloalkyl, aryl (such as substituted or unsubstituted aromatic or heteroaromatic ring), cyano, nitro, and a carbonyl group; X is O, NH, or S; and Y is O, NH, or S, or a stereoisomer, solvate, hydrate, or pharmaceutically acceptable salt thereof.

In certain embodiments regarding compounds of formula (III), Y is S and $R_2$ is a substituted or unsubstituted $C_1$-$C_6$ alkyl. In certain embodiments, Y is S and $R_2$ is a substituted or unsubstituted $C_3$-$C_6$ cycloalkyl. In certain embodiments, Y is O and $R_2$ is a substituted or unsubstituted $C_3$-$C_6$ cycloalkyl. In certain embodiments, Y is O and $R_2$ is a substituted or unsubstituted $C_1$-$C_6$ alkyl. In certain embodiments, Y is S and $R_2$ is a substituted or unsubstituted $C_2$-$C_6$ alkenyl, $C_2$-$C_6$ alkynyl or benzyl. In certain embodiments, Y is O and $R_2$ is a substituted or unsubstituted $C_2$-$C_6$ alkenyl, $C_2$-$C_6$ alkynyl or benzyl. In certain embodiments, $R_1$ is H.

In certain embodiments regarding methods of the present invention involving stem cells, said stem cell is located in an animal subject, such as mammal (e.g., mouse, human). In certain embodiments regarding methods of the present invention involving stem cells, said stem cell is contacted ex vivo. In any method involving stem cells, the stem cell may be, for example, an embryonic stem cell, an autologous embryonic stem cells generated through therapeutic cloning, an adult stem cell, a neural stem cell, a brain cancer stem cell, a cardiogenic stem cell, or a bone marrow stromal cells.

In certain embodiments, the compound of formula (II) is further defined as a compound of formula (IV):

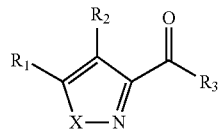

(IV)

wherein: $R^1$ is selected from alkyl, alkoxy, alkenoxy, alkynoxy, acyl, acyloxy, alkylamino, alkenylamino, alkynylamino, aryl and aralkyl. An alkyl group comprised in compounds of formula (IV) may be lower alkyl in certain embodiments, or higher alkyl in certain embodiments. Methods of inducing neuronal differentiation and treating cancer, for example, are methods of the present invention that may employ compounds of formula (IV).

In certain embodiments regarding compounds of formula (IV), $R^1$ is selected from $C_{1-6}$alkyl and a 5- or 6-membered ring containing atoms independently selected from the group consisting of C, N, O and S, wherein $R^1$ is optionally substituted with one or more substituents selected from the group consisting of hydroxy, halo, nitro, aryl, heteroaryl, $C_{1-6}$alkylhalo, alkyl, alkoxy, aralkyl, $OC_{1-6}$alkylhalo, $OC_{1-6}$alkyl, $C_{2-6}$alkenyl, $OC_{2-6}$alkenyl, $C_{2-6}$alkynyl, $OC_{2-6}$alkynyl, $C_{0-6}$alkyl$C_{3-6}$cycloalkyl, $OC_{0-6}$alkyl$C_{3-6}$cycloalkyl, $C_{1-6}$alkylaryl, $OC_{0-6}$alkylaryl, CHO, $(CO)R^4$, $O(CO)R^4$, $O(CO)OR^4$, $O(CN)OR^4$, $C_{1-6}$alkyl$OR^4$, $OC_{2-6}$alkyl$OR^4$, $C_{1-6}$alkyl$(CO)R^4$, $OC_{1-6}$alkyl$(CO)R^4$, $C_{0-6}$alkyl$CO_2R^4$, $OC_{1-6}$alkyl$CO_2R^4$, $C_{0-6}$alkylcyano, $OC_{2-6}$alkylcyano, $C_{0-6}$alkyl$NR^4R^5$, $OC_{2-6}$alkyl$NR^4R^5$, $C_{1-6}$alkyl$(CO)NR^4R^5$, $OC_{1-6}$alkyl$(CO)NR^4R^5$, $C_{0-6}$alkyl$NR^4(CO)R^5$, $OC_{2-6}$alkyl$NR^4(CO)R^5$, $C_{0-6}$alkyl$NR^4(CO)NR^4R^5$, $C_{0-6}$alkyl$SR^4$, $OC_{2-6}$alkyl$SR^4$, $C_{0-6}$alkyl$(SO)R^4$, $OC_{2-6}$alkyl$(SO)R^4$, $C_{0-6}$alkyl$SO_2R^4$, $OC_{2-6}$alkyl$SO_2R^4$, $C_{0-6}$alkyl$(SO_2)NR^4R^5$, $OC_{1-6}$alkyl$(SO_2)NR^4R^5$, $C_{0-6}$alkyl$NR^4(SO_2)R^5$, $OC_{2-6}$alkyl$NR^4(SO_2)R^5$, $C_{0-6}$alkyl$NR^4(SO_2)NR^4R^5$, $(CO)NR^4R^5$, $O(CO)NR^4R^5$, $NR^4OR^5$, $C_{0-6}$alkyl$NR^4(CO)OR^5$, $OC_{2-6}$alkyl$NR^4(CO)OR^5$ and $SO_3R^4$; $R^2$ is selected from the group consisting of hydrogen, hydroxy, halo, nitro, aryl, heteroaryl, $C_{1-6}$alkylhalo, $OC_{1-6}$alkylhalo, $C_{1-6}$alkyl, $OC_{1-6}$alkyl, $C_{2-6}$alkenyl, $OC_{2-6}$alkenyl, $C_{2-6}$alkynyl, $OC_{2-6}$alkynyl, $C_{0-6}$alkyl$C_{3-6}$cycloalkyl, $OC_{0-6}$alkyl$C_{3-6}$cycloalkyl, $C_{1-6}$alkylaryl, $OC_{0-6}$alkylaryl, CHO, $(CO)R^4$, $O(CO)R^4$, $O(CO)OR^4$, $O(CN)OR^4$, $C_{1-6}$alkyl$OR^4$, $OC_{2-6}$alkyl$OR^4$, $C_{1-6}$alkyl$(CO)R^4$, $OC_{1-6}$alkyl$(CO)R^4$, $C_{0-6}$alkyl$CO_2R^4$, $OC_{1-6}$alkyl$CO_2R^4$, $C_{0-6}$alkylcyano, $OC_{2-6}$alkylcyano, $C_{0-6}$alkyl$NR^4R^5$, $OC_{2-6}$alkyl$NR^4R^5$, $C_{1-6}$alkyl$(CO)NR^4R^5$, $OC_{1-6}$alkyl$(CO)NR^4R^5$, $C_{0-6}$alkyl$NR^4(CO)R^5$, $OC_{2-6}$alkyl$NR^4(CO)R^5$, $C_{0-6}$alkyl$NR^4(CO)NR^4R^5$, $C_{0-6}$alkyl$SR^4$, $OC_{2-6}$alkyl$SR^4$, $C_{0-6}$alkyl$(SO)R^4$, $OC_{2-6}$alkyl$(SO)R^4$, $C_{0-6}$alkyl$SO_2R^4$, $OC_{2-6}$alkyl$SO_2R^4$, $C_{0-6}$alkyl$(SO_2)NR^4R^5$, $OC_{2-6}$alkyl$(SO_2)NR^4R^5$, $C_{0-6}$alkyl$NR^4(SO_2)R^5$, $OC_{2-6}$alkyl$NR^4(SO_2)R^5$, $C_{0-6}$alkyl$NR^4(SO_2)NR^4R^5$, $OC_{2-6}$alkyl$NR^4(SO_2)NR^4R^5$, $(CO)NR^4R^5$, $O(CO)NR^4R^5$, $NR^4OR^5$, $C_{0-6}$alkyl$NR^4(CO)OR^5$, $OC_{2-6}$alkyl$NR^4(CO)OR^5$ and $SO_3R_4$; $R^3$ is selected from the group consisting of $OR^4$, $NR^4R^5$, and $NR^7R^8$, wherein $R^7$ and $R^8$, together with the nitrogen atom to which they are bound, combine to form a 5- to 6-member ring optionally containing one or more of S, O, and NH; $R^4$ and $R^5$ are independently selected from the group consisting of hydrogen, $C_{1-6}$alkyl, $C_{1-6}$alkylaryl, $C_{1-6}$alkylheteroaryl, $C_{3-7}$cycloalkyl and aryl; and X is O or $NR^6$, wherein $R^6$ is selected from the group consisting of hydrogen, $C_{1-6}$alkyl, $C_{1-6}$alkylaryl, $C_{1-6}$alkylheteroaryl, $C_{3-7}$cycloalkyl and aryl; or a stereoisomer, solvate, hydrate, or pharmaceutically acceptable salt thereof.

Also contemplated by the present invention are methods of inducing neuronal differentiation in a stem cell comprising contacting said stem cell with a compound having formula (V):

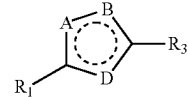

(V)

wherein: the ABD ring comprises two non-adjacent double bonds; A, B and D are each independently S, N, O, C, —$NR_{14}$, —$CR_{15}$, or —$CR_{15}R_{16}$, wherein $R_{14}$ is hydrogen, halogen, alkyl, aryl, or aralkyl; and $R_{15}$ and $R_{16}$ are each independently hydrogen, hydroxy, halogen, nitro, aryl, alkyl, alkoxy, alkenyl, alkenyloxy, alkynyl, alkynyloxy, aralkyl, —CHO, —$C(O)R_9$, —$OC(O)R_9$, —$OC(O)OR_9$, —$O(CN)OR_9$, —$C(O)NR_9R_{10}$, —$OC(O)NR_9R_{10}$, —$NR_9OR_5$, or —$SO_3R_9$; wherein $R_9$ and $R^{10}$ are each independently hydrogen, alkyl, aryl, or aralkyl, provided that at least two of A, B and D comprise S, N, or O; $R_1$ is alkyl, —CH═CH-aryl, or aryl; and $R_3$ is alkyl, —C(O)alkyl, aryl, —C(O)aryl, aralkyl, —C(O)aryl, —$OR_4$, —$C(O)R_4$, —$NR_4R_5$, or —$C(O)NR_4R_5$, wherein: $R_4$ and $R_5$ are each independently hydrogen, alkyl, aryl, or aralkyl; or $R_4$ and $R_5$ together form a cyclic group; or $R_4$ and $R_5$ together with the nitrogen to which they are bound form a cyclic group. In certain embodiments, the D atom and $R_3$ come together to form a cyclic group.

In certain embodiments regarding compounds of the present invention, such as compounds of formula (V), the proviso exists such that compounds of formula ($V_a$) are excluded:

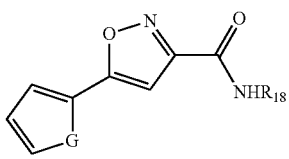

(V$_a$)

wherein R$_{18}$ is alkyl, such as lower alkyl or cyclopentyl, or alkenyl, such as lower alkenyl or allyl, and G is O or S. In certain embodiments regarding compounds of formula (V), any alkyl group comprised in R$_1$, R$_4$, R$_5$, R$_9$, R$_{10}$, R$_{14}$, R$_{15}$, and/or R$_{16}$ is lower alkyl. Higher alkyls are also contemplated in this respect, in certain embodiments. Regarding R$_1$, the aryl group of either aryl-containing R$_1$ substituent may, in certain embodiments, be substituted or unsubstituted pyranyl, thiophenyl, furanyl, thiazolyl, or pyridinyl. In certain embodiments, R$_4$ and R$_5$ together form a cyclopropyl group. In certain embodiments, R$_3$ is —NR$_4$R$_5$.

It is specifically contemplated that, in certain embodiments, ABD rings of the present invention are substituted at R$_1$ and R$_3$, but not at any other available ring atom of the ABD ring.

In certain embodiments, the compound of formula (V) is a compound of formula (V$_b$):

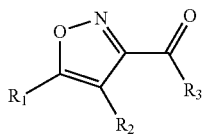

(V$_b$)

wherein: R$_1$ and R$_2$ are each independently hydrogen, alkyl, —CH=CH-aryl, aralkyl, or aryl; and R$_3$ is alkyl, aryl, aralkyl, —OR$_4$, or —NR$_4$R$_5$, wherein: R$_4$ and R$_5$ are each independently hydrogen, alkyl, aryl, or aralkyl; or R$_4$ and R$_5$ together form a cyclic group; or R$_4$ and R$_5$ together with the nitrogen to which they are bound form a cyclic group. In certain embodiments regarding compounds of formula (V$_b$), the proviso exists such that compounds of formula (V$_a$) are excluded:

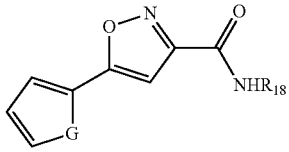

(V$_a$)

wherein R$_{18}$ is alkyl, such as lower alkyl or cyclopentyl, or alkenyl, such as lower alkenyl or allyl, and G is O or S.

In certain embodiments, a compound of formula (V) is further defined as a compound of formula (VI):

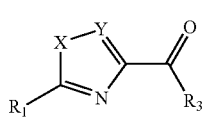

(VI)

wherein: R$_1$ is aryl or —CH=CH-aryl; R$_3$ is —OR$_4$ or —NR$_4$R$_5$, wherein: R$_4$ and R$_5$ are each independently hydrogen, alkyl, aryl, or aralkyl; and R$_4$ and R$_5$ together form a cyclic group; or R$_4$ and R$_5$ together with the nitrogen to which they are bound form a cyclic group; X is O, S, or —NR$_6$, wherein R$_6$ is hydrogen, alkyl, aryl, or aralkyl; and Y is N or —CR$_7$, wherein R$_7$ is hydrogen, alkyl, aryl, or halogen, or a stereoisomer, solvate, hydrate or pharmaceutically acceptable salt thereof.

In certain embodiments, a compound of formula (V) is further defined as a compound of formula (VII):

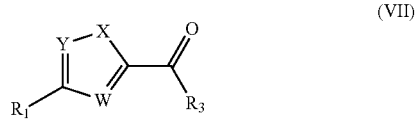

(VII)

wherein: R$_1$ is aryl or —CH=CH-aryl; R$_3$ is —OR$_4$ or —NR$_4$R$_5$, wherein: R$_4$ is hydrogen, alkyl, aryl, or aralkyl; and R$_5$ is alkyl, aryl, or aralkyl; or R$_4$ and R$_5$ together form a cyclic group; or R$_4$ and R$_5$ together with the nitrogen to which they are bound form a cyclic group; W is N or —CR$_8$, wherein R$_8$ is hydrogen, hydroxy, halogen, nitro, aryl, alkyl, alkoxy, alkenyl, alkenyloxy, alkynyl, alkynyloxy, aralkyl, —CHO, —C(O)R$_9$, —OC(O)R$_9$, —OC(O)OR$_9$, —O(CN)OR$_9$, —C(O)NR$_9$R$_{10}$, —OC(O)NR$_9$R$_{10}$, —NR$_9$OR$_5$, or —SO$_3$R$_9$; wherein R$_9$ and R$_{10}$ are each independently hydrogen, alkyl, aryl, or aralkyl; X is O, S, or —NR$_6$, wherein R$_6$ is hydrogen, alkyl, aryl, or aralkyl; and Y is N or —CR$_7$, wherein R$_7$ is hydrogen, alkyl, aryl, or halogen, or a stereoisomer, solvate, hydrate or pharmaceutically acceptable salt thereof.

In particular embodiments regarding compounds of formula (V), the ABD ring is selected from the group consisting of:

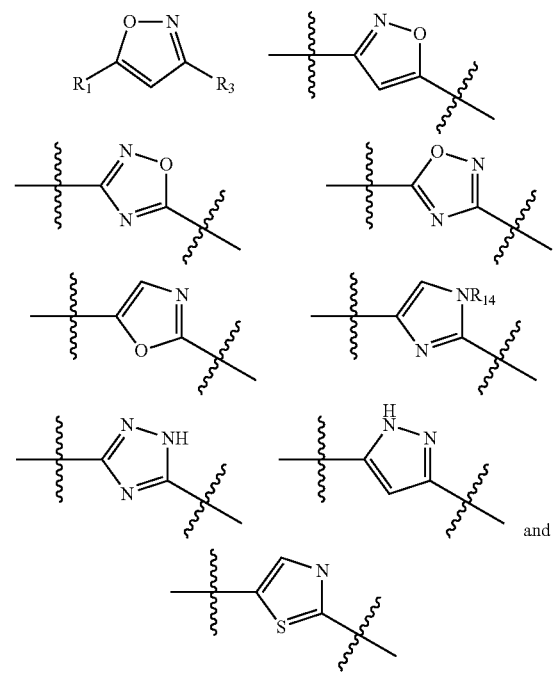

and wherein the substituent pictured to the left is R$_1$ and the substituent pictured to the right is R$_3$. In certain embodiments, $R_1$ and $R_3$ are reversed in this regard. In particular embodiments, the ABD ring is

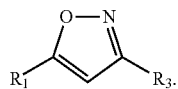

In certain embodiments, any one or more of these ABD rings is excluded from the present invention. In particular embodiments, the following ABD ring is excluded:

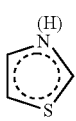

wherein $R_1$ and $R_3$ may be attached at any of this ABD ring's 3 available ring carbon atoms.

Specific compounds, such as those shown below, are also contemplated by the present invention. Such compounds may be compounds of formula (II) and/or (V), for example.

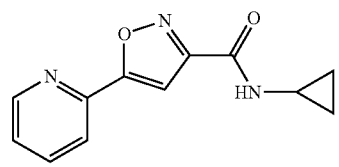

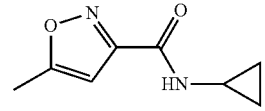

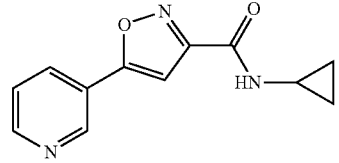

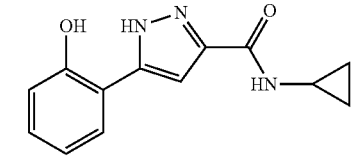

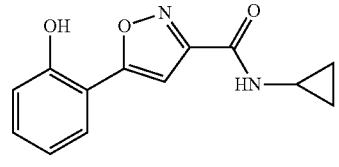

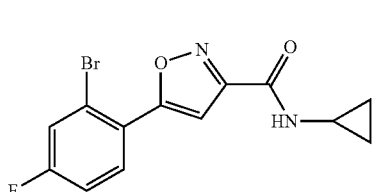

-continued

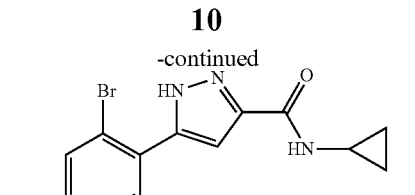

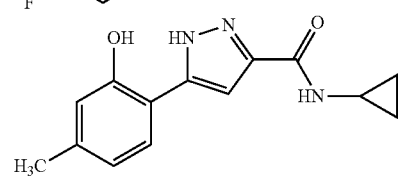

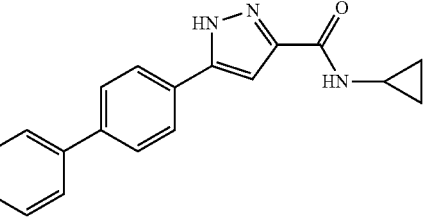

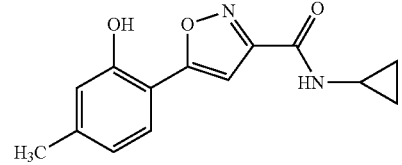

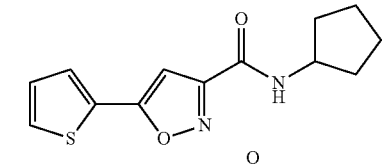

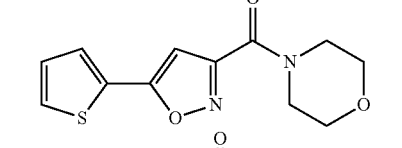

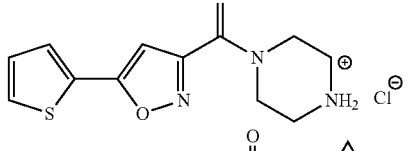

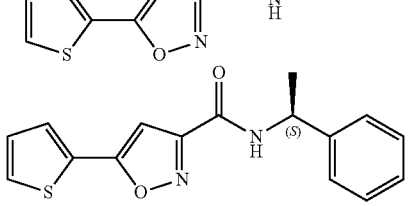

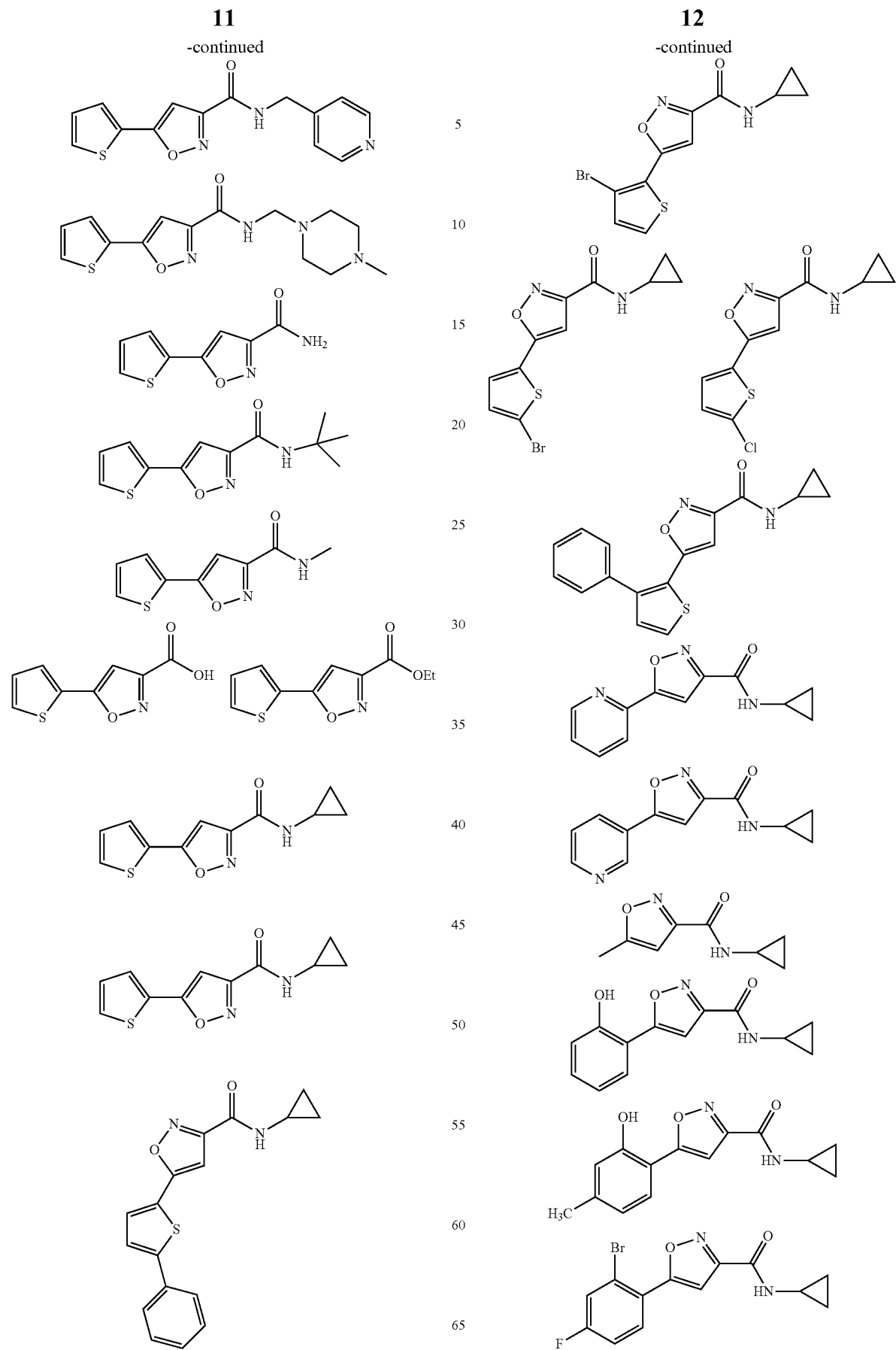

13
-continued
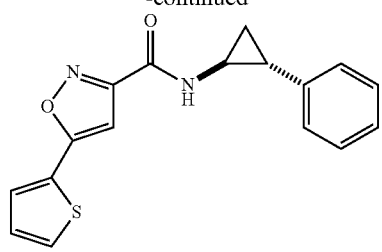
racemic
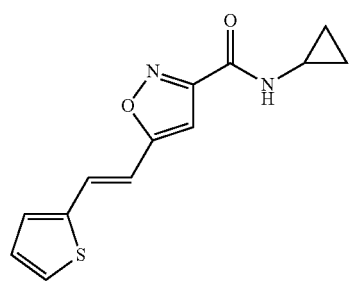
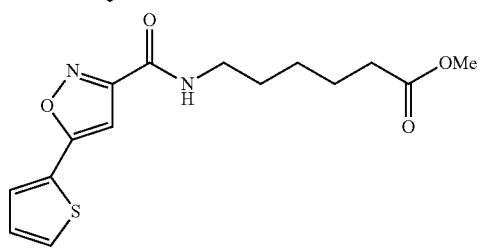
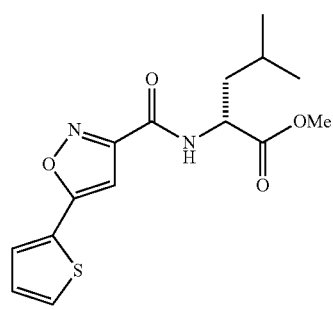
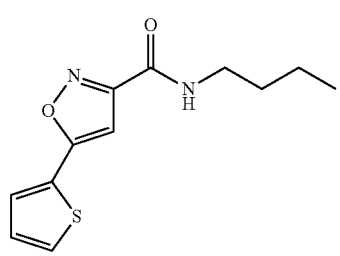
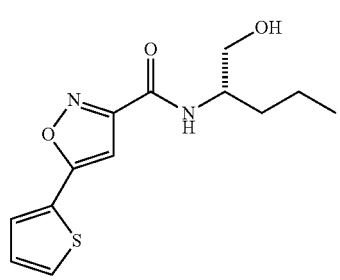
14
-continued
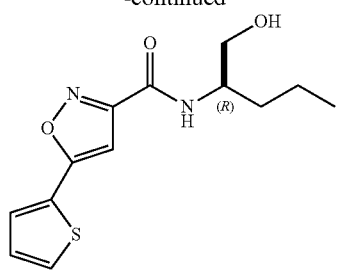
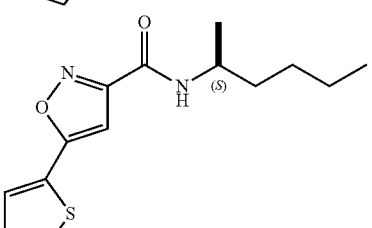
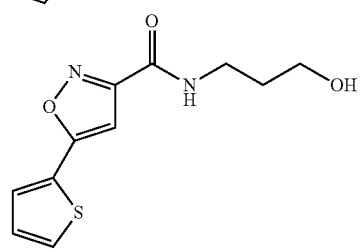
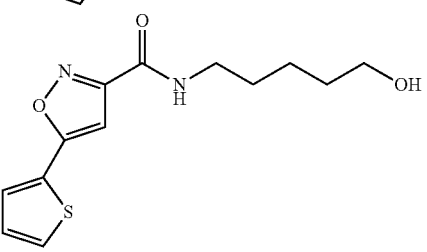
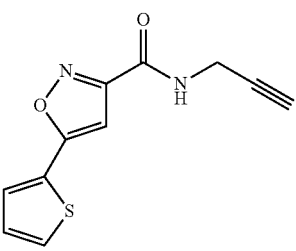
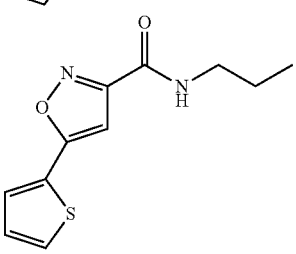
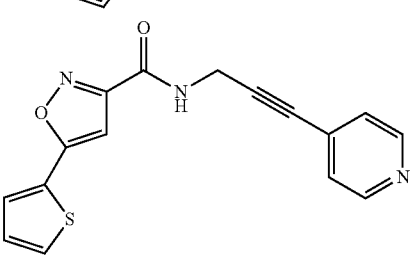

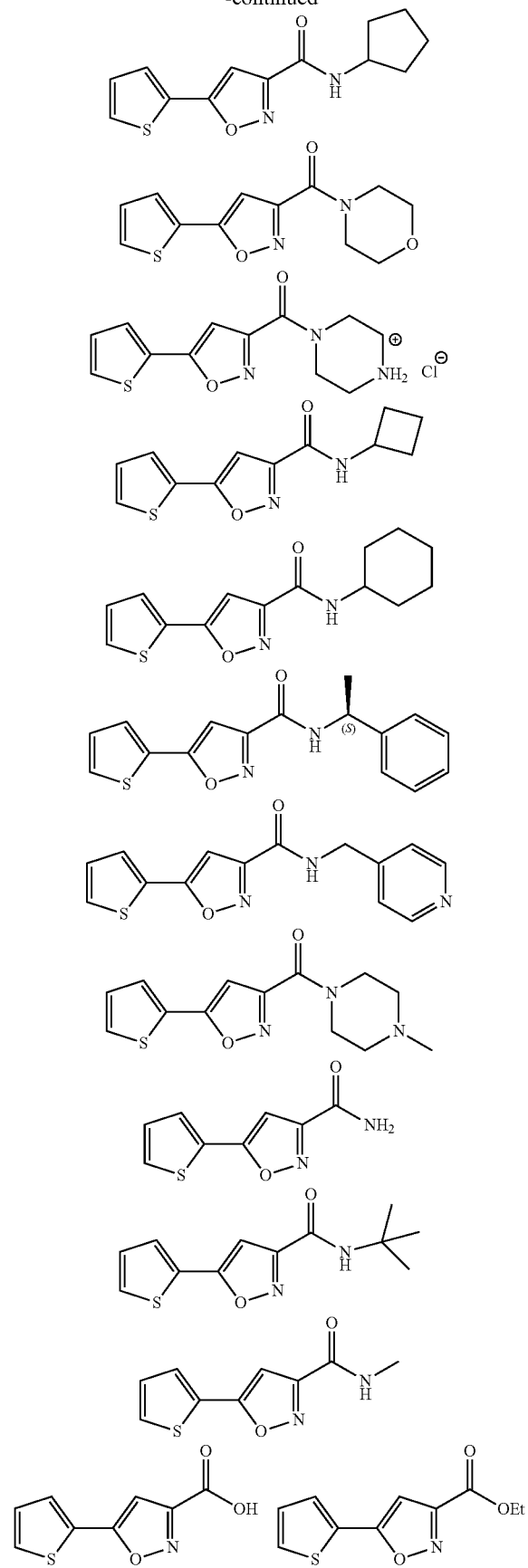
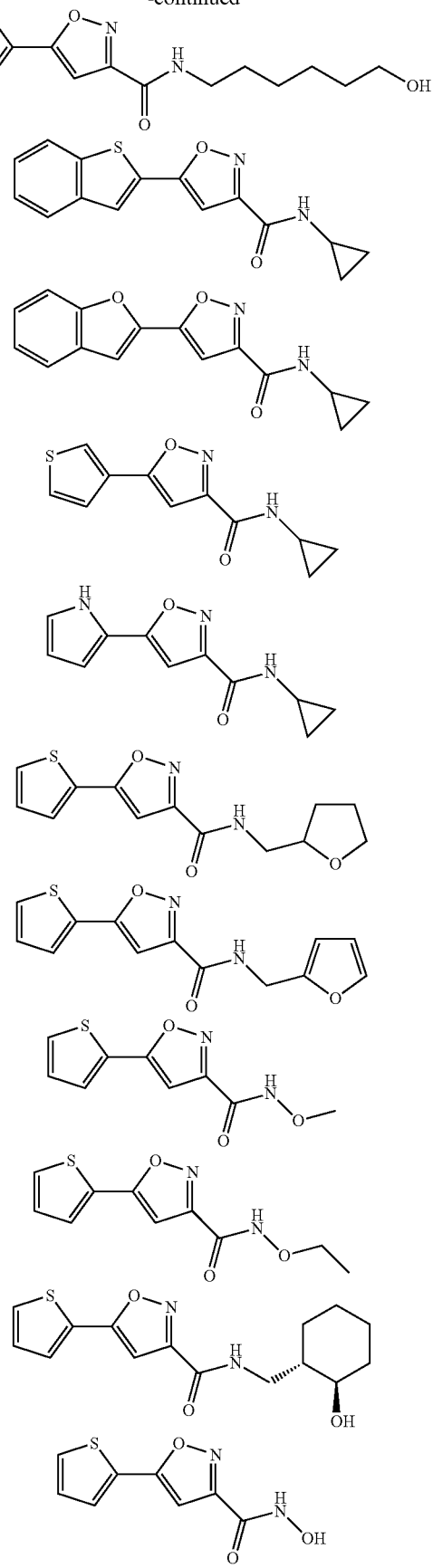

17
-continued
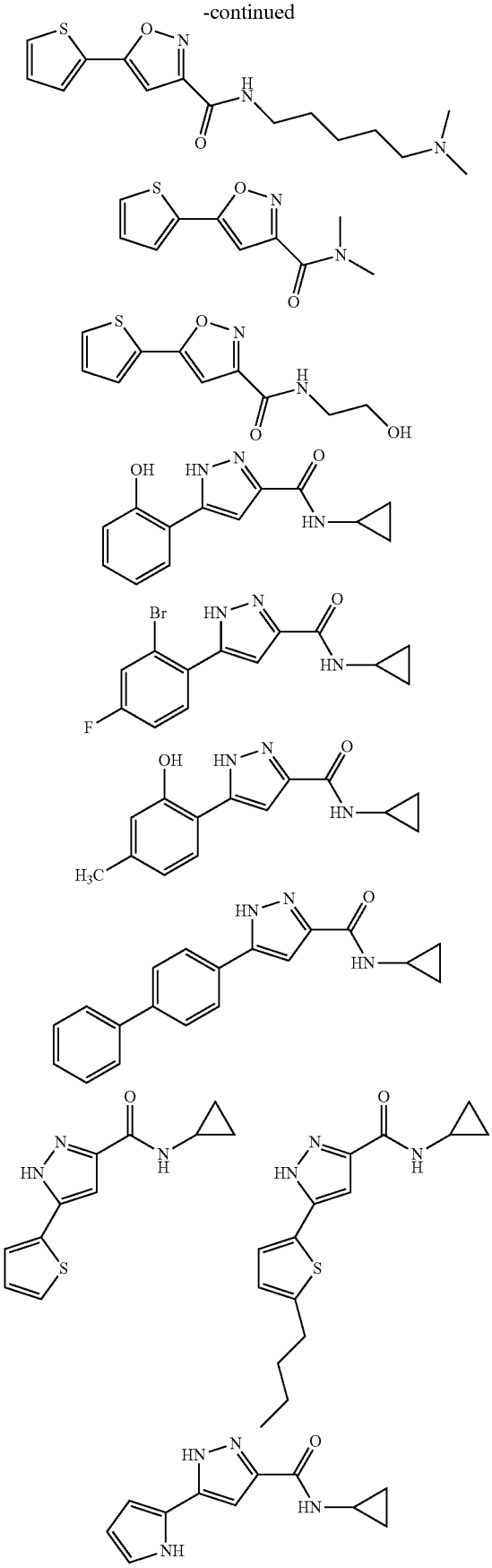
18
-continued
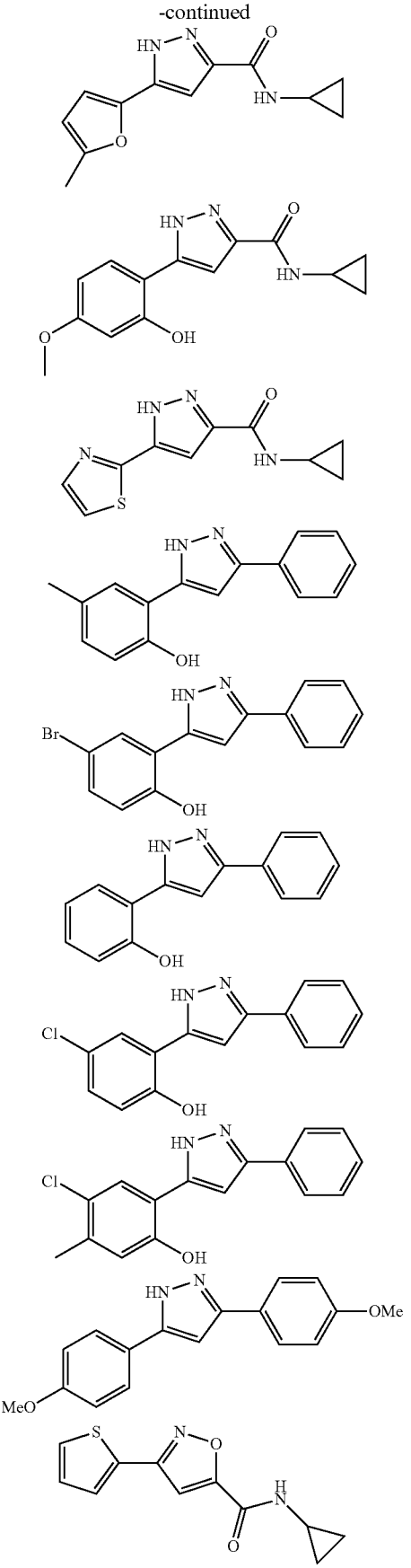

-continued

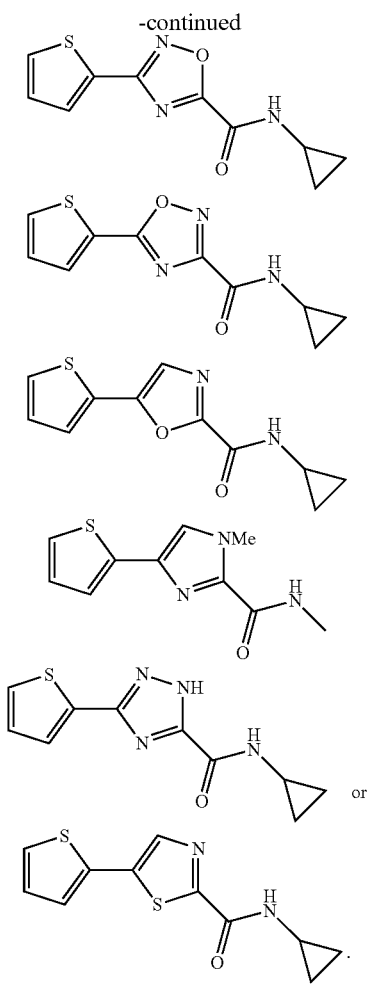

In particular embodiments, a compound of formula (V) is not any one or more of the following compounds:

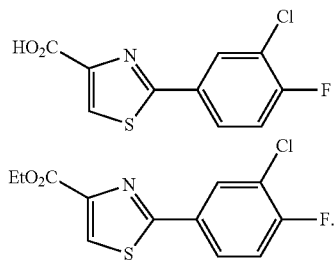

Other general aspects of the present invention contemplate a method of treating a brain tumor comprising administrating to a patient a compound of the present invention, such as a compound of formula (I), (Ia), (Ib), (Ic), (II) or (V). The brain tumor may be of any type known to those of skill in the art. For example, the brain tumor may be selected from the group consisting of a glioma, a glioblastoma, an astrocytoma, an oligodendroglioma, an ependymoma, a meningioma, or a medulloblastoma. In certain embodiments, the brain tumor is glioblastoma multiforme, anaplastic astrocytoma, infiltrative astrocytoma, pilocytic astrocytoma, mixed oligoastrocytoma, or mixed glioma. In treating a patient with a brain tumor, a compound of the present invention (e.g., a compound of formula (I), (Ia), (Ib), (Ic), (II) or (V)) is administered intratumorally. Methods of treatment as described herein may further comprise resection of the brain tumor. A compound of the present invention (e.g., a compound of formula (I), (Ia), (Ib), (Ic), (II) or (V)) may be administered before or after such resection. For example, after a tumor has been resected, a compound of the present invention may be administered, wherein such administration comprises administration to the tumor bed.

The terms "contacted" and "exposed," when applied to a cell, are used herein to describe the process by which a compound of the invention is delivered to a target cell or is placed in direct juxtaposition with the target cell.

The term "effective," as that term is used in the specification and/or claims (e.g., "an effective amount," means adequate to accomplish a desired, expected, or intended result.

"Treatment" and "treating" as used herein refer to administration or application of a therapeutic agent to a subject or performance of a procedure or modality on a subject for the purpose of obtaining a therapeutic benefit of a disease or health-related condition.

The term "therapeutic benefit" or "therapeutically effective" as used throughout this application refers to anything that promotes or enhances the well-being of the subject with respect to the medical treatment of a condition. This includes, but is not limited to, a reduction in the frequency or severity of the signs or symptoms of a disease.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device and/or method being employed to determine the value.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following figures form part of the present specification and are included to further demonstrate certain aspects of the present invention. The invention may be better understood by reference to one or more of these drawings in combination with the detailed description of specific embodiments presented herein.

FIGS. 1A-F—Isx Mediate an Instructive Fate Signal in Uncommitted NSCs and Increase Proliferation of Committed Neuroblasts.

(FIG. 1A) Isx-9 treatment induce at least a 8-fold increase in both neuroD and gluR2-luc reporters, and exceed the gold standard, retinoic acid and forskolin (RA/FSK) in HCN cells (FIG. 1B) Isx-9 promotes robust neuronal differentiation of HCN cells and dominantly blocks gliogenesis in 4 d cultures. Scale bar: 25 µm. Quantification of Tuj1+ cells over 4 d is shown. (FIG. 1C) Synthetic scheme of 3,5-disubstituted isoxazoles. (FIG. 1D) RT-PCR gene expression profiles and protein blotting analysis of neuronal-specific genes and $p27^{KIP1}$ levels in HCN cells. GAPDH is used as a normalization control. (FIG. 1E) Proliferation dynamics in Isx-9-treated cultures. Shown is a representative field of vehicle- or 20 µM Isx-9-treated HCNs. Scale bar: 5 µm. Shown in FIG. 1F is a summary of HCN response to Isx-9 versus vehicle at early (0-48 h) and later timepoints (48-96 h) in terms of proliferation, differentiation, and cell death. Values in FIGS. 1B and 1E represent average of 2 replicates +SD of one representative experiment from three independent experiments.

Figure 2A:
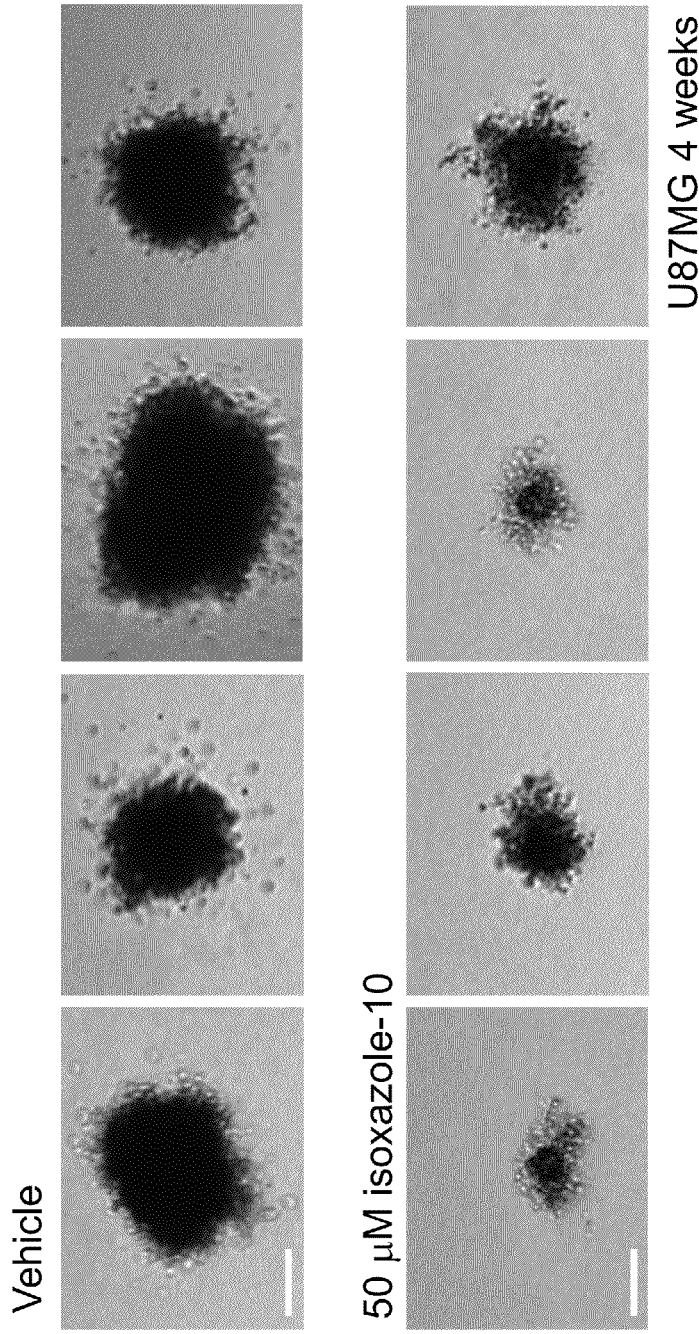
FIGS. 2A-D—Activity of Isoxazoles Isx a Against Brain Cancer Stem Cells.
Figure 2B:
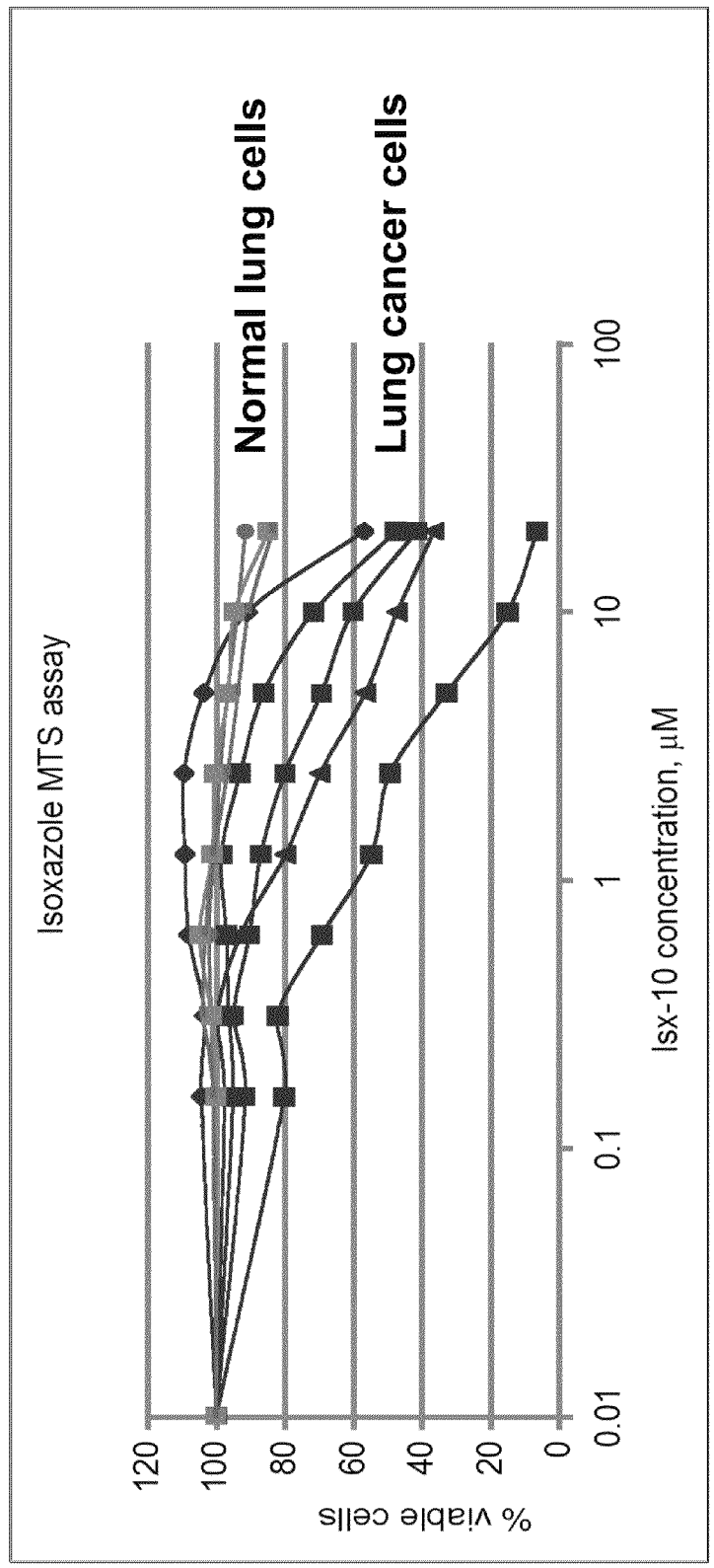
Figure 2C:
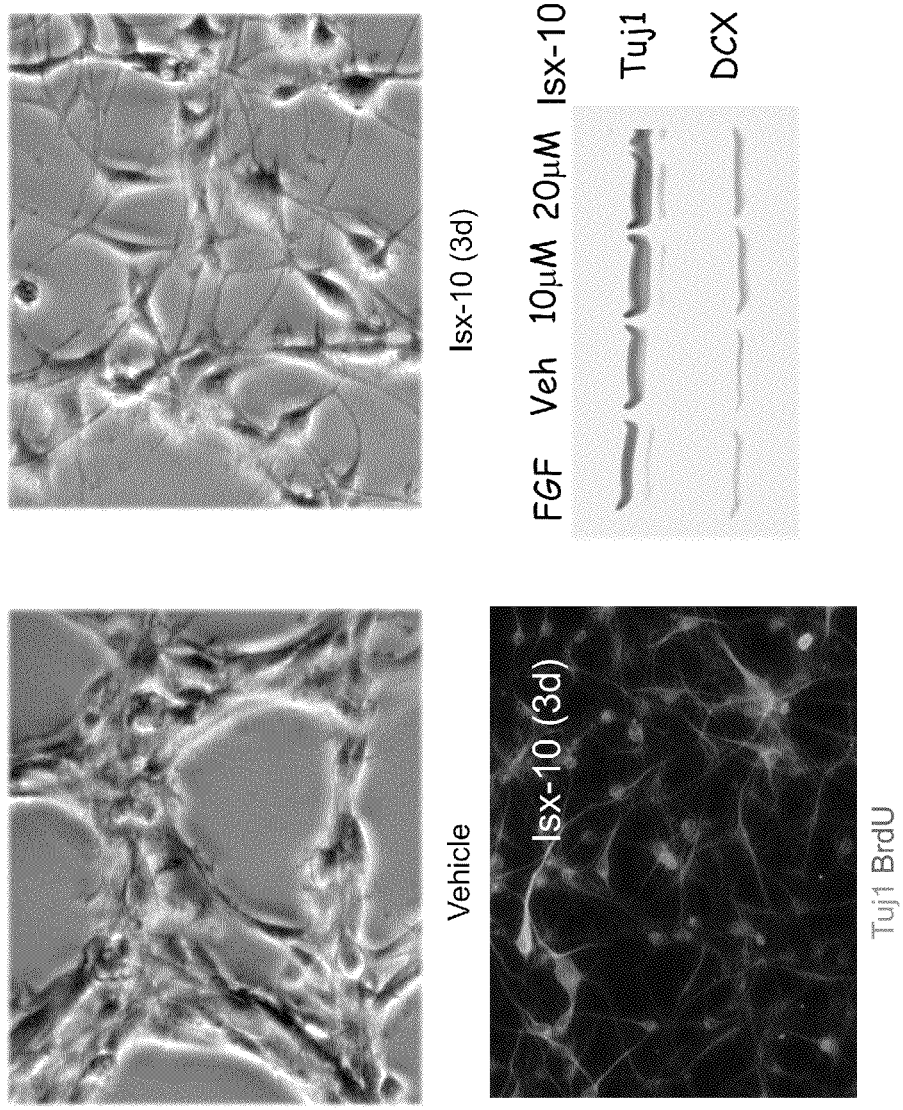
Figure 2D:
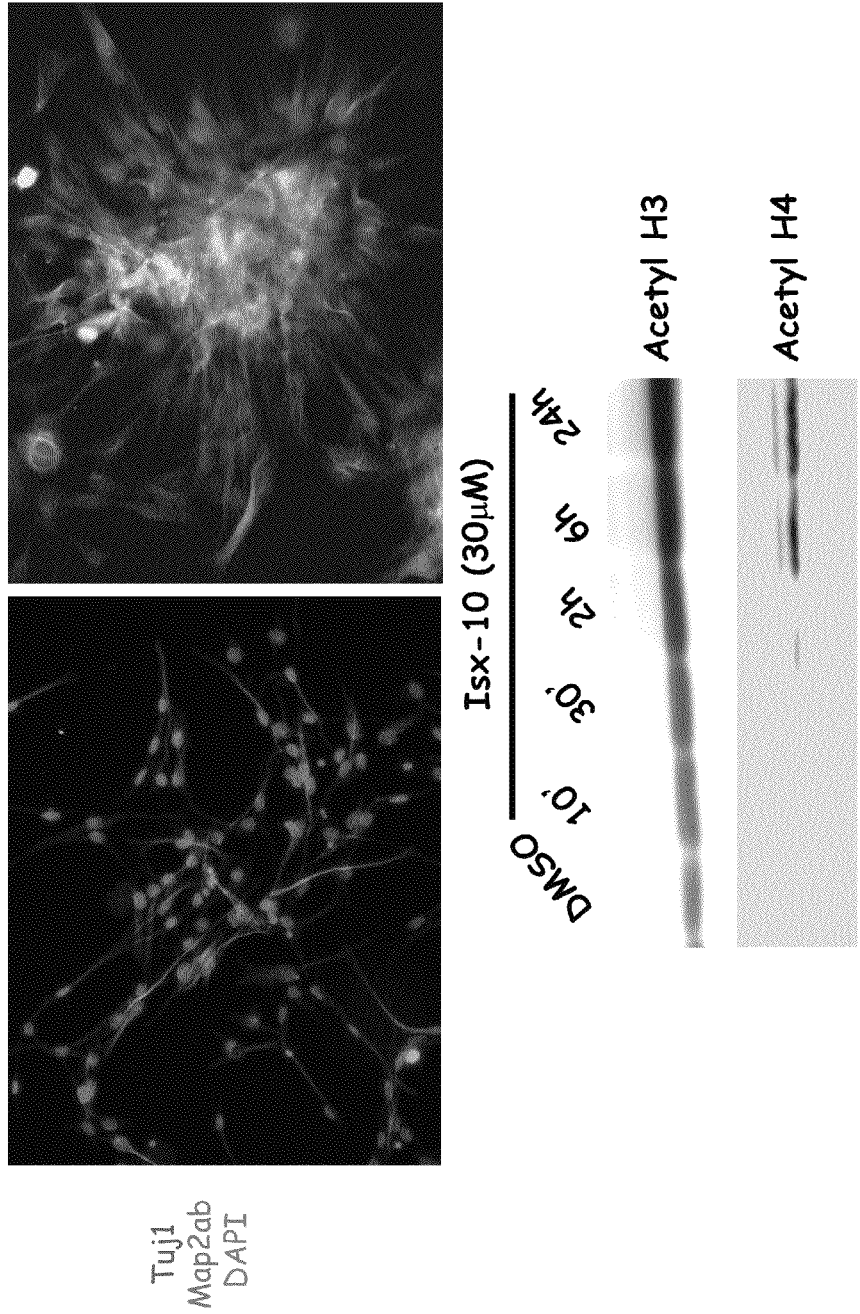

Isx treatment blocks the ability of human glioma cells (U87MG cell line from ATCC) to proliferate and form colonies in soft agar (FIG. 2A) and causes death of lung adenocarcinoma cells from human patients, but not control immortalized bronchial epithelial cells from the same patient (FIG. 2B). Within three days of Isx treatment (30 mM), there are profound morphological changes indicative of neuronal differentiation, confirmed by IHC staining (Tuj1, an early neuronal marker) (green) and protein expression (Tuj1 and DCX, both markers of immature neurons). Isx also blocks the growth of astrocytoma cells, demonstrated by the rarity of BrdU-positive cells (red) in these cultures (FIG. 2C). Finally, Isx rapidly induces chromatin modification (hyperacetylation of histone II3 and II4) within 24 hours in human glioblastoma cancer stem cells, and these changes are associated with marked neuronal differentiation (Map2ab and Tuj1 are two neuronal markers) (FIG. 2D).

FIGS. 3A-C—Isx Activate $Ca^{2+}$ Influx in NSCs.

(FIG. 3A) Representative images showing Fura-2 340/380 ratios in HCN cells. Scale bar: 5 µm. (FIG. 3B) Average 340/380 ratio traces of four representative fields (n=40-50 cells/field) corresponding to Veh—(dark blue), Isx-9—(red), Isx-9/cocktail inhibitor—(light blue), or Isx-9/MK801—(light green) treated HCNs. (FIG. 3C) 50 µM cocktail inhibitor or 100 µM MK801 in Isx-9-treated HCNs attenuated neuroD-luc activity after 24 h. Values represent average of 12 replicates ±SD; *: P=0.0002 and **: P=0.0003, Student's t-test.

FIGS. 4A-F—Isx Signaling Leads to Phosphorylation and Export of HDAC5 and MEF2-Dependent Gene Expression in NSCs.

(FIG. 4A) Dose-dependent activation of a MEF2 reporter gene (3XMRE-luc) in Isx-9-treated HCN cells. (FIG. 4B) MEF2C is up-regulated in Isx-9-treated cultures compared to vehicle controls. (FIG. 4C) Increased HDAC5 phosphorylation over time with Isx-9 treatment, normalized to GAPDH. (FIG. 4D) Accumulation of phospho-HDAC5 in the cytoplasm of 2-d Isx-9 treated HCNs. (FIG. 4E) Shown are representative fields of live-cell GFP fluorescence in vehicle or 20 µM Isx-9-treated HCN cells expressing wild-type GFP-HDAC5 [AdGFP-HD5 (WT)] or 5259/498A mutant GFP-HDAC5 [AdGFP-HDAC5 (S-A)]. Scale bar: 5 µm. Quantification of the percentage of HCN cells showing GFP-HDAC5 localization in nuclear (Nuc), cytoplasmic (Cyto), or both compartments (Nuc/Cyto) is shown. (FIG. 4F) Expression of signal-resistant mutant HDAC5 (SA) and dominant negative MEF2-engrailed repressor fusion protein abrogated Isx-9-mediated activation of the NR1-luc reporter gene, normalized to a control GFP plasmid. Values in FIGS. 4A, 4E and 4F represent the average of 12 replicates +SD.

FIGS. 5A-F—CaMK is the Major HDAC Kinase Activated by Isx Small-Molecules in NSCs.

(FIG. 5A) 5 µM KN93 (CaMK inhibitor) blocked Isx-9-mediated MEF2 reporter activation, while 200 nM G66976 (PKC inhibitor) was completely ineffective. (FIG. 5B) 5 µM KN93 decreased phospho-HDAC5 and active phospho-CaMKII levels in Isx-9-treated NSCs, and (FIG. 5C) MEF2 reporter activity, while 5 µM KN92, an analog of KN93 that blocks potassium channels, had no effect. The doses of KN93 and KN92 in reporter assays were 10, 5, and 1 µM. (FIG. 5D) A schematic diagram of a mammalian 2-hybrid luciferase assay system (pHDAC5:14-3-3-luciferase) which is dependent on the interaction of HDAC5 and 14-3-3. KN93, and not KN92, completely blocked HDAC5 kinase activity in Isx-9-treated NSCs. (FIG. 5E) Shown are representative images and quantification of the percentage of Isx-9-treated HCNs showing GFP-HDAC5 localization in nuclear (Nuc), cytoplasmic (Cyto), or both compartments (Nuc/Cyto) with and without KN93 or KN92 treatment after 24 h. (FIG. 5F) Blocking CaMK with KN93 resulted in an inhibition of Isx-9 neurogenic activity in HCN cells in 2 d cultures. Scale bar: 5 µm. Values in FIGS. 6A, 6C and 6D represent the average of 12 replicates ±SD. Values in FIG. 5E represent the average of 2 replicates +SD of one representative experiment from two independent experiments.

FIGS. 6A-D—Isx are a Novel Class of Neurogenic Small-Molecules.

(FIG. 6A) Select 3,5-disubstituted isoxazoles obtained from the primary high throughput screen (Sadek et al., manuscript submitted) and assayed for neuroD-luc activity in P19CL6 or HCN cells. Values represent the average of 12 replicates +SD. (FIG. 6B) Initial 5 hits from the primary screen and select analogs from secondary structure activity relationship (SAR) studies. (FIG. 6C) Isx-9 promotes maximum Tuj1+ differentiation (>50% by 4 d) in HCN cells. This was confirmed by increased Tuj1 protein (βIIITub) and decreased expression of NSC-enriched transcription factor, SOX2. (FIG. 6D) Activation of neuroD-luc in HCNs treated with various Isx for 24 h. All Isx were 20 µM, unless otherwise noted.

FIGS. 7A-C—Isx is a Neurogenic Small-Molecule in a Variety of Stem Cells.

(FIG. 7A) Blocking cell death with the caspase inhibitor Q-VD-Oph does not further increase Tuj1+ cells in 20 Isx-9-treated HCNs, suggesting that selective effects on survival of pre-committed progenitors is not a major contribution to the net increased neurogenesis. (FIG. 7B) Confirmation that 2 µM Q-VD-Oph blocks cell death in Isx-9-treated HCNs. (FIG. 7C) Isx-9 promotes neuronal differentiation in adult mouse whole brain (MWB) neural progenitor cells and P19CL6 cells in 4 d cultures. Scale bar: 25 and 50 µm, respectively. Values in FIGS. 7A and 7B represent average of 2 replicates +SD of one representative experiment from three independent experiments.

FIGS. 8A-C—Epigenetic Regulation of MEF2 Activity Triggered by Isx-9 in NSCs.

(FIG. 8A) Protein blotting time-course analysis of MEF2 isoforms revealed that MEF2A and MEF2C levels are unchanged with Isx-9-induced neurogenesis. GAPDH served as a normalization control. (FIG. 8B) Total MEF2 binding to MEF2 response element within the NR1 gene is similar between Isx-9-treated HCN cells versus vehicle-treated cells. (FIG. 8C) Confirmation of cytoplasmic enrichment of phospho-HDAC5 by immunoprecipitating/protein blotting of nuclear and cytoplasmic extracts in control (Veh) and Isx-9-treated HCN cells infected with wild-type Flag-HDAC5 for 2 d. NSC lysates were immunoprecipitated with the Flag antibody and blotted with phospho-specific HDAC5 and Flag antibodies. CREB and GFP served as normalization controls.

FIGS. 9A-H—Isoxazoles Specifically Target the CD133(+) Glioblastoma Cancer Stem Cell to Adopt a Neuronal Fate Program.

Isx-9 triggers a pro neuronal-differentiation effect on human CD133(+) brain tumor stem cells (BTSCs) within 4 days. (FIG. 9A) Relative to growth factors alone (20 ng/ml FGF/EGF), (FIG. 9C) Isx-9 treatment (20 μM) leads to more differentiated (adherent and phase-dark with neuronal-like processes) cells. (FIG. 9B) BTSCs cultured with DMSO (vehicle) (1% vol./vol.). (FIG. 9D) Isx-9-treated BTSCs stained with neuronal markers Tuj1 (red) and Map2ab (green), Dapi-stained nuclei is blue. Scale bar=25 μm. (FIG. 9E) Dose-dependent activation of two neuron-specific reporter genes, NeuroD- and (FIG. 9F) NMDA receptor 1-(NR1) luciferase (luc) in Isx-9-treated BTSCs compared to vehicle control after 24 hours. An unrelated class of small-molecules (sulfonyl hydrazone, Shz) did not significantly induce reporter gene activity. (FIGS. 9G and 9H) RT-PCR and protein blotting analysis of gene expression in Isx-9-treated BTSCs. (FIG. 9G) Up-regulation of NeuroD in BTSCs treated with Isx-9 for 2 days which remains elevated when FGF/EGF is added back (without Isx-9) for another 2 days. The Kruppel-family zinc finger transcriptional regulator and proto-oncogene neuron-restrictive silencer factor (NRSF) and CD133 are both down-regulated with Isx-treatment. (FIG. 9H)NRSF protein is downregulated with longer Isx-9 timepoints, compared to the chromatin-remodeling enzymes histone deacetylases (HDAC)-4 and -5, which remain relatively unchanged. GAPDH is used as a normalization control. Despite a dramatic change in cell morphology and attachment mediated by Isx-9 treatment, overall levels of neuronal proteins, such as βTujIII and glutamate receptor 2 (GluR2) do not significantly differ between control and Isx-9-treated BTSCs.

Figure 10:
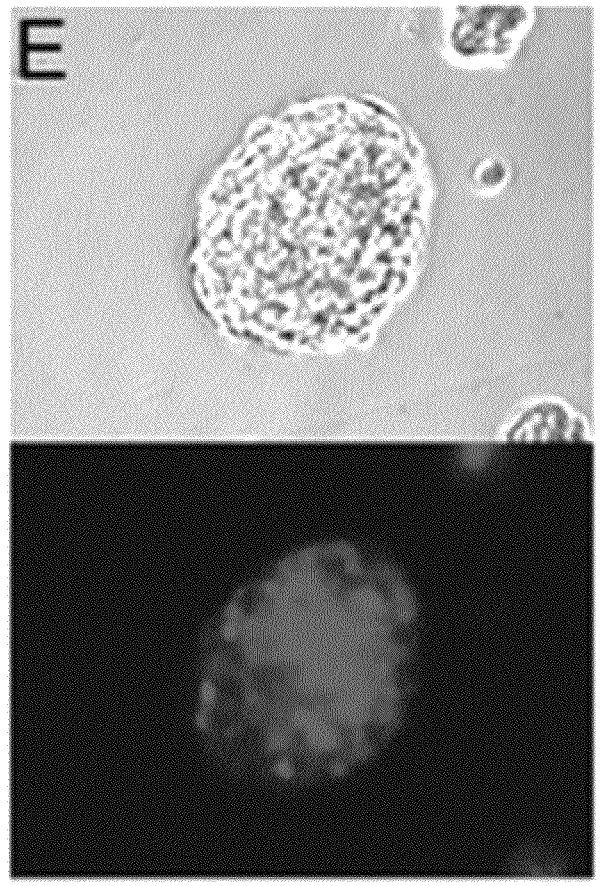
Figure 10:
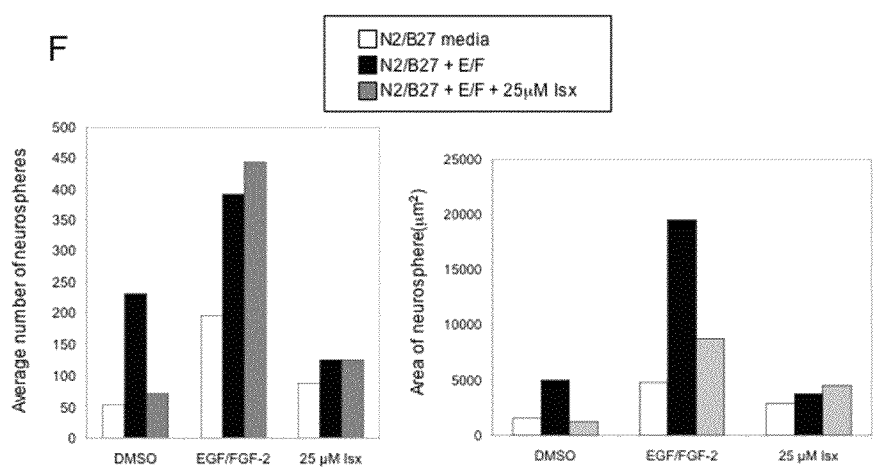
Figure 10:
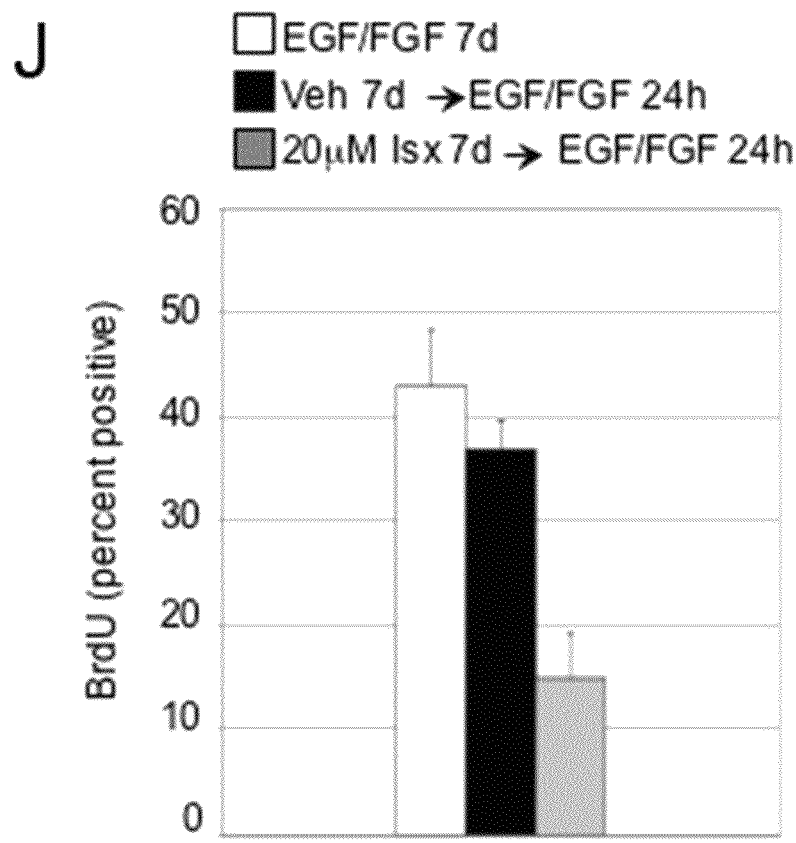

FIGS. 10A-N—Isoxazoles Induce Growth Arrest and Inhibit the Tumorigenic Potential of Human BTSCs In Vitro and In Vivo.

(FIG. 10A-E) Phase-bright images of brain tumor stem cells (BTSCs) treated with EGF/FGF (FIG. 10A) or Isx-9 (FIG. 10B) for 7 days before returning to EGF/FGF (FIG. 10C) or EGF/FGF plus Isx-9 conditions (FIG. 10D) for an additional 2 days. (FIG. 10E) BTSCs labeled with CAG-red fluorescent protein (RFP) in vitro. (FIG. 10F) 7-day pretreatment of BTSCs with DMSO (vehicle), EGF/FGF, or Isx-9, dissociated and re-plated to form secondary neurospheres (1000 cells/well) under various conditions [N2/B27 media alone (white bars), N2/B27 plus EGF/FGF (black bars), and N2/B27 plus EGF/FGF plus Isx-9 (gray bars)] for 7 additional days. Shown in FIG. 10F is a graphical representation of the average number of neurospheres (per 3 wells) and the average area of each neurosphere ($\mu m^2$). (FIGS. 10G-J) Isx-9 pre-treatment for 7 days leads to decreased DNA synthesis/proliferation (BrdU uptake with a 1 hour pulse prior to fixation) compared to EGF/FGF or vehicle pre-treatment, even when EGF/FGF is added back for 24 hours. (FIGS. 10G-I) BrdU staining in fixed cultures; BrdU (red) and Dapi-stained nuclei (blue). (FIG. 10J) Graphical representation of the percent of BrdU(+) cells (out of the total Dapi(+) cells). (FIGS. 10K-N) 7-day exposure of RFP-labeled human CD133(+) BTSCs to 20 ng/ml EGF/FGF (FIGS. 10K and 10L) or Isx-9 (20 μM) (FIGS. 10M and 10N) in vitro, before transplantation into the striatum of NOD/scid mice, dramatically reduces tumor-initiating ability. Scale bar=200 μm.

Figure 11:
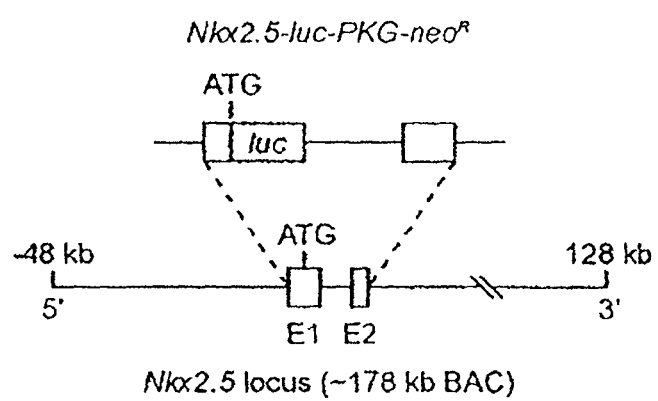

FIG. 11—Schematic of Reporter Transgene with Luciferase Inserted by Homologous Recombination into the Nkx2.5 Locus on an ~178 Kb Mouse BAC.

FIG. 12A-I—Results of Neuronal Differentiation Induction by Various Compounds of the Present Invention (See Example 4).

DESCRIPTION OF ILLUSTRATIVE EMBODIMENTS

The present invention overcomes the deficiencies of the prior art by providing compounds that induce neuronal differentiation and methods relating thereto.

Increasing clinical success of stem cell therapy for neuronal regeneration purposes and addressing neurological problems is coupled to the need for better understanding of neural cell fate mechanisms. Here, the inventors report the identification of small-molecules involved in neuronal fate by screening a chemical library for activators of the signature gene, Nkx2.5, using a luciferase knock-in bacterial artificial chromosome (BAC) in mouse P 19CL6 pluripotent stem cells. This family of isoxazole-derived small molecules can be used to trigger neuronal mRNA and protein expression in a variety of embryonic and adult stem/progenitor cells (NSCs). Small-molecule enhanced NSCs engrafted into the brain or spinal cord may assist with the recovery of neuronal function following injury or disease. Isoxazoles and their derivatives are thus promising drugs to promote neuronal repair/regeneration by activating neuronal differentiation in stem cells.

Over the past several years the concept of cancer stem cells has been extended from hematological malignancies to epithelial cancers including gliomas. Although the mechanistic understanding of cancer stem cells remains limited, the concept raises fundamental issues about the cellular origins of cancer as well as tumor progression and maintenance, and therefore has important implications for the development of therapeutics. At its core, the cancer stem cell hypothesis proposes that a small (<1-5%) fraction of the tumor cells are exclusively responsible for maintaining tumor burden and represent the most recalcitrant cell types to conventional radiotherapy and chemotherapy. The clear implications are that effective cancer therapies must be able to target and destroy the cancer stem cells. Discovery of this isoxazole-based small molecule family provides both an important mechanistic clue to the cancer stem cell hypothesis as it applies to gliomas, and provides for development of novel chemotherapeutic agents that can specifically target cancer stem cells.

These, and other aspects of the invention, are set out in detail below.

B. COMPOUNDS OF THE PRESENT INVENTION

Compounds of the present invention may be considered as derived from isoxazoles. The following compounds are representative of certain compounds of the present invention:

a compound of formula (I):

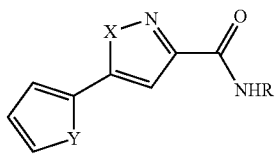

wherein X is O or NH, Y is S or O and R is H, a substituted or unsubstituted alkyl, such as $C_1$-$C_6$alkyl or $C_3$-$C_6$cycloalkyl, or a substituted or unsubstituted alkenyl, such as $C_2$-$C_6$alkenyl, a substituted or unsubstituted alkenyl, such as $C_2$-$C_6$alkynyl, or a stereoisomer, solvate, hydrate, or pharmaceutically acceptable salt thereof. In certain embodiments regarding compounds of formula (I), the proviso exists such that with the provisos that if X is O, then R must be a substituted or unsubstituted $C_3$-$C_6$cycloalkyl; and/or if X is NH, then R must not be pyrazinyl substituted $C_1$-$C_6$alkyl;

a compound of formula (Ia), (Ib), or (Ic):

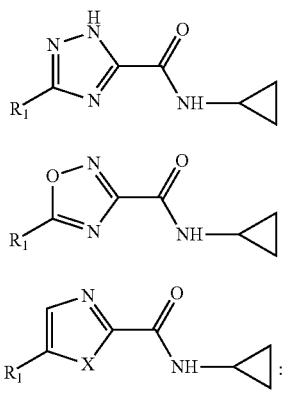

wherein $R_1$ is substituted or unsubstituted phenyl, unsubstituted pyrrolyl, unsubstituted pyridyl, unsubstituted furanyl, unsubstituted thienyl, unsubstituted benzofuranyl, unsubstituted benzo[b]thiophenyl, or unsubstituted thiazolyl. Any of these R1 substituents may be substituted as well;

a compound of formula (II):

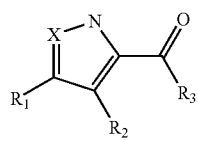

wherein: $R_1$ is substituted or unsubstituted thiophenyl or a substituent of formula (A):

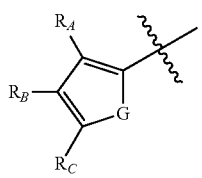

wherein: $R_A$, $R_B$ and $R_C$ are each independently selected from the group consisting of hydrogen, halogen, $C_1$-$C_6$alkyl, $C_3$-$C_6$cycloalkyl, aryl, cyano, nitro, and a carbonyl group; and G is O, —NH, or S; $R_2$ is hydrogen, hydroxy, halogen, nitro, aryl, alkyl, alkoxy, alkenyl, alkenyloxy, alkynyl, alkynyloxy, aralkyl, —CHO, —C(O)$R_9$, —OC(O)$R_9$, —OC(O)OR$_9$, —O(CN)OR$_9$, —C(O)NR$_9$R$_{10}$, —OC(O)NR$_9$R$_{10}$, —NR$_9$OR$_5$, or —SO$_3$R$_9$; wherein $R_9$ and $R_{10}$ are each independently hydrogen, alkyl, aryl, or aralkyl; $R_3$ is —NH—O-alkyl, —NH—OH, —OR$^1$ or —NR$_{11}$R$_{12}$, wherein $R_{11}$ and $R_{12}$ are each independently hydrogen, alkyl, alkenyl, alkynyl, aryl, or aralkyl; or $R_{11}$ and $R_{12}$ together form a cyclic group; or $R_{11}$ and $R_{12}$ together with the nitrogen to which they are bound form a cyclic group; X is O or —NR$_{13}$, wherein $R_{13}$ is hydrogen, alkyl, aryl, or aralkyl; or a stereoisomer, solvate, hydrate, or pharmaceutically acceptable salt thereof;

and a compound having formula (V):

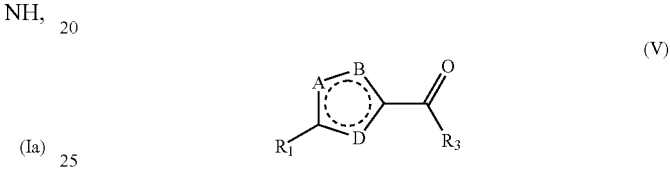

wherein: the ABD ring comprises two non-adjacent double bonds; A, B and D are each independently S, N, O, C, —NR$_{14}$, —CR$_{15}$, or —CR$_{15}$R$_{16}$, wherein $R_{14}$ is hydrogen, halogen, alkyl, aryl, or aralkyl; and $R_{15}$ and $R_{16}$ are each independently hydrogen, hydroxy, halogen, nitro, aryl, alkyl, alkoxy, alkenyl, alkenyloxy, alkynyl, alkynyloxy, aralkyl, —CHO, —C(O)$R_9$, —OC(O)$R_9$, —OC(O)OR$_9$, —O(CN)OR$_9$, —C(O)NR$_9$R$_{10}$, —OC(O)NR$_9$R$_{10}$, —NR$_9$OR$_5$, or —SO$_3$R$_9$; wherein $R_9$ and $R_{10}$ are each independently hydrogen, alkyl, aryl, or aralkyl, provided that at least two of A, B and D comprise S, N, or O; $R_1$ is alkyl, —CH═CH-aryl, or aryl; and $R_3$ is alkyl, aryl, aralkyl, —OR$_4$, or —NR$_4$R$_5$, wherein: $R_4$ and $R_5$ are each independently hydrogen, alkyl, aryl, or aralkyl; or $R_4$ and $R_5$ together form a cyclic group; or $R_4$ and $R_5$ together with the nitrogen to which they are bound form a cyclic group. In certain embodiments regarding compounds of formula (V), the proviso exists such that compounds of formula (V$_a$) are excluded:

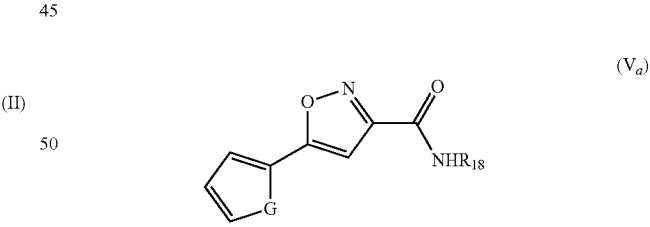

wherein $R_{18}$ is alkyl, such as lower alkyl or cyclopentyl, or alkenyl, such as lower alkenyl or allyl, and G is O or S.

C. CHEMICAL DEFINITIONS

As used herein, the term "amino" means —NH$_2$; the term "nitro" means —NO$_2$; the term "halo" designates —F, —Cl, —Br or —I; the term "mercapto" or "thiol" means —SH; the term "cyano" means —CN; the term "azido" means —N$_3$; the term "silyl" means —SiH$_3$, and the term "hydroxy" means —OH.

The term "alkyl" includes straight-chain alkyl, branched-chain alkyl, cycloalkyl (alicyclic), cyclic alkyl, heteroatom-unsubstituted alkyl, heteroatom-substituted alkyl, heteroatom-unsubstituted $C_n$-alkyl, and heteroatom-substituted $C_n$-alkyl. In certain embodiments, lower alkyls are contemplated. The term "lower alkyl" refers to alkyls of 1-6 carbon atoms (that is, 1, 2, 3, 4, 5 or 6 carbon atoms). Higher alkyls are contemplated in certain embodiments. The term "higher alkyl" refers to alkyls of 6 carbon atoms or higher, such as 6-15 carbon atoms. The term "heteroatom-unsubstituted $C_n$-alkyl" refers to a radical, having a linear or branched, cyclic or acyclic structure, further having no carbon-carbon double or triple bonds, further having a total of n carbon atoms, all of which are nonaromatic, 3 or more hydrogen atoms, and no heteroatoms. For example, a heteroatom-unsubstituted $C_1$-$C_{10}$-alkyl has 1 to 10 carbon atoms. The groups, —$CH_3$ (Me), —$CH_2CH_3$ (Et), —$CH_2CH_2CH_3$ (n-Pr), —$CH(CH_3)_2$ (iso-Pr), —$CH(CH_2)_2$ (cyclopropyl), —$CH_2CH_2CH_2CH_3$ (n-Bu), —$CH(CH_3)CH_2CH_3$ (sec-butyl), —$CH_2CH(CH_3)_2$ (iso-butyl), —$C(CH_3)_3$ (text-butyl), —$CH_2C(CH_3)_3$ (neopentyl), cyclobutyl, cyclopentyl, and cyclohexyl, are all non-limiting examples of heteroatom-unsubstituted alkyl groups. The term "heteroatom-substituted $C_n$-alkyl" refers to a radical, having a single saturated carbon atom as the point of attachment, no carbon-carbon double or triple bonds, further having a linear or branched, cyclic or acyclic structure, further having a total of n carbon atoms, all of which are non-aromatic, 0, 1, or more than one hydrogen atom, at least one heteroatom, wherein each heteroatom is independently selected from the group consisting of N, O, F, Cl, Br, I, Si, P, and S. For example, a heteroatom-substituted $C_1$-$C_{10}$-alkyl has 1 to 10 carbon atoms. The following groups are all non-limiting examples of heteroatom-substituted alkyl groups: trifluoromethyl, —$CH_2F$, —$CH_2Cl$, —$CH_2Br$, —$CH_2OH$, —$CH_2OCH_3$, —$CH_2OCH_2CF_3$, —$CH_2OC(O)CH_3$, —$CH_2NH_2$, —$CH_2NHCH_3$, —$CH_2N(CH_3)_2$, —$CH_2CH_2Cl$, —$CH_2CH_2OH$, $CH_2CH_2OC(O)CH_3$, —$CH_2CH_2NHCO_2C(CH_3)_3$, and —$CH_2Si(CH_3)_3$. The term "cycloalkyl" refers to, e.g., cyclopropyl, cyclopentyl, cyclohexyl, etc., as well as heteroatom-substituted cycloalkyl (e.g., pyrrolidinyl, cyclohexanol). The term "alkyl" refers also to a straight- or branched-chain alkyl group that terminates in a cycloalkyl group.

The term "alkenyl" includes straight-chain alkenyl, branched-chain alkenyl, cycloalkenyl, cyclic alkenyl, heteroatom-unsubstituted alkenyl, heteroatom-substituted alkenyl, heteroatom-unsubstituted $C_n$-alkenyl, and heteroatom-substituted $C_n$-alkenyl. In certain embodiments, lower alkenyls are contemplated. The term "lower alkenyl" refers to alkenyls of 1-6 carbon atoms (that is, 1, 2, 3, 4, 5 or 6 carbon atoms). The term "heteroatom-unsubstituted $C_n$-alkenyl" refers to a radical, having a linear or branched, cyclic or acyclic structure, further having at least one nonaromatic carbon-carbon double bond, but no carbon-carbon triple bonds, a total of n carbon atoms, three or more hydrogen atoms, and no heteroatoms. For example, a heteroatom-unsubstituted $C_2$-$C_{10}$-alkenyl has 2 to 10 carbon atoms. Heteroatom-unsubstituted alkenyl groups include: —$CH=CH_2$ (vinyl), —$CH=CHCH_3$, —$CH=CHCH_2CH_3$, —$CH_2CH=CH_2$ (allyl), —$CH_2CH=CHCH_3$, and —$CH=CH$—$C_6H_5$. The term "heteroatom-substituted $C_n$-alkenyl" refers to a radical, having a single nonaromatic carbon atom as the point of attachment and at least one nonaromatic carbon-carbon double bond, but no carbon-carbon triple bonds, further having a linear or branched, cyclic or acyclic structure, further having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted $C_2$-$C_{10}$-alkenyl has 2 to 10 carbon atoms. The groups, —$CH=CHF$, —$CH=CHCl$ and —$CH=CHBr$, are non-limiting examples of heteroatom-substituted alkenyl groups.

The term "alkynyl" includes straight-chain alkynyl, branched-chain alkynyl, cycloalkynyl, cyclic alkynyl, heteroatom-unsubstituted alkynyl, heteroatom-substituted alkynyl, heteroatom-unsubstituted $C_n$-alkynyl, and heteroatom-substituted $C_n$-alkynyl. In certain embodiments, lower alkynyls are contemplated. The term "lower alkynyl" refers to alkynyls of 1-6 carbon atoms (that is, 1, 2, 3, 4, 5 or 6 carbon atoms). The term "heteroatom-unsubstituted $C_n$-alkynyl" refers to a radical, having a linear or branched, cyclic or acyclic structure, further having at least one carbon-carbon triple bond, a total of n carbon atoms, at least one hydrogen atom, and no heteroatoms. For example, a heteroatom-unsubstituted $C_2$-$C_{10}$-alkynyl has 2 to 10 carbon atoms. The groups, —$C\equiv CH$, —$C\equiv CCH_3$, and —$C\equiv CC_6H_5$ are non-limiting examples of heteroatom-unsubstituted alkynyl groups. The term "heteroatom-substituted $C_n$-alkynyl" refers to a radical, having a single nonaromatic carbon atom as the point of attachment and at least one carbon-carbon triple bond, further having a linear or branched, cyclic or acyclic structure, and having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted $C_2$-$C_{10}$-alkynyl has 2 to 10 carbon atoms. The group, —$C\equiv CSi(CH_3)_3$, is a non-limiting example of a heteroatom-substituted alkynyl group.

The term "aryl" includes heteroatom-unsubstituted aryl, heteroatom-substituted aryl, heteroatom-unsubstituted $C_n$-aryl, heteroatom-substituted $C_n$-aryl, heteroaryl, heterocyclic aryl groups, carbocyclic aryl groups, biaryl groups, and single-valent radicals derived from polycyclic fused hydrocarbons (PAHs). The term "heteroatom-unsubstituted $C_n$-aryl" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, a heteroatom-unsubstituted $C_6$-$C_{10}$-aryl has 6 to 10 carbon atoms. Non-limiting examples of heteroatom-unsubstituted aryl groups include phenyl (Ph), methylphenyl, (dimethyl)phenyl, —$C_6H_4CH_2CH_3$, —$C_6H_4CH_2CH_2CH_3$, —$C_6H_4CH(CH_3)_2$, —$C_6H_4CH(CH_2)_2$, —$C_6H_3(CH_3)CH_2CH_3$, —$C_6H_4CH=CH_2$, —$C_6H_4CH=CHCH_3$, —$C_6H_4C\equiv CH$, —$C_6H_4C\equiv CCH_3$, naphthyl, and the radical derived from biphenyl. The term "heteroatom-substituted $C_n$-aryl" refers to a radical, having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-unsubstituted $C_1$-$C_{10}$-heteroaryl has 1 to 10 carbon atoms. Non-limiting examples of heteroatom-substituted aryl groups include the groups: —$C_6H_4F$, —$C_6H_4Cl$, —$C_6H_4Br$, —$C_6H_4I$, —$C_6H_4OH$, —$C_6H_4OCH_3$, —$C_6H_4OCH_2CH_3$, —$C_6H_4OC(O)CH_3$, —$C_6H_4NH_2$, —$C_6H_4NHCH_3$, —$C_6H_4N(CH_3)_2$, —$C_6H_4CH_2OH$, —$C_6H_4CH_2OC(O)CH_3$, —$C_6H_4CH_2NH_2$, —$C_6H_4CF_3$, —$C_6H_4CN$, —$C_6H_4CHO$, —$C_6H_4CHO$, —$C_6H_4C(O)CH_3$, —$C_6H_4C(O)C_6H_5$, —$C_6H_4CO_2H$, —$C_6H_4CO_2CH_3$, —$C_6H_4CONH_2$, —$C_6H_4CONHCH_3$, —$C_6H_4CON(CH_3)_2$, furanyl, thienyl, pyridyl, pyrrolyl, pyrimidyl, pyrazinyl, quinolyl, indolyl, and imidazoyl.

The term "aralkyl" includes heteroatom-unsubstituted aralkyl, heteroatom-substituted aralkyl, heteroatom-unsubstituted $C_n$-aralkyl, heteroatom-substituted $C_n$-aralkyl, heteroaralkyl, and heterocyclic aralkyl groups. In certain embodiments, lower aralkyls are contemplated. The term "lower aralkyl" refers to aralkyls of 7-12 carbon atoms (that is, 7, 8, 9, 10, 11 or 12 carbon atoms). The term "heteroatom-unsubstituted $C_n$-aralkyl" refers to a radical, having a single saturated carbon atom as the point of attachment, further having a total of n carbon atoms, wherein at least 6 of the carbon atoms form an aromatic ring structure containing only carbon atoms, 7 or more hydrogen atoms, and no heteroatoms. For example, a heteroatom-unsubstituted $C_7$-$C_{10}$-aralkyl has 7 to 10 carbon atoms. Non-limiting examples of heteroatom-unsubstituted aralkyls are: phenylmethyl (benzyl, Bn) and phenylethyl. The term "heteroatom-substituted $C_n$-aralkyl" refers to a radical, having a single saturated carbon atom as the point of attachment, further having a total of n carbon atoms, 0, 1, or more than one hydrogen atom, and at least one heteroatom, wherein at least one of the carbon atoms is incorporated an aromatic ring structures, further wherein each heteroatom is independently selected from the group consisting of N, O, F, Cl, Br, I, Si, P, and S. For example, a heteroatom-substituted $C_2$-$C_{10}$-heteroaralkyl has 2 to 10 carbon atoms.

The term "acyl" includes straight-chain acyl, branched-chain acyl, cycloacyl, cyclic acyl, heteroatom-unsubstituted acyl, heteroatom-substituted acyl, heteroatom-unsubstituted $C_n$-acyl, heteroatom-substituted $C_n$-acyl, alkylcarbonyl, alkoxycarbonyl and aminocarbonyl groups. In certain embodiments, lower acyls are contemplated. The term "lower acyl" refers to acyls of 1-6 carbon atoms (that is, 1, 2, 3, 4, 5 or 6 carbon atoms). The term "heteroatom-unsubstituted $C_n$-acyl" refers to a radical, having a single carbon atom of a carbonyl group as the point of attachment, further having a linear or branched, cyclic or acyclic structure, further having a total of n carbon atoms, 1 or more hydrogen atoms, a total of one oxygen atom, and no additional heteroatoms. For example, a heteroatom-unsubstituted $C_1$-$C_{10}$-acyl has 1 to 10 carbon atoms. The groups, —CHO, —C(O)CH$_3$, —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)C$_6$H$_4$CH$_2$CH$_3$, and —COC$_6$H$_3$(CH$_3$)$_2$, are non-limiting examples of heteroatom-unsubstituted acyl groups. The term "heteroatom-substituted $C_n$-acyl" refers to a radical, having a single carbon atom as the point of attachment, the carbon atom being part of a carbonyl group, further having a linear or branched, cyclic or acyclic structure, further having a total of n carbon atoms, 0, 1, or more than one hydrogen atom, at least one additional heteroatom, in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-acyl has 1 to 10 carbon atoms. The groups, —C(O)CH$_2$CF$_3$, —CO$_2$H, —CO$_2$CH$_3$, —CO$_2$CH$_2$CH$_3$, —CO$_2$CH$_2$CH$_2$CH$_3$, —CO$_2$CH(CH$_3$)$_2$, —CO$_2$CH(CH$_2$)$_2$, —C(O)NH$_2$ (carbamoyl), —C(O)NHCH$_3$, —C(O)NHCH$_2$CH$_3$, —CONHCH(CH$_3$)$_2$, —CONHCH(CH$_2$)$_2$, —CON(CH$_3$)$_2$, and —CONHCH$_2$CF$_3$, are non-limiting examples of heteroatom-substituted acyl groups.

The term "alkoxy" includes straight-chain alkoxy, branched-chain alkoxy, cycloalkoxy, cyclic alkoxy, heteroatom-unsubstituted alkoxy, heteroatom-substituted alkoxy, heteroatom-unsubstituted $C_n$-alkoxy, and heteroatom-substituted $C_n$-alkoxy. In certain embodiments, lower alkoxys are contemplated. The term "lower alkoxy" refers to alkoxys of 1-6 carbon atoms (that is, 1, 2, 3, 4, 5 or 6 carbon atoms). The term "heteroatom-unsubstituted $C_n$-alkoxy" refers to a group, having the structure —OR, in which R is a heteroatom-unsubstituted $C_n$-alkyl, as that term is defined above. Heteroatom-unsubstituted alkoxy groups include: —OCH$_3$, —OCH$_2$CH$_3$, —OCH$_2$CH$_2$CH$_3$, —OCH(CH$_3$)$_2$, and —OCH(CH$_2$)$_2$. The term "heteroatom-substituted $C_n$-alkoxy" refers to a group, having the structure —OR, in which R is a heteroatom-substituted $C_n$-alkyl, as that term is defined above. For example, —OCH$_2$CF$_3$ is a heteroatom-substituted alkoxy group.

The term "alkenyloxy" includes straight-chain alkenyloxy, branched-chain alkenyloxy, cycloalkenyloxy, cyclic alkenyloxy, heteroatom-unsubstituted alkenyloxy, heteroatom-substituted alkenyloxy, heteroatom-unsubstituted $C_n$-alkenyloxy, and heteroatom-substituted $C_n$-alkenyloxy. In certain embodiments, lower alkenyloxys are contemplated. The term "lower alkenyloxy" refers to alkenyloxys of 1-6 carbon atoms (that is, 1, 2, 3, 4, 5 or 6 carbon atoms). The term "heteroatom-unsubstituted $C_n$-alkenyloxy" refers to a group, having the structure —OR, in which R is a heteroatom-unsubstituted $C_n$-alkenyl, as that term is defined above. The term "heteroatom-substituted $C_n$-alkenyloxy" refers to a group, having the structure —OR, in which R is a heteroatom-substituted $C_n$-alkenyl, as that term is defined above.

The term "alkynyloxy" includes straight-chain alkynyloxy, branched-chain alkynyloxy, cycloalkynyloxy, cyclic alkynyloxy, heteroatom-unsubstituted alkynyloxy, heteroatom-substituted alkynyloxy, heteroatom-unsubstituted $C_n$-alkynyloxy, and heteroatom-substituted $C_n$-alkynyloxy. In certain embodiments, lower alkynyloxys are contemplated. The term "lower alkynyloxy" refers to alkynyloxys of 1-6 carbon atoms (that is, 1, 2, 3, 4, 5 or 6 carbon atoms). The term "heteroatom-unsubstituted $C_n$-alkynyloxy" refers to a group, having the structure —OR, in which R is a heteroatom-unsubstituted $C_n$-alkynyl, as that term is defined above. The term "heteroatom-substituted $C_n$-alkynyloxy" refers to a group, having the structure —OR, in which R is a heteroatom-substituted $C_n$-alkynyl, as that term is defined above.

The term "aryloxy" includes heteroatom-unsubstituted aryloxy, heteroatom-substituted aryloxy, heteroatom-unsubstituted $C_n$-aryloxy, heteroatom-substituted $C_n$-aryloxy, heteroaryloxy, and heterocyclic aryloxy groups. The term "heteroatom-unsubstituted $C_n$-aryloxy" refers to a group, having the structure —OAr, in which Ar is a heteroatom-unsubstituted $C_n$-aryl, as that term is defined above. A non-limiting example of a heteroatom-unsubstituted aryloxy group is —OC$_6$H$_5$. The term "heteroatom-substituted $C_n$-aryloxy" refers to a group, having the structure —OAr, in which Ar is a heteroatom-substituted $C_n$-aryl, as that term is defined above.

The term "aralkyloxy" includes heteroatom-unsubstituted aralkyloxy, heteroatom-substituted aralkyloxy, heteroatom-unsubstituted $C_n$-aralkyloxy, heteroatom-substituted $C_n$-aralkyloxy, heteroaralkyloxy, and heterocyclic aralkyloxy groups. In certain embodiments, lower aralkyloxys are contemplated. The term "lower aralkyloxy" refers to alkenyloxys of 7-12 carbon atoms (that is, 7, 8, 9, 10, 11, or 12 carbon atoms). The term "heteroatom-unsubstituted $C_n$-aralkyloxy" refers to a group, having the structure —OAr, in which Ar is a heteroatom-unsubstituted $C_n$-aralkyl, as that term is defined above. The term "heteroatom-substituted $C_n$-aralkyloxy" refers to a group, having the structure —OAr, in which Ar is a heteroatom-substituted $C_n$-aralkyl, as that term is defined above.

The term "acyloxy" includes straight-chain acyloxy, branched-chain acyloxy, cycloacyloxy, cyclic acyloxy, heteroatom-unsubstituted acyloxy, heteroatom-substituted acyloxy, heteroatom-unsubstituted $C_n$-acyloxy, heteroatom-substituted $C_n$-acyloxy, alkylcarbonyloxy, arylcarbonyloxy, alkoxycarbonyloxy, aryloxycarbonyloxy, and carboxylate groups. In certain embodiments, lower acyloxys are contemplated. The term "lower acyloxy" refers to acyloxys of 1-6 carbon atoms (that is, 1, 2, 3, 4, 5 or 6 carbon atoms). The term "heteroatom-unsubstituted $C_n$-acyloxy" refers to a group, having the structure —OAc, in which Ac is a heteroatom-unsubstituted $C_n$-acyl, as that term is defined above. For example, —OC(O)CH$_3$ is a non-limiting example of a heteroatom-unsubstituted acyloxy group. The term "heteroatom-substituted $C_n$-acyloxy" refers to a group, having the structure —OAc, in which Ac is a heteroatom-substituted $C_n$-acyl, as that term is defined above. For example, —OC(O)OCH$_3$ and —OC(O)NHCH$_3$ are non-limiting examples of heteroatom-unsubstituted acyloxy groups.

The term "alkylamino" includes straight-chain alkylamino, branched-chain alkylamino, cycloalkylamino, cyclic alkylamino, heteroatom-unsubstituted alkylamino, heteroatom-substituted alkylamino, heteroatom-unsubstituted $C_n$-alkylamino, and heteroatom-substituted $C_n$-alkylamino. In certain embodiments, lower alkylaminos are contemplated. The term "lower alkylamino" refers to alkylaminos of 1-6 carbon atoms (that is, 1, 2, 3, 4, 5 or 6 carbon atoms). The term "heteroatom-unsubstituted $C_n$-alkylamino" refers to a radical, having a single nitrogen atom as the point of attachment, further having one or two saturated carbon atoms attached to the nitrogen atom, further having a linear or branched, cyclic or acyclic structure, containing a total of n carbon atoms, all of which are nonaromatic, 4 or more hydrogen atoms, a total of 1 nitrogen atom, and no additional heteroatoms. For example, a heteroatom-unsubstituted $C_1$-$C_{10}$-alkylamino has 1 to 10 carbon atoms. The term "heteroatom-unsubstituted $C_n$-alkylamino" includes groups, having the structure —NHR, in which R is a heteroatom-unsubstituted $C_n$-alkyl, as that term is defined above. A heteroatom-unsubstituted alkylamino group would include —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —N(CH$_3$)$_2$, —N(CH$_3$)CH$_2$CH$_3$, —N(CH$_2$CH$_3$)$_2$, N-pyrrolidinyl, and N-piperidinyl. The term "heteroatom-substituted $C_n$-alkylamino" refers to a radical, having a single nitrogen atom as the point of attachment, further having one or two saturated carbon atoms attached to the nitrogen atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_1$-$C_{10}$-alkylamino has 1 to 10 carbon atoms. The term "heteroatom-substituted $C_n$-alkylamino" includes groups, having the structure —NHR, in which R is a heteroatom-substituted $C_n$-alkyl, as that term is defined above.

The term "alkenylamino" includes straight-chain alkenylamino, branched-chain alkenylamino, cycloalkenylamino, cyclic alkenylamino, heteroatom-unsubstituted alkenyl amino, heteroatom-substituted alkenylamino, heteroatom-unsubstituted $C_n$-alkenylamino, heteroatom-substituted $C_n$-alkenyl amino, dialkenylamino, and alkyl(alkenyl)amino groups. In certain embodiments, lower alkenylaminos are contemplated. The "lower alkenylamino" refers to alkenylaminos of 1-6 carbon atoms (that is, 1, 2, 3, 4, 5 or 6 carbon atoms). The term "heteroatom-unsubstituted $C_n$-alkenylamino" refers to a radical, having a single nitrogen atom as the point of attachment, further having one or two carbon atoms attached to the nitrogen atom, further having a linear or branched, cyclic or acyclic structure, containing at least one nonaromatic carbon-carbon double bond, a total of n carbon atoms, 4 or more hydrogen atoms, a total of one nitrogen atom, and no additional heteroatoms. For example, a heteroatom-unsubstituted $C_2$-$C_{10}$-alkenylamino has 2 to 10 carbon atoms. The term "heteroatom-unsubstituted $C_n$-alkenylamino" includes groups, having the structure —NHR, in which R is a heteroatom-unsubstituted $C_n$-alkenyl, as that term is defined above. The ter, "heteroatom-substituted $C_n$-alkenylamino" refers to a radical, having a single nitrogen atom as the point of attachment and at least one nonaromatic carbon-carbon double bond, but no carbon-carbon triple bonds, further having one or two carbon atoms attached to the nitrogen atom, further having a linear or branched, cyclic or acyclic structure, further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkenylamino has 2 to 10 carbon atoms. The term "heteroatom-substituted $C_n$-alkenylamino" includes groups, having the structure —NHR, in which R is a heteroatom-substituted $C_n$-alkenyl, as that term is defined above.

The term "alkynylamino" includes straight-chain alkynylamino, branched-chain alkynyl amino, cyclo alkynyl amino, cyclic alkynylamino, heteroatom-unsubstituted alkynylamino, heteroatom-substituted alkynylamino, heteroatom-unsubstituted $C_n$-alkynylamino, heteroatom-substituted $C_n$-alkynyl amino, dialkynylamino, alkyl(alkynyl)amino, and alkenyl(alkynyl)amino groups. In certain embodiments, lower alkynylaminos are contemplated. The term "lower alkynylamino" refers to alkynylaminos of 1-6 carbon atoms (that is, 1, 2, 3, 4, 5 or 6 carbon atoms). The term "heteroatom-unsubstituted $C_n$-alkynylamino" refers to a radical, having a single nitrogen atom as the point of attachment, further having one or two carbon atoms attached to the nitrogen atom, further having a linear or branched, cyclic or acyclic structure, containing at least one carbon-carbon triple bond, a total of n carbon atoms, at least one hydrogen atoms, a total of one nitrogen atom, and no additional heteroatoms. For example, a heteroatom-unsubstituted $C_2$-$C_{10}$-alkynylamino has 2 to 10 carbon atoms. The term "heteroatom-unsubstituted $C_n$-alkynylamino" includes groups, having the structure —NHR, in which R is a heteroatom-unsubstituted $C_n$-alkynyl, as that term is defined above. The term "heteroatom-substituted $C_n$-alkynylamino" refers to a radical, having a single nitrogen atom as the point of attachment, further having one or two carbon atoms attached to the nitrogen atom, further having at least one nonaromatic carbon-carbon triple bond, further having a linear or branched, cyclic or acyclic structure, and further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkynylamino has 2 to 10 carbon atoms. The term "heteroatom-substituted $C_n$-alkynylamino" includes groups, having the structure —NHR, in which R is a heteroatom-substituted $C_n$-alkynyl, as that term is defined above.

The term "arylamino" includes heteroatom-unsubstituted arylamino, heteroatom-substituted arylamino, heteroatom-unsubstituted $C_n$-arylamino, heteroatom-substituted $C_n$-aryl amino, heteroarylamino, heterocyclic arylamino, and alkyl(aryl)amino groups. The term "heteroatom-unsubstituted $C_n$-arylamino" refers to a radical, having a single nitrogen atom as the point of attachment, further having at least one aromatic ring structure attached to the nitrogen atom, wherein the aromatic ring structure contains only carbon atoms, further having a total of n carbon atoms, 6 or more hydrogen atoms, a total of one nitrogen atom, and no additional heteroatoms. For example, a heteroatom-unsubstituted $C_6$-$C_{10}$-arylamino has 6 to 10 carbon atoms. The term "heteroatom-unsubstituted $C_n$-arylamino" includes groups, having the structure —NHR, in which R is a heteroatom-unsubstituted $C_w$-aryl, as that term is defined above. The term "heteroatom-substituted $C_n$-arylamino" refers to a radical, having a single nitrogen atom as the point of attachment, further having a total of n carbon atoms, at least one hydrogen atom, at least one additional heteroatoms, that is, in addition to the nitrogen atom at the point of attachment, wherein at least one of the carbon atoms is incorporated into one or more aromatic ring structures, further wherein each additional heteroatom is independently selected from the group consisting of N, O, F, Cl, Br, I, Si, P, and S. For example, a heteroatom-substituted $C_6$-$C_{10}$-arylamino has 6 to 10 carbon atoms. The term "heteroatom-substituted $C_n$-arylamino" includes groups, having the structure —NHR, in which R is a heteroatom-substituted $C_n$-aryl, as that term is defined above.

The term "aralkylamino" includes heteroatom-unsubstituted aralkylamino, heteroatom-substituted aralkylamino, heteroatom-unsubstituted $C_n$-aralkylamino, heteroatom-substituted $C_n$-aralkylamino, heteroaralkylamino, heterocyclic aralkylamino groups, and diaralkylamino groups. In certain embodiments, lower aralkylaminos are contemplated. The term "lower aralkylamino" refers to aralkylaminos of 7-12 carbon atoms (that is, 7, 8, 9, 10, 11, or 12 carbon atoms). The term "heteroatom-unsubstituted $C_n$-aralkylamino" refers to a radical, having a single nitrogen atom as the point of attachment, further having one or two saturated carbon atoms attached to the nitrogen atom, further having a total of n carbon atoms, wherein at least 6 of the carbon atoms form an aromatic ring structure containing only carbon atoms, 8 or more hydrogen atoms, a total of one nitrogen atom, and no additional heteroatoms. For example, a heteroatom-unsubstituted $C_7$-$C_{10}$-aralkylamino has 7 to 10 carbon atoms. The term "heteroatom-unsubstituted $C_n$-aralkylamino" includes groups, having the structure —NHR, in which R is a heteroatom-unsubstituted $C_n$-aralkyl, as that term is defined above. The term "heteroatom-substituted $C_n$-aralkylamino" refers to a radical, having a single nitrogen atom as the point of attachment, further having at least one or two saturated carbon atoms attached to the nitrogen atom, further having a total of n carbon atoms, 0, 1, or more than one hydrogen atom, at least one additional heteroatom, that is, in addition to the nitrogen atom at the point of attachment, wherein at least one of the carbon atom incorporated into an aromatic ring, further wherein each heteroatom is independently selected from the group consisting of N, O, F, Cl, Br, I, Si, P, and S. For example, a heteroatom-substituted $C_7$-$C_{10}$-aralkylamino has 7 to 10 carbon atoms. The term "heteroatom-substituted $C_n$-aralkylamino" includes groups, having the structure —NHR, in which R is a heteroatom-substituted $C_n$-aralkyl, as that term is defined above.

The term "amido" includes straight-chain amido, branched-chain amido, cycloamido, cyclic amido, heteroatom-unsubstituted amido, heteroatom-substituted amido, heteroatom-unsubstituted $C_n$-amido, heteroatom-substituted $C_n$-amido, alkylcarbonylamino, arylcarbonylamino, alkoxycarbonylamino, aryloxycarbonylamino, acylamino, alkylaminocarbonylamino, arylaminocarbonylamino, and ureido groups. The term "heteroatom-unsubstituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n carbon atoms, 1 or more hydrogen atoms, a total of one oxygen atom, a total of one nitrogen atom, and no additional heteroatoms. For example, a heteroatom-unsubstituted $C_1$-$C_{10}$-amido has 1 to 10 carbon atoms. The term "heteroatom-unsubstituted $C_n$-amido" includes groups, having the structure —NHR, in which R is a heteroatom-unsubstituted $C_n$-acyl, as that term is defined above. The group, —NHC(O)CH$_3$, is a non-limiting example of a heteroatom-unsubstituted amido group. The term "heteroatom-substituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n aromatic or nonaromatic carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-amido has 1 to 10 carbon atoms. The term "heteroatom-substituted $C_n$-amido" includes groups, having the structure —NHR, in which R is a heteroatom-unsubstituted $C_n$-acyl, as that term is defined above. The group, —NHCO$_2$CH$_3$, is a non-limiting example of a heteroatom-substituted amido group.

The term "alkylthio" includes straight-chain alkylthio, branched-chain alkylthio, cycloalkylthio, cyclic alkylthio, heteroatom-unsubstituted alkylthio, heteroatom-substituted alkylthio, heteroatom-unsubstituted $C_n$-alkylthio, and heteroatom-substituted $C_n$-alkylthio. In certain embodiments, lower alkylthios are contemplated. The term "lower alkylthio" refers to alkylthios of 1-6 carbon atoms (that is, 1, 2, 3, 4, 5 or 6 carbon atoms). The term "heteroatom-unsubstituted $C_n$-alkylthio" refers to a group, having the structure —SR, in which R is a heteroatom-unsubstituted $C_n$-alkyl, as that term is defined above. The group, —SCH$_3$, is an example of a heteroatom-unsubstituted alkylthio group. The term "heteroatom-substituted $C_n$-alkylthio" refers to a group, having the structure —SR, in which R is a heteroatom-substituted $C_n$-alkyl, as that term is defined above.

The term "alkenylthio" includes straight-chain alkenylthio, branched-chain alkenylthio, cycloalkenylthio, cyclic alkenylthio, heteroatom-unsubstituted alkenylthio, heteroatom-substituted alkenylthio, heteroatom-unsubstituted $C_n$-alkenylthio, and heteroatom-substituted $C_n$-alkenylthio. In certain embodiments, lower alkenylthios are contemplated. The term "lower alkenylthio" refers to alkenylthios of 1-6 carbon atoms (that is, 1, 2, 3, 4, 5 or 6 carbon atoms). The term "heteroatom-unsubstituted $C_n$-alkenylthio" refers to a group, having the structure —SR, in which R is a heteroatom-unsubstituted $C_n$-alkenyl, as that term is defined above. The term "heteroatom-substituted $C_n$-alkenylthio" refers to a group, having the structure —SR, in which R is a heteroatom-substituted $C_n$-alkenyl, as that term is defined above.

The term "alkynylthio" includes straight-chain alkynylthio, branched-chain alkynylthio, cycloalkynylthio, cyclic alkynylthio, heteroatom-unsubstituted alkynylthio, heteroatom-substituted alkynylthio, heteroatom-unsubstituted $C_n$-alkynylthio, and heteroatom-substituted $C_n$-alkynylthio. In certain embodiments, lower alkynylthios are contemplated. The term "lower alkynylthio" refers to alkynylthios of 1-6 carbon atoms (that is, 1, 2, 3, 4, 5 or 6 carbon atoms). The term "heteroatom-unsubstituted alkynylthio" refers to a group, having the structure —SR, in which R is a heteroatom-unsubstituted $C_n$-alkynyl, as that term is defined above. The term "heteroatom-substituted $C_n$-alkynylthio" refers to a group, having the structure —SR, in which R is a heteroatom-substituted $C_n$-alkynyl, as that term is defined above.

The term "arylthio" includes heteroatom-unsubstituted arylthio, heteroatom-substituted arylthio, heteroatom-unsubstituted $C_n$-arylthio, heteroatom-substituted $C_n$-arylthio, heteroarylthio, and heterocyclic arylthio groups. The term "heteroatom-unsubstituted $C_n$-arylthio" refers to a group, having the structure —SAr, in which Ar is a heteroatom-unsubstituted $C_n$-aryl, as that term is defined above. The group, —$SC_6H_5$, is an example of a heteroatom-unsubstituted arylthio group. The term "heteroatom-substituted $C_n$-arylthio" refers to a group, having the structure —SAr, in which Ar is a heteroatom-substituted $C_n$-aryl, as that term is defined above.

The term "aralkylthio" includes heteroatom-unsubstituted aralkylthio, heteroatom-substituted aralkylthio, heteroatom-unsubstituted $C_n$-aralkylthio, heteroatom-substituted $C_n$-aralkylthio, heteroaralkylthio, and heterocyclic aralkylthio groups. In certain embodiments, lower aralkylthios are contemplated. The term "lower aralkylthio" refers to aralkylthios of 7-12 carbon atoms (that is, 7, 8, 9, 10, 11, or 12 carbon atoms). The term "heteroatom-unsubstituted $C_n$-aralkylthio" refers to a group, having the structure —SAr, in which Ar is a heteroatom-unsubstituted $C_n$-aralkyl, as that term is defined above. The group, —$SCH_2C_6H_5$, is an example of a heteroatom-unsubstituted aralkyl group. The term "heteroatom-substituted $C_n$-aralkylthio" refers to a group, having the structure —SAr, in which Ar is a heteroatom-substituted $C_n$-aralkyl, as that term is defined above.

The term "acylthio" includes straight-chain acylthio, branched-chain acylthio, cycloacylthio, cyclic acylthio, heteroatom-unsubstituted acylthio, heteroatom-substituted acylthio, heteroatom-unsubstituted $C_n$-acylthio, heteroatom-substituted $C_n$-acylthio, alkylcarbonyloxy, arylcarbonyloxy, alkoxycarbonyloxy, aryloxycarbonyloxy, and carboxylate groups. In certain embodiments, lower acylthios are contemplated. The team "lower acylthio" refers to acylthios of 1-6 carbon atoms (that is, 1, 2, 3, 4, 5 or 6 carbon atoms). The term "heteroatom-unsubstituted $C_n$-acylthio" refers to a group, having the structure —SAc, in which Ac is a heteroatom-unsubstituted $C_n$-acyl, as that term is defined above. The group, —$SCOCH_3$, is an example of a heteroatom-unsubstituted acylthio group. The term "heteroatom-substituted $C_n$-acylthio" refers to a group, having the structure —SAc, in which Ac is a heteroatom-substituted $C_n$-acyl, as that term is defined above.

The term "alkylsilyl" includes straight-chain alkylsilyl, branched-chain alkylsilyl, cycloalkylsilyl, cyclic alkylsilyl, heteroatom-unsubstituted alkylsilyl, heteroatom-substituted alkylsilyl, heteroatom-unsubstituted $C_n$-alkylsilyl, and heteroatom-substituted $C_n$-alkylsilyl. In certain embodiments, lower alkylsilyls are contemplated. The term "lower alkylsilyl" refers to alkylsilyls of 1-6 carbon atoms (that is, 1, 2, 3, 4, 5 or 6 carbon atoms). The term "heteroatom-unsubstituted $C_n$-alkylsilyl" refers to a radical, having a single silicon atom as the point of attachment, further having one, two, or three saturated carbon atoms attached to the silicon atom, further having a linear or branched, cyclic or acyclic structure, containing a total of n carbon atoms, all of which are nonaromatic, 5 or more hydrogen atoms, a total of 1 silicon atom, and no additional heteroatoms. For example, a heteroatom-unsubstituted $C_1$-$C_{10}$-alkylsilyl has 1 to 10 carbon atoms. An alkylsilyl group includes dialkylamino groups. The groups, —$Si(CH_3)_3$ and —$Si(CH_3)_2C(CH_3)_3$, are non-limiting examples of heteroatom-unsubstituted alkylsilyl groups. The term "heteroatom-substituted $C_n$-alkylsilyl" refers to a radical, having a single silicon atom as the point of attachment, further having at least one, two, or three saturated carbon atoms attached to the silicon atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the silicon atom at the point of attachment, wherein each additional heteroatom is independently selected from the group consisting of N, O, F, Cl, Br, I, Si, P, and S. For example, a heteroatom-substituted $C_1$-$C_{10}$-alkylsilyl has 1 to 10 carbon atoms.

The term "phosphonate" includes straight-chain phosphonate, branched-chain phosphonate, cyclophosphonate, cyclic phosphonate, heteroatom-unsubstituted phosphonate, heteroatom-substituted phosphonate, heteroatom-unsubstituted $C_n$-phosphonate, and heteroatom-substituted $C_n$-phosphonate. The term "heteroatom-unsubstituted $C_n$-phosphonate" refers to a radical, having a single phosphorous atom as the point of attachment, further having a linear or branched, cyclic or acyclic structure, further having a total of n carbon atoms, 2 or more hydrogen atoms, a total of three oxygen atom, and no additional heteroatoms. The three oxygen atoms are directly attached to the phosphorous atom, with one of these oxygen atoms doubly bonded to the phosphorous atom. For example, a heteroatom-unsubstituted $C_0$-$C_{10}$-phosphonate has 0 to 10 carbon atoms. The groups, —$P(O)(OH)_2$, —$P(O)(OH)OCH_3$, —$P(O)(OH)OCH_2CH_3$, —$P(O)(OCH_3)_2$, and —$P(O)(OH)(OC_6H_5)$ are non-limiting examples of heteroatom-unsubstituted phosphonate groups. The term "heteroatom-substituted $C_n$-phosphonate" refers to a radical, having a single phosphorous atom as the point of attachment, further having a linear or branched, cyclic or acyclic structure, further having a total of n carbon atoms, 2 or more hydrogen atoms, three or more oxygen atoms, three of which are directly attached to the phosphorous atom, with one of these three oxygen atoms doubly bonded to the phosphorous atom, and further having at least one additional heteroatom in addition to the three oxygen atoms, wherein each additional heteroatom is independently selected from the group consisting of N, O, F, Cl, Br, I, Si, P, and S. For example, a heteroatom-unsubstituted $C_0$-$C_{10}$-phosphonate has 0 to 10 carbon atoms.

The term "phosphinate" includes straight-chain phosphinate, branched-chain phosphinate, cyclophosphinate, cyclic phosphinate, heteroatom-unsubstituted phosphinate, heteroatom-substituted phosphinate, heteroatom-unsubstituted $C_n$-phosphinate, and heteroatom-substituted $C_n$-phosphinate. The term "heteroatom-unsubstituted $C_n$-phosphinate" refers to a radical, having a single phosphorous atom as the point of attachment, further having a linear or branched, cyclic or acyclic structure, further having a total of n carbon atoms, 2 or more hydrogen atoms, a total of two oxygen atom, and no additional heteroatoms. The two oxygen atoms are directly attached to the phosphorous atom, with one of these oxygen atoms doubly bonded to the phosphorous atom. For example, a heteroatom-unsubstituted $C_0$-$C_{10}$-phosphinate has 0 to 10 carbon atoms. The groups, —$P(O)(OH)H$, —$P(O)(OH)CH_3$, —$P(O)(OH)CH_2CH_3$, —$P(O)(OCH_3)CH_3$, and —$P(O)(OC_6H_5)H$ are non-limiting examples of heteroatom-unsubstituted phosphinate groups. The term "heteroatom-substituted $C_n$-phosphinate" refers to a radical, having a single phosphorous atom as the point of attachment, further having a linear or branched, cyclic or acyclic structure, further having a total of n carbon atoms, 2 or more hydrogen atoms, two or more oxygen atoms, two of which are directly attached to the phosphorous atom, with one of these two oxygen atoms doubly bonded to the phosphorous atom, and further having at least one additional heteroatom in addition to the two oxygen atoms, wherein each additional heteroatom is independently selected from the group consisting of N, O, F, Cl, Br, I, Si, P, and S. For example, a heteroatom-unsubstituted $C_0$-$C_{10}$-phosphinate has 0 to 10 carbon atoms.

Modifications or derivatives of the compounds, agents, and active ingredients disclosed throughout this specification are contemplated as being useful with the methods and compositions of the present invention. Derivatives may be prepared and the properties of such derivatives may be assayed for their desired properties by any method known to those of skill in the art.

In certain aspects, "derivative" refers to a chemically modified compound that still retains the desired effects of the compound prior to the chemical modification. "Isoxazole derivatives," therefore, refers to a chemically modified compound that still retains the desired effects of the parent isoxazole prior to its chemical modification. Such effects may be enhanced (e.g., slightly more effective, twice as effective, etc.) or diminished (e.g., slightly less effective, 2-fold less effective, etc.) relative to the parent isoxazole, but may still be considered an isoxazole derivative. Such derivatives may have the addition, removal, or substitution of one or more chemical moieties on the parent molecule. Non-limiting examples of the types modifications that can be made to the compounds and structures disclosed herein include the addition or removal of lower unsubstituted alkyls such as methyl, ethyl, propyl, or substituted lower alkyls such as hydroxymethyl or aminomethyl groups; carboxyl groups and carbonyl groups; hydroxyls; nitro, amino, amide, and azo groups; sulfate, sulfonate, sulfono, sulfhydryl, sulfonyl, sulfoxido, phosphate, phosphono, phosphoryl groups, and halide substituents. Additional modifications can include an addition or a deletion of one or more atoms of the atomic framework, for example, substitution of an ethyl by a propyl; substitution of a phenyl by a larger or smaller aromatic group. Alternatively, in a cyclic or bicyclic structure, heteroatoms such as N, S, or O can be substituted into the structure instead of a carbon atom.

Prodrugs and solvates of the compounds of the present invention are also contemplated herein. The term "prodrug" as used herein, is understood as being a compound which, upon administration to a subject, such as a mammal, undergoes chemical conversion by metabolic or chemical processes to yield a compound any of the formulas herein, or a salt and/or solvate thereof (Bundgaard, 1991; Bundgaard, 1985). Solvates of the compounds of the present invention are preferably hydrates.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like.

Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, Selection and Use* (P. H. Stahl & C. G. Wermuth eds., Verlag Helvetica Chimica Acta, 2002), which is incorporated herein by reference.

As used herein, the term "cyclic group" refers to a carbocycle group (e.g., cyclopropyl, cyclohexyl), a heterocycle group (e.g., pyrrolidinyl), an aryl group, or any combination thereof (e.g., fused bicyclic group).

As used herein, "protecting group" refers to a moiety attached to a functional group to prevent an otherwise unwanted reaction of that functional group. Protecting groups are well-known to those of skill in the art. Non-limiting exemplary protecting groups fall into categories such as hydroxy protecting groups, amino protecting groups, sulfhydryl protecting groups and carbonyl protecting groups. Such protecting groups may be found in Greene and Wuts, 1999. Compounds of the present invention are specifically contemplated wherein one or more functional groups are protected by a protecting group.

Compounds of the present invention may contain one or more asymmetric centers and thus can occur as racemates and racemic mixtures, single enantiomers, diastereomeric mixtures and individual diastereomers. In certain embodiments, a single diastereomer is present. All possible stereoisomers of the compounds of the present invention are contemplated as being within the scope of the present invention. However, in certain aspects, particular diastereomers are contemplated. The chiral centers of the compounds of the present invention can have the S- or the R-configuration, as defined by the IUPAC 1974 Recommendations. In certain aspects, certain compounds of the present invention may comprise S- or R-configurations at particular carbon centers.

Solvent choices for the synthetic preparation of compounds of the present invention will be known to one of ordinary skill in the art. Solvent choices may depend, for example, on which one(s) will facilitate the solubilizing of all the reagents or, for example, which one(s) will best facilitate the desired reaction (particularly when the mechanism of the reaction is known). Solvents may include, for example, polar solvents and non-polar solvents. Solvents choices include, but are not limited to, tetrahydrofuran, dimethylformamide, dimethylsulfoxide, dioxane, methanol, ethanol, hexane, methylene chloride and acetonitrile. More than one solvent may be chosen for any particular reaction or purification procedure. Water may also be admixed into any solvent choice. Further, water, such as distilled water, may constitute the reaction medium instead of a solvent.

Persons of ordinary skill in the art will be familiar with methods of purifying compounds of the present invention. One of ordinary skill in the art will understand that compounds of the present invention can generally be purified at any step, including the purification of intermediates as well as purification of the final products. In preferred embodiments, purification is performed via silica gel column chromatography or HPLC.

In view of the above definitions, other chemical terms used throughout this application can be easily understood by those of skill in the art. Terms may be used alone or in any combination thereof. The preferred and more preferred chain lengths of the radicals apply to all such combination.

D. STEM CELLS

Stem cells are primal cells found in all multi-cellular organisms. They retain the ability to renew themselves through mitotic cell division and can differentiate into a diverse range of specialized cell types. Research in the human stem cell field grew out of findings by Canadian scientists Ernest A. McCulloch and James E. Till in the 1960s.

The three broad categories of mammalian stem cells are: embryonic stem cells, derived from blastocysts, and adult stem cells, which are found in adult tissues. In a developing embryo, stem cells can differentiate into all of the specialized embryonic tissues. In adult organisms, stem cells and progenitor cells act as a repair system for the body, replenishing specialized cells. In particular embodiments, neural stem cells isolated from the adult mammalian brain and embryonic stem cells are contemplated by the present invention. Human bone marrow stromal cells are also contemplated, in certain embodiments.

As stem cells can be grown and transformed into specialized cells with characteristics consistent with cells of various tissues such as muscles or nerves through cell culture, their use in medical therapies has been proposed. In particular, embryonic cell lines, autologous embryonic stem cells generated through therapeutic cloning, and highly plastic adult stem cells from mature organs of the body.

"Potency" specifies the differentiation potential (the potential to differentiate into different cell types) of the stem cell. Totipotent stem cells are produced from the fusion of an egg and sperm cell. Cells produced by the first few divisions of the fertilized egg are also totipotent. These cells can differentiate into embryonic and extraembryonic cell types. Pluripotent stem cells are the descendants of totipotent cells and can differentiate into cells derived from any of the three germ layers. Multipotent stem cells can produce only cells of a closely related family of cells (e.g., hematopoietic stem cells differentiate into red blood cells, white blood cells, platelets, etc.). Unipotent cells can produce only one cell type, but have the property of self-renewal which distinguishes them from non-stem cells.

1. Embryonic Stem Cells

Embryonic stem cell lines (ES cell lines) are cultures of cells derived from the epiblast tissue of the inner cell mass (ICM) of a blastocyst. A blastocyst is an early stage embryo—approximately 4 to 5 days old in humans and consisting of 50-150 cells. ES cells are pluripotent, and give rise during development to all derivatives of the three primary germ layers: ectoderm, endoderm and mesoderm. In other words, they can develop into each of the more than 200 cell types of the adult body when given sufficient and necessary stimulation for a specific cell type. They do not contribute to the extraembryonic membranes or the placenta.

Nearly all research to date has taken place using mouse embryonic stem cells (mES) or human embryonic stem cells (hES). Both have the essential stem cell characteristics, yet they require very different environments in order to maintain an undifferentiated state. Mouse ES cells are grown on a layer of gelatin and require the presence of Leukemia Inhibitory Factor (LIF). Human ES cells are grown on a feeder layer of mouse embryonic fibroblasts (MEF's) and require the presence of basic Fibroblast Growth Factor (bFGF or FGF-2). Without optimal culture conditions or genetic manipulation embryonic stem cells will rapidly differentiate.

A human embryonic stem cell is also defined by the presence of several transcription factors and cell surface proteins. The transcription factors Oct-4, Nanog, and Sox2 form the core regulatory network which ensures the suppression of genes that lead to differentiation and the maintenance of pluripotency. The cell surface proteins most commonly used to identify hES cells are the glycolipids SSEA3 and SSEA4 and the keratan sulfate antigens Tra-1-60 and Tra-1-81. The molecular definition of a stem cell includes many more proteins and continues to be a topic of research.

After 20 years of research, there are no approved treatments or human trials using embryonic stem cells. Their tendency to produce tumors and malignant carcinomas, cause transplant rejection, and form the wrong kinds of cells are just a few of the hurdles that embryonic stem cell researchers still face. Many nations currently have moratoria on either ES cell research or the production of new ES cell lines. Because of their combined abilities of unlimited expansion and pluripotency, embryonic stem cells remain a theoretically potential source for regenerative medicine and tissue replacement after injury or disease.

The present invention contemplates the use of embryonic stem cells. Table 1 lists cellular markers that can be used to identify and separate embryonic stem cells for use in accordance with the present invention.

TABLE 1

Pluripotent Stem Cell Markers

| Cell Marker | Cell Type | Significance |
|---|---|---|
| Alkaline phosphatase | Embryonic stem (ES), embryonal carcinoma (EC) | Elevated expression of this enzyme is associated with undifferentiated pluripotent stem cell (PSC) |
| Alpha-fetoprotein (AFP) | Endoderm | Protein expressed during development of primitive endoderm; reflects endodermal differentiation Pluripotent Stem Cells |
| Bone morphogenetic protein-4 | Mesoderm | Growth and differentiation factor expressed during early mesoderm formation and differentiation |
| Brachyury | Mesoderm | Transcription factor important in the earliest phases of mesoderm formation and differentiation; used as the earliest indicator of mesoderm formation |

TABLE 1-continued

Pluripotent Stem Cell Markers

| Cell Marker | Cell Type | Significance |
|---|---|---|
| Cluster designation 30 (CD30) | ES, EC | Surface receptor molecule found specifically on PSC |
| Cripto (TDGF-1) | ES, cardiomyocyte | Gene for growth factor expressed by ES cells, primitive ectoderm, and developing cardiomyocyte |
| GATA-4 gene | Endoderm | Expression increases as ES differentiates into endoderm |
| GCTM-2 | ES, EC | Antibody to a specific extracellular-matrix molecule that is synthesized by undifferentiated PSCs |
| Genesis | ES, EC | Transcription factor uniquely expressed by ES cells either in or during the undifferentiated state of PSCs |
| Germ cell nuclear factor | ES, EC | Transcription factor expressed by PSCs |
| Hepatocyte nuclear factor-4 (HNF-4) | Endoderm | Transcription factor expressed early in endoderm formation |
| Nestin | Ectoderm, neural and pancreatic progenitor | Intermediate filaments within cells; characteristic of primitive neuroectoderm formation |
| Neuronal cell-adhesion molecule (N-CAM) | Ectoderm | Cell-surface molecule that promotes cell-cell interaction; indicates primitive neuroectoderm formation |
| Oct-4 | ES, EC | Transcription factor unique to PSCs; essential for establishment and maintenance of undifferentiated PSCs |
| Pax6 | Ectoderm | Transcription factor expressed as ES cell differentiates into neuroepithelium |
| Stage-specific embryonic antigen-3 (SSEA-3) | ES, EC | Glycoprotein specifically expressed in early embryonic development and by undifferentiated PSCs |
| Stage-specific embryonic antigen-4 (SSEA-4) | ES, EC | Glycoprotein specifically expressed in early embryonic development and by undifferentiated PSCs |
| Stem cell factor (SCF or c-Kit ligand) | ES, EC, HSC, MSC | Membrane protein that enhances proliferation of ES and EC cells, hematopoietic stem cell (HSCs), and mesenchymal stem cells (MSCs); binds the receptor c-Kit |
| Telomerase | ES, EC | An enzyme uniquely associated with immortal cell lines; useful for identifying undifferentiated PSCs |
| TRA-1-60 | ES, EC | Antibody to a specific extracellular matrix molecule is synthesized by undifferentiated PSCs |
| TRA-1-81 | ES, EC | Antibody to a specific extracellular matrix molecule normally synthesized by undifferentiated PSCs |
| Vimentin | Ectoderm, neural and pancreatic progenitor | Intermediate filaments within cells; characteristic of primitive neuroectoderm formation |

2. Adult Stem Cells

Adult stem cells, a cell which is found in a developed organism, have two properties: the ability to divide and create another cell like itself, and also divide and create a cell more differentiated than itself. Pluripotent adult stem cells are rare and generally small in number but can be found in a number of tissues including umbilical cord blood. Most adult stem cells are lineage restricted (multipotent) and are generally referred to by their tissue origin (mesenchymal stem cell, adipose-derived stem cell, endothelial stem cell, etc.). A great deal of adult stem cell research has focused on clarifying their capacity to divide or self-renew indefinitely and their differentiation potential.

While embryonic stem cell potential remains untested, adult stem cell treatments have been used for many years to successfully treat leukemia and related bone/blood cancers through bone marrow transplants. The use of adult stem cells in research and therapy is not as controversial as embryonic stem cells, because the production of adult stem cells does not require the destruction of an embryo. Consequently, more US government funding is being provided for adult stem cell research.

The present invention contemplates, in particular embodiments, neural stem/progenitor cells that act as precursor cells for the mature cells of the central nervous system (e.g., neurons, oligodendrocytes, and astrocytes).

i. Cardiogenic Stem Cells

Evidence for potential stem cell-based therapies for heart disease has been provided by studies showing that human adult stem cells, taken from the bone marrow, are capable of giving rise to vascular endothelial cells when transplanted into rats. Such stem cells demonstrated plasticity, meaning that they become cell types that they would not normally be. The cells were used to form new blood vessels in the damaged area of the rats' hearts and to encourage proliferation of preexisting vasculature following the experimental heart attack.

Like the mouse stem cells, human hematopoietic stem cells can be induced under the appropriate culture conditions to differentiate into numerous tissue types, including cardiac muscle. When injected into the bloodstream leading to the damaged rat heart, these cells prevented the death of hypertrophied or thickened but otherwise viable myocardial cells and reduced progressive formation of collagen fibers and scars. Furthermore, hematopoietic cells can be identified on the basis of highly specific cell markers that differentiate them from cardiomyocyte precursor cells, enabling such cells to be used alone or in conjunction with myocyte-regeneration strategies or pharmacological therapies.

Table 2, below, lists cell surface markers that can be used to identify cardiogenic stem cells. In particular, Flk1$^+$ cells are contemplated.

TABLE 2

Cardiac Progenitor Markers

| Cell Marker | Cell Type | Significance |
| --- | --- | --- |
| MyoD and Pax7 | Myoblast, myocyte | Transcription factors that direct differentiation of myoblasts into mature myocytes |
| Myogenin and MR4 | Skeletal myocyte | Secondary transcription factors required for differentiation of myoblasts from muscle stem cells |
| Myosin heavy chain | Cardiomyocyte | A component of structural and contractile protein found in cardiomyocyte |
| Myosin light chain | Skeletal myocyte | A component of structural and contractile protein found in skeletal myocyte | ii. Neural Stem Cells

The adult mammalian central nervous system (CNS) is composed primarily of three differentiated cell types—neurons, astrocytes and oligodendrocytes. Astrocytes and oligodendrocytes provide a critical supporting role for neuronal function. Neurons responsible for forming connections and are the communicating cells of the nervous system. The limits on adult mammals' ability to replace non-functional CNS tissue makes CNS death due to injury or disease devastating. Thus, research on brain repair has traditionally focused on keeping neurons alive following injury and promoting their ability to extend processes and establish functional cell connections. This focus was based on the belief that the adult mammalian CNS was incapable of generating new brain cells. However, the early 1990's brought the discovery of stem cells existed in the embryonic and adult CNS, opening up the way for research on the use of these cells in neuronal therapies and CNS tissue repair.

Neural stem cells have been isolated from nearly all regions of the embryonic mouse CNS, including the septum, cortex, thalamus, ventral mesencephalon and spinal cord. Cells from all these CNS regions exhibit the same general features—extensive proliferative ability, self-renewal and differentiation of the progeny into neurons, astrocytes and oligodendrocytes. In the adult mouse, neural stem cells appear to be located primarily in the sub-ventricular zone (SVZ) of the forebrain and in the sub-granular layer zone (SGZ) of the dentate gyrus of the hippocampal formation. A recent study indicates the cells from the SGZ may have a more limited proliferative potential, and that the hippocampal stem cells lie dorsal to the hippocampus in a collapsed ventricle.

While the role of neural stem cells in vivo is poorly understood, they do appear to exhibit properties similar to other stem cells. In the sub-ventricular region, for example, stem cells can be induced to proliferate and to repopulate the sub-ventricular zone following irradiation. Stem cell-derived sub-ependymal progenitor cells are the source of new neurons in the olfactory bulb of rodents and in the association cortex of nonhuman primates under normal conditions. And recently, it has been shown that stem cell progeny in the hippocampal region are able to compensate for behavioral deficits following ischemic injury in rodents.

Neural stem/progenitor cells are normally grown in serum-free medium (N2/B27 or N2 supplement in DMEM:F12) and supplemented with growth factors, such as fibroblast growth factor and/or epidermal growth factor. Under these conditions, stem cells remain undifferentiated and do not give rise to neurons. To induce neuronal differentiation, cells may be trypsinized (to dissociate into single cells) and re-plated in serum-free medium containing "differentiating agents," such as isoxazole-derived small-molecules described herein. Within 24 hours, cells will undergo a rapid and vast morphological change, flattening and extension of neuronal-like processes. By 4 days, there is increased neuronal gene expression by RT-PCR (for mRNA), protein blotting (for protein), and staining for neuronal markers (by immunohistochemistry). Under certain conditions when stem cells are co-cultured with astrocytes, the stem cell can differentiate into mature neuronal cells that fire action potentials.

Table 3, below, lists various cell markers for neural stem cells.

TABLE 3

Neurogenic Progenitor Markers

| Cell Marker | Cell Type | Significance |
| --- | --- | --- |
| CD133 | Neural stem cell, HSC | Cell-surface protein that identifies neural stem cells, which give rise to neurons and glial cells |
| Glial fibrillary acidic protein (GFAP) | Astrocyte | Protein specifically produced by astrocyte |
| Microtubule-associated protein-2 (MAP-2) | Neuron | Dendrite-specific MAP; protein found specifically in dendritic branching of neuron |
| Myelin basic protein (MPB) | Oligodendrocyte | Protein produced by mature oligodendrocytes; located in the myelin sheath surrounding neuronal structures |
| Nestin | Neural progenitor | Intermediate filament structural protein expressed in primitive neural tissue |
| Neural tubulin | Neuron | Important structural protein for neuron; identifies differentiated neuron |
| Neurofilament (NF) | Neuron | Important structural protein for neuron; identifies differentiated neuron |
| Neurosphere | Embryoid body (EB), ES | Cluster of primitive neural cells in culture of differentiating ES cells; indicates presence of early neurons and glia |
| Noggin | Neuron | A neuron-specific gene expressed during the development of neurons |
| O4 | Oligodendrocyte | Cell-surface marker on immature, developing oligodendrocyte |
| O1 | Oligodendrocyte | Cell-surface marker that characterizes mature oligodendrocyte |
| Synaptophysin | Neuron | Neuronal protein located in synapses; indicates connections between neurons |
| Tau | Neuron | Type of MAP; helps maintain structure of the axon |

E. DETECTION OF CELL SURFACE MARKERS

In accordance with the present invention, one will seek to obtain various stem cell populations by screening of cell populations for appropriate cell surface markers, as discussed above. Generally, this is performed by labeling or physically selecting cells that are bound by antibodies to cell determinants that identify the cells as stem, pluripotent or totipotent stem cells. It is particularly contemplated that antibodies will be of particular use in the various cell separation techniques described below.

1. Antibody Constructs

Antibodies directed against the various cell surface antigens are readily available from commercial sources. While available from commercial sources, it is also contemplated that monoclonal or polyclonal antibodies for use in the context of the invention may be constructed by a person of ordinary skill.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')2, single domain antibodies (DABs), Fv, scFv (single chain Fv), and the like. The techniques for preparing and using various antibody-based constructs and fragments are well known in the art. Means for preparing and characterizing antibodies are also well known in the art (see, e.g., Antibodies: A Laboratory Manual, Cold Spring Harbor Laboratory, 1988; incorporated herein by reference).

Monoclonal antibodies (MAbs) are recognized to have certain advantages, e.g., reproducibility and large-scale production, and their use is generally preferred. The invention thus provides monoclonal antibodies of the human, murine, monkey, rat, hamster, rabbit and even chicken origin. Due to the ease of preparation and ready availability of reagents, murine monoclonal antibodies will often be preferred.

2. Antibody Conjugates

The instant invention provides for the use of antibodies against various cell surface antigens which are generally of the monoclonal type, and that may be linked to at least one agent to form an antibody conjugate. It is conventional to link or covalently bind or complex at least one desired molecule or moiety. Such a molecule or moiety may be, but is not limited to a reporter molecule. A reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Any antibody of sufficient selectivity, specificity or affinity may be employed as the basis for an antibody conjugate. Such properties may be evaluated using conventional immunological screening methodology known to those of skill in the art. Sites for binding to biological active molecules in the antibody molecule, in addition to the canonical antigen binding sites, include sites that reside in the variable domain that can bind pathogens, B-cell superantigens, the T cell co-receptor CD4 and the HIV-1 envelope (Sasso et al., 1989; Shorki et al., 1991; Silvermann et al., 1995; Cleary et al., 1994; Lenert et al., 1990; Berberian et al., 1993; Kreier et al., 1991). In addition, the variable domain is involved in antibody self-binding (Kang et al., 1988), and contains epitopes (idiotopes) recognized by anti-antibodies (Kohler et al., 1989).

Certain examples of antibody conjugates are those conjugates in which the antibody is linked to a detectable label. "Detectable labels" are compounds and/or elements that can be detected due to their specific functional properties, and/of chemical characteristics, the use of which allows the antibody to which they are attached to be detected, and/or further quantified if desired.

Many appropriate imaging agents are known in the art, as are methods for their attachment to antibodies (see, e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might employ, by way of example, ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might employ, for example, $^{211}$astatine, $^{14}$-carbon, $^{51}$chromium, $^{36}$-chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, $^{99m}$technicium and/or $^{90}$yttrium. $^{125}$I is often being preferred for use in certain embodiments, and $^{99m}$technicium and/or indium$^{111}$ are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugate contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

3. Methods of Conjugation

If desired, the compound of interest may be joined to an antibody via a biologically-releasable bond, such as a selectively-cleavable linker or amino acid sequence. Certain linkers will generally be preferred over other linkers, based on differing pharmacologic characteristics and capabilities. For example, linkers that contain a disulfide bond that is sterically "hindered" are to be preferred, due to their greater stability in vivo, thus preventing release of the moiety prior to binding at the site of action.

Additionally, any other linking/coupling agents and/or mechanisms known to those of skill in the art can be used to combine to components or agents with antibodies of the present invention, such as, for example, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, or combinations thereof.

Cross-linking reagents are used to form molecular bridges that tie together functional groups of two different molecules, e.g., a stabilizing and coagulating agent. However, it is contemplated that dimers or multimers of the same analog can be made or that heteromeric complexes comprised of different analogs can be created. To link two different compounds in a step-wise manner, hetero-bifunctional cross-linkers can be used that eliminate unwanted homopolymer formation.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Preferred uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single-chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

F. CELL SEPARATION TECHNIQUES

Methods of separating cell populations and cellular subsets are well known in the art and may be applied to the cell populations of the present invention. Cells purified in this fashion may then be used for stimulation and cell replacement therapy, such as in tissue regeneration purposes. Embryonic stem cells and neural stem cells, as well as stem cells for endothelial, cardiac and other cell types are believed by the inventors to be useful in accordance with the present invention. Stimulating those stem cells from a quiescent condition with compounds of the present invention should promote differentiation. They may also be treated with particular combinations with previously known growth and differentiation factors and then cultured to expand and/or differentiate. The following description sets forth exemplary methods of separation for stem cells based upon the surface expression of various markers.

1. Fluorescence Activated Cell Sorting (FACS)

FACS facilitates the quantitation and/or separation of subpopulations of cells based upon surface markers. Cells to be sorted are first tagged with a fluorescently labeled antibody or other marker specific ligand. Generally, labeled antibodies and ligands are specific for the expression of a phenotype specific cell surface molecule. The labeled cells are then passed through a laser beam and the fluorescence intensity of each cell determined. The sorter distributes the positive and negative cells into label-plus and label-minus wells at a flow rate of approximately 3000 cells per second.

The use of multiple fluorescent tags exciting at different wavelengths allows for sorting based upon multiple or alternate criteria. Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red. Thus, for example, a single PBMC sample may be analyzed with alternatively labeled anti-Ig antibody, anti-CD3 antibody, anti-CD8 antibody and anti-CD4 antibody to screen for the presence of B cells and T cells within the sample, as well as distinguishing specific T cell subsets.

FACS analysis and cell sorting is carried out on a flow cytometer. A flow cytometer generally consists of a light source, normally a laser, collection optics, electronics and a computer to translate signals to data. Scattered and emitted fluorescent light is collected by two lenses (one positioned in front of the light source and one set at right angles) and by a series of optics, beam splitters and filters, which allow for specific bands of fluorescence to be measured.

Flow cytometer apparatus permit quantitative multiparameter analysis of cellular properties at rates of several thousand cells per second. These instruments provide the ability to differentiate among cell types. Data are often displayed in one-dimensional (histogram) or two-dimensional (contour plot, scatter plot) frequency distributions of measured variables. The partitioning of multiparameter data files involves consecutive use of the interactive one- or two-dimensional graphics programs.

Quantitative analysis of multiparameter flow cytometric data for rapid cell detection consists of two stages: cell class characterization and sample processing. In general, the process of cell class characterization partitions the cell feature into cells of interest and not of interest. Then, in sample processing, each cell is classified in one of the two categories according to the region in which it falls. Analysis of the class of cells is very important, as high detection performance may be expected only if an appropriate characteristic of the cells is obtained.

Not only is cell analysis performed by flow cytometry, but so too is sorting of cells. In U.S. Pat. No. 3,826,364, an apparatus is disclosed which physically separates particles, such as functionally different cell types. In this machine, a laser provides illumination which is focused on the stream of particles by a suitable lens or lens system so that there is highly localized scatter from the particles therein. In addition, high intensity source illumination is directed onto the stream of particles for the excitation of fluorescent particles in the stream. Certain particles in the stream may be selectively charged and then separated by deflecting them into designated receptacles. A classic form of this separation is via fluorescent tagged antibodies, which are used to mark one or more cell types for separation.

Additional and alternate methods for performing flow cytometry and fluorescent antibody cell sorting are described in U.S. Pat. Nos. 4,284,412; 4,989,977; 4,498,766; 5,478,722; 4,857,451; 4,774,189; 4,767,206; 4,714,682; 5,160,974; and 4,661,913, herein expressly incorporated by reference.

2. Micro-Bead Separation

Cells in suspension may be separated to very high purity according to their surface antigens using micro-bead technologies. The basic concept in micro-bead separations is to selectively bind the biomaterial of interest (e.g., a specific cell, protein, or DNA sequence) to a particle and then separate it from its surrounding matrix. Micro-bead separation involves contacting a cell suspension with a slurry of micro-beads labeled with a cell surface specific antibody or ligand. Cells labeled with the micro-beads are then separated using an affinity capture method specific for some property of the beads. This format facilitates both positive and negative selection.

Magnetic beads are uniform, superparamagnetic beads generally coated with an affinity tag such as recombinant streptavidin that will bind biotinylated immunoglobulins, or other biotinylated molecules such as, for example, peptides/proteins or lectins. Magnetic beads are generally uniform micro- or nanoparticles of $Fe_3O_4$. These particles are superparamagnetic, meaning that they are attracted to a magnetic field but retain no residual magnetism after the field is removed. Suspended superparamagnetic particles tagged to a cell of interest can be removed from a matrix using a magnetic field, but they do not agglomerate (i.e., they stay suspended) after removal of the field.

A common format for separations involving superparamagnetic nanoparticles is to disperse the beads within the pores of larger microparticles. These microparticles are coated with a monoclonal antibody for a cell-surface antigen. The antibody-tagged, superparamagnetic microparticles are then introduced into a cellular suspension. The particles bind to cells expressing the surface antigen of interest and maybe separated out with the application of a magnetic field. This may be facilitated by running the suspension over a high gradient magnetic separation column placed in a strong magnetic field. The magnetically labeled cells are retained in the column while non-labeled cells pass through. When the column is removed from the magnetic field, the magnetically retained cells are eluted. Both, labeled and non-labeled fractions can be completely recovered.

3. Affinity Chromatography

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed elsewhere in this document.

G. STEM/PROGENITOR/DIFFERENTIATED CELL CULTURE

Cell culture facilitates the maintenance and propagation of cells in vitro under controlled conditions. Cells may be cultured in a variety of types of vessels constructed of, for example, glass or plastic. The surfaces of culture vessels may be pre-treated or coated with, for example, collagen, polylysine, or components of the extracellular matrix, to facilitate the cellular adherence. Some sophisticated techniques utilize entire layers of adherent cells, feeder cells, which are used to support the growth of cells with more demanding growth requirements.

Cells are normally cultured under conditions designed to closely mimic those observed in vivo. In order to mimic the normal physiological environment cells are generally incubated in a $CO_2$ atmosphere with semi-synthetic growth media. Culture media is buffered and contains, among other things, amino acids, nucleotides, salts, vitamins, and also a supplement of serum such as fetal calf serum (FCS) horse serum or even human serum. Culture media may be further supplemented with growth factors and inhibitors such as hormones, transferrin, insulin, selenium, and attachment factors.

As a rule, cells grown in vitro do not organize themselves into tissues. Instead, cultured cells grow as monolayers (or in some instances as multilayers) on the surface of tissue culture dishes. The cells usually multiply until they come into contact with each other to form a monolayer and stop growing when they come into contact with each other due to contact inhibition.

Anchorage-dependent cells show the phenomenon of adherence, i.e., they grow and multiply only if attached to the inert surface of a culture dish or another suitable support. Such cells cannot normally be grown without a solid support. Many cells do not require this solid surface and show a phenomenon known as Anchorage-independent growth. Accordingly, one variant of growing these cells in culture is the use of Spinner cultures or suspension cultures in which single cells float freely in the medium and are maintained in suspension by constant stirring or agitation. This technique is particularly useful for growing large amounts of cells in batch cultures.

Anchorage-independent cells are usually capable of forming colonies in semisolid media. Some techniques have been developed that can be used also to grow anchorage-dependent cells in spinner cultures. They make use of microscopically small positively-charged dextran beads to which these cells can attach.

The starting material for the establishment of a cell culture typically is tissue from a suitable donor obtained under sterile conditions. The tissues may be minced and treated with proteolytic enzymes such as trypsin, collagenase of dispase to obtain a single cell suspension that can be used to inoculate a culture dish. In some cases dispersion of tissue is also effectively achieved by treatment with buffers containing EDTA. A particular form of initiating a cell culture is the use of tiny pieces of tissues from which cells may grow out in vitro.

Primary cell cultures maintained for several passages may undergo a crisis. As crisis is usually associated with alterations of the properties of the cells and may proceed quickly or extend over many passages. Loss of contact inhibition is frequently an indication of cells having lost their normal characteristics. These cells then grow as multilayers in tissue culture dishes. The most pronounced feature of abnormal cells is the alteration in chromosome numbers, with many cells surviving this process being aneuploid. The switch to abnormal chromosome numbers is usually referred to as cell transformation and this process may give rise to cells that can then be cultivated for indefinite periods of time by serial passaging. Transformed cells give rise to continuous cell lines.

In certain aspects of the instant invention, cells are cultured prior to contact with differentiating agents. They may also be cultured after contact, i.e., after they have been induced to differentiate toward a given or specific phenotype. Cells will be cultured under specified conditions to achieve particular types of differentiation, and provided various factors necessary to facilitate the desired differentiation.

H. STIMULATORY FACTORS

1. Cell Growth and Differentiation Factors

Cell growth and differentiation factors are molecules that stimulate cells to proliferate and/or promote differentiation of cell types into functionally mature forms. In some embodiments of the invention, cell growth and differentiation factors may be administered in combination with compounds of the present invention in order to direct the administered cells to proliferate and differentiate in a specific manner. One of ordinary skill would recognize that the various factors may be administered prior to, concurrently with, or subsequent to the administration of compounds of the present invention. In addition, administration of the growth and/or differentiation factors may be repeated as needed.

It is envisioned that a growth and/or differentiation factor may constitute a hormone, cytokine, hematapoietin, colony stimulating factor, interleukin, interferon, growth factor, other endocrine factor or combination thereof that act as intercellular mediators. Examples of such intercellular mediators are lymphokines, monokines, growth factors and traditional polypeptide hormones. Included among the growth factors are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factors-α and β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte/macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; IL-13, IL-14, IL-15, IL-16, IL-17, IL-18. As used herein, the term growth and/or differentiation factors include proteins from natural sources or from recombinant cell culture and biologically active equivalents of the native sequence, including synthetic molecules and mimetics.

2. Post-Stimulation Purification of Induced Cells

Following stimulation, it may be desirable to isolate stem cells that have been induced to undergo differentiation from those that have not. As discuss above, a variety of purification procedures may be applied to cells to effect their separation, and a number of these rely on cell surface markers.

i. Cardiomyocytes

U.S. Patent Publication No. 2005/0164382, incorporated herein by reference, describes methods of obtaining cardiomyocytes as well as various cardiomyocyte markers including cTnI, cTNT, ventricular myosin, connexin43, sarcomeric myosin heavy chain (MHC), GATA-4, Nkx2.5, N-cadherin, P1-adrenoceptor (β1-AR), ANF, MEF-2A, MEF-2B MEF-2C, MEF-2D creatine kinase MB (CK-MB), myoglobin, or atrial natriuretic factor (ANF).

ii. Neuronal Cells

A number of neuronal markers have been used to identify various classes of cells that are of neuronal origin. For example, glial fibrillary acidic protein and 5100 protein are used to identify astrocytes, GAP-43, microtubule associated protein 2 neuronal specific enolase, synaptophysin, tryptophan hydroxylase, β-tubulin and vimentin/LN6 are used to identify neuronal cells generally, and myelin basis protein can be used to identify oligodendrocytes.

I. CANCER STEM CELLS

Stem cells are functionally characterized by the ability to self renew and differentiate into distinct cell lineages. It has been established that embryonic stem (ES) cells, derived from the inner cell mass of the developing blastocyst, are pluripotent, undifferentiated cells with the potential to proliferate, self-renew, and generate new tissues. Such ES cells have now been isolated from both mouse and human embryos. In addition, stem cells have been identified within adult, differentiated tissues. These adult stem cells, sometimes also termed multi-potent adult progenitor cells (MAPCs), are believed to play essential roles in growth and tissue regeneration and have been identified in certain tissues, including the brain, epidermis, lung, breast, hematopoietic and neural systems. Gage, 2000; Abeyta et al., 2004; Tumbar et al., 2004; Zepeda et al., 1995; Dontu et al., 2003; Welm et al., 2002; Gudjonsson et al., 2002; Lagasse et al., 2001; Ramalho-Santos et al., 2002.

There is evidence that many common cancers, including skin and breast cancers, in addition to leukemias, can result from transforming events that occur in adult stem cells (Perez-Losada and Balmain, 2003; Al-Hajj et al., 2003; Reya et al., 2001). Indeed, functional parallels exist between tumorigenic and normal stem cells. Both cell types demonstrate significant proliferative potential, the ability to self-renew, and the ability to generate new tissues. However, tumorigenic stem cells lack the normal growth regulatory mechanisms that limit the uncontrolled proliferation of stem cells (Reya et al., 2001).

Tumorigenic stem cells arise in normal adult stem cell populations through the accumulation of multiple transforming mutations. As adult stem cells can persist and self-renew for the lifespan of the individual, these cells are more likely to accrue the genetic lesions necessary for malignant transformation. Such transformed tumorigenic stem cells, arising in normal adult stem cell populations, can initiate cancer development (Reya et al., 2001). Furthermore, tumorigenic stem cells may also play important roles in tumor evolution, metastatic invasion and local recurrence following treatment.

Cancer stem cells constitute only a small proportion of a tumor or a cancerous tissue. But the cancer stem cells have a unique ability to establish new colonies of cancer cells. For example, when mouse myeloma cells are obtained from mouse ascites, separated from normal hematopoietic cells, and put into in vitro colony-forming assays, only 1 in 10,000 to 1 in 100 cancer cells were able to form colonies (Park et al., 1971). Even when leukemic cells were transplanted in vivo, only 1-4% of cells could form spleen colonies (Bruce et al., 1963; Wodinsky et al., 1967; Bergsagel et al., 1968). Moreover it has been shown that a subset of cells from a population of seemingly homogeneous cancer cells is capable of proliferation and is clonogenic, while the remainder of cancer cells cannot undergo significant proliferation. Thus, workers have purified such a proliferative subset of leukemia cells as $CD34^+CD38^-$ cells from patient samples (Bonnet and Dick, 1997). Despite the fact that these cells represented a small and variable proportion of acute myelogenic leukemia cells (0.2% in one patient), they were the only cells capable of transferring acute myelogenic leukemia (AML) from human patients to NOD/SCID mice in the vast majority of cases. Thus, not all AML cells had a similar clonogenic capacity. Only a small, identifiable subset was consistently enriched for the ability to proliferate and transfer disease.

As used herein, a cancer stem cell is a stem cell that has a cancerous phenotype. Cancer stem cells lack the normal growth regulatory mechanisms that limit the controlled proliferation of stem cells. Cancer stem cells constitute only a subset of cells from a population of seemingly homogeneous cancer cells. While cancer stem cells are capable of proliferation and are clonogenic, most cancer cells in a population of seemingly homogeneous cancer cells cannot undergo significant proliferation.

As discussed herein, compounds of the present invention may be used to treat cancer. For example, compounds of the present invention may be used to target cancer stem cells. In certain embodiments, combination therapy may be employed, wherein a compound of the present invention is administered to a cancer patient in addition to other therapy, such as surgery, chemotherapy and/or radiation therapy, wherein the compound of the present invention targets primarily the cancer stem cells and the chemo- or radiation therapy targets primarily the non-stem cell cancer cells. Combination therapy is discussed further below. Compounds of the present invention may also find use in on-going treatment after other cancer therapy (e.g., surgery, chemo- and/or radiation therapy) has been terminated. This approach would be designed to suppress cancer stem cells from forming cancerous tumors, and/or encourage stem cells with cancerous predilections to instead form non-cancerous cells. Determining whether a cancer patient possesses cancer stem cells, and thus could be a candidate for receiving compounds of the present invention in therapeutically effective amounts, could be determined, for example, by methods described in U.S. Publ. Appl. No. 2005/0277162, wherein Rex-1 is described as a cancer stem cell marker.

Other uses of compounds of the present invention in a cancer context contemplate administration of a compound of the present invention to a patient having a cancerous tumor. Curative surgery includes resection in which all or part of cancerous tissue is physically removed, excised, and/or destroyed. Tumor resection refers to physical removal of at least part of a tumor.

In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

Accordingly, a compound of the present invention may be administered, for example, to treat a primary tumor, and following resection of the tumor, a compound of the present invention could continue to be administered to treat any residual, microscopic disease, be it comprised of cancer stem cells or cancer cells that are not stem cells. In this regard, treatment with a therapeutic amount of a compound of the present invention may increase the respectability of the tumor due to shrinkage at the margins or by elimination of certain particularly invasive portions. Additional treatments subsequent to resection may then serve to eliminate microscopic residual disease at the tumor site. The tumor may be a brain cancer tumor, for example.

Moreover, a compound of the present invention may be administered via placement of the compound directly at the site of the tumor bed such that the compound is released over time. For example, a compound of the present invention may be comprised in a wafer that is left in the tumor bed following resection of the tumor, wherein the wafer is attached to the edges of the resection cavity at the conclusion of surgical tumor removal. Such wafers have been employed in other contexts, such as biodegradable carmustine (BCNU) wafers for treatment of gliomas. Multiple wafers may be employed in such therapeutic intervention.

1. Combination Therapy

In certain aspects, a compound of the present invention may be used in combination with another agent or therapy method, e.g., another cancer treatment. Administration of a compound of the present invention may precede or follow the other agent treatment by intervals ranging from minutes to weeks. In embodiments where the other agent and the compound of the present invention are applied separately, one would generally ensure that a significant period of time did not expire between the time of each delivery, such that the agent and the compound of the present invention would still be able to exert an advantageously combined effect. For example, in such instances, it is contemplated that one may contact the cell, tissue or organism with two, three, four or more agents substantially simultaneously (i.e., within less than about a minute) with a compound of the present invention. In other aspects, one or more agents may be administered within about, at least about, or at most about 1 minute, 5 minutes, 10 minutes, 20 minutes 30 minutes, 45 minutes, 60 minutes, 2 hours, 3 hours, 4 hours, 5 hours, 6 hours, 7 hours 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, to, at least, or 48 hours or more prior to and/or after administering the compound of the present invention. In certain other embodiments, an agent may be administered within about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20, to 21 days prior to and/or after administering the compound of the present invention. In some situations, it may be desirable to extend the time period for treatment significantly, however, where several weeks (e.g., 1, 2, 3, 4, 5, 6, 7 or 8 weeks or more) lapse between the respective administrations.

Various combination regimens of the agents may be employed. Non-limiting examples of such combinations are shown below, wherein the compound of the present invention is "A" and the secondary agent, such as radiation or chemotherapy, is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of the compound of the present invention of the present invention to a patient will follow general protocols for the administration of chemotherapeutics, taking into account the toxicity, if any, of the conjugate. It is expected that the treatment cycles would be repeated as necessary. It also is contemplated that various standard therapies, as well as surgical intervention, may be applied in combination with the compound of the present invention. These therapies include but are not limited to chemotherapy, radiotherapy, immunotherapy, gene therapy and surgery.

J. METHODS OF TREATMENT

The present invention contemplates a variety of uses for the compounds of the present invention. In particular, they can be used to treat individuals that have undergone trauma, injury, disease or other destruction or damage to tissue, such as neuronal or cardiac tissue.

In one embodiment, the invention contemplates the administration of the compounds directly into an affected subject. Traditional routes and modes of administration may be utilized depending the clinical situation and the tissue target of the therapy. Alternatively, the invention may rely on an ex vivo approach, where stem cells are stimulated with compounds of the present invention outside an organism and then administered, optionally after culturing to expand the cells, to a recipient. The cells may be heterologous to the recipient, or they may have previously been obtained from that recipient, i.e. autologous.

In another embodiment, the present invention contemplates the use of compounds of the present invention to induce differentiation in cells that have become pathologically de-differentiated, i.e., hyper- or neoplastic cells, such as cancer cells. Particular embodiments of this aspect of the invention involved the treatment of individuals have neuronal cancers, such as gliomas and glioblastomas, including glioblastoma multiforme.

K. PHARMACEUTICAL COMPOSITIONS

It is envisioned that, for administration to a host, compounds of the present invention and stimulated/differentiated cells will be suspended in a formulation suitable for administration to a host. Aqueous compositions of the present invention comprise an effective amount of a compound and/or cells dispersed in a pharmaceutically acceptable formulation and/or aqueous medium. The phrases "pharmaceutically and/or pharmacologically acceptable" refer to compositions that do not produce an adverse, allergic and/or other untoward reaction when administered to an animal, and specifically to humans, as appropriate.

As used herein, "pharmaceutically acceptable carrier" includes any solvents, dispersion media, coatings, antibacterial and/or antifungal agents, isotonic and/or absorption delaying agents and the like. The use of such media or agents for pharmaceutical active substances is well known in the art. Except insofar as any conventional media or agent is incompatible with the active ingredient, its use in the therapeutic compositions is contemplated. Supplementary active ingredients can also be incorporated into the compositions. For administration to humans, preparations should meet sterility, pyrogenicity, general safety and/or purity standards as required by FDA Office of Biologics standards.

Compounds and/or cells for administration will generally be formulated for parenteral administration, e.g., formulated for injection via the intravenous, intramuscular, subcutaneous, intralesional, or even intraperitoneal routes. The preparation of an aqueous composition that contains cells as a viable component or ingredient will be known to those of skill in the art in light of the present disclosure. In all cases the form should be sterile and must be fluid to the extent that easy syringability exists and that viability of the cells is maintained. It is generally contemplated that the majority of culture media will be removed from cells prior to administration.

Generally, dispersions are prepared by incorporating the compounds and cells into a sterile vehicle which contains the basic dispersion medium and the required other ingredients for maintaining cell viability as well as potentially additional components to effect proliferation, differentiation or replacement/grafting in vivo. Upon formulation, solutions will be administered in a manner compatible with the dosage formulation or in such amount as is therapeutically effective. Some variation in dosage will necessarily occur depending on the condition of the subject being treated. The person responsible for administration will, in any event, determine the appropriate dose for the individual subject.

L. EXAMPLES

The following examples are included to demonstrate certain preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Identification of Certain Neurogenic-Inducing Compounds of the Present Invention Chemical Libraries and Medicinal Chemistry.

The UTSW compound library used in this screen was purchased in two components: 47,000 unique compounds selected from the DiverSet™ small-molecules library (ChemBridge, Inc; San Diego, Calif.) and 100,000 unique compounds from Chemical Diversity Labs, Inc. (San Diego, Calif.). This collection of compounds was additionally filtered to exclude compounds containing reactive groups and compounds likely to be insoluble or cytotoxic.

Assay Development.

An Nkx2.5-luc transgene was constructed by replacing the two coding sequence exons of Nkx2.5 locus from the ATG with the coding sequence of luc (from pGL3-basic vector, Promega) in an ~180,000 base pair-long BAC (FIG. 11). The recombinant BAC DNA was introduced into pluripotent P19CL6 cells using Lipofectamine-2000 (Invitrogen) and neo$^R$ clones were selected, and tested for chemically inducible luc activity with sodium butyrate (NaB). #5-1, a clonal stem cell line with low basal and at least a 4-fold higher NaB-inducible luciferase activity compared to vehicle control (DMSO), yielding a Z' value of ~0.7 in 384-well plate format (Zhang et al. 1999), was chosen for the HTS.

HTS for Chemical Inducers of Nkx2.5-Luc in P19CL6.

Approximately 147,000 unique compounds were screened using clone #5-1 P19CL6 Nkx2.5-luc cells in 384-well white plates. To ensure pluripotency at the time of compound screening, each P19CL6 #5-1 cell batch was pre-screened for uniform high-level Oct3/4 expression by immunofluorescence cell staining. Cells were plated using an automated dispenser at 1,200 cells/well in 70 µL media/well in 10% fetal calf-serum MEMα media. Parallel plating onto clear-bottom plates was done to ensure the viability and appropriate cell density for large-scale screens. On day 3, 0.7 µL of library compounds at 5 µM in pure DMSO (1% final DMSO concentration) was dispersed robotically (384-pin array Biomek FX high-precision robot) and the plates were incubated for an additional 48 hours before measuring luc activity.

Primary and Secondary Screening Hit Selection.

Screening the entire 147,000 UTSW compound library at 5 µM with clone #5-1 reporter cells resulted in ~3,000 primary "hits," using a luc activity of >2 times the plate median as the cut-off for positive score. Secondary screening using #5-1 cells at 1.7, 5, and 15 µM identified 66% of these hits as repeat positives, and from these positive hits, the inventors placed 150 compounds with the best dose response into a candidate hit list. Among these candidates, 10 major sub-groups with common core structural motifs emerged, as shown below.

Top-10 Hit List

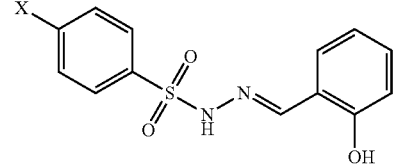

Biaryl sulfonyl-hydrazones
(N = 4)

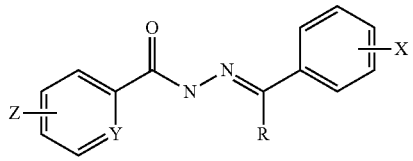

Y = N, CH
Biaryl acyl-hydrazones
(N = 6)

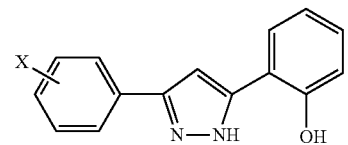

3,5-disubstituted pyrazoles (N = 4)

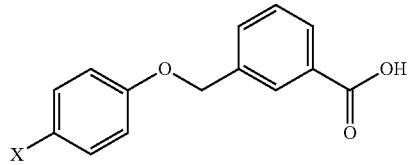

Aryl ether benzolc acids (N = 6)

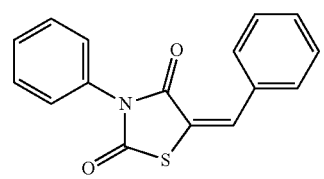

Thiazolidinediones (N = 2)

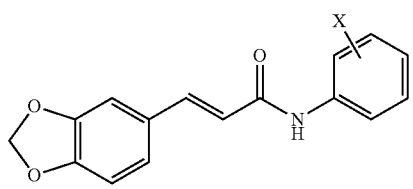

Cinnamic amides (=2)

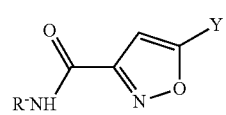

3,5-disubstituted isoxazoles (N = 5)

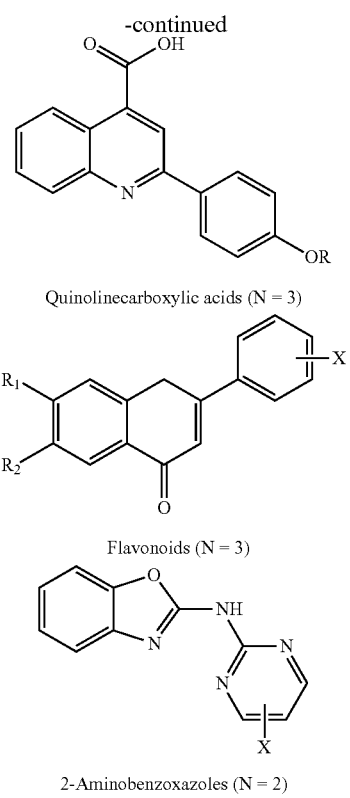

Quinolinecarboxylic acids (N = 3)

Flavonoids (N = 3)

2-Aminobenzoxazoles (N = 2)

Each of these compound families was independently identified multiple times in the primary screen using Nkx2.5-luc P19CL6 cells, and then re-identified in a secondary, confirmatory screen using the same reporter cells. X, Y, R, $R_1$, $R_2$ are additional chemical side groups.

Example 2

Synthesis of Certain Compounds of the Present Invention

Synthesis of 3,5-Disubstituted Isoxazoles.

Two approaches based on known literature procedures (Jager and Colinas, 2003; Grunanger and Vita-Finzi, 1991; Cicchi et al., 2003) were used to synthesize certain compounds of the present invention.

General Procedure A: 3+2 Cycloaddition Route to Isoxazole Core.

To a stirred suspension of ethyl chlorooximido acetate (3.0 mmol) and the corresponding alkyne (1.0 mmol) in THF (5 mL) was added triethylamine (4 mmol) dropwise at room temperature. The reaction was monitored by LC/MS analysis for conversion to the isoxazole. After 24 hrs, the reaction was diluted with water (2 mL) and ethyl acetate (2 mL). The organic layer was washed with brine (2 mL) and dried over $Na_2SO_4$. Concentration gave an oil that was purified by silica gel chromatography to yield the corresponding ethyl 5-(aryl) isoxazole-3-carboxylate (30-50% yield).

General Procedure B: Cyclodehydration Route to Isoxazole Core.

To a stirred solution of dimethyl oxalate (3.3 mmol) and the corresponding aryl ketone (3.0 mmol) in toluene (10 mL) was added a 1.0M solution of potassium tert-butoxide in THF (3.5 mmol) dropwise. The corresponding reaction was monitored by LC/MS for conversion to the corresponding methyl 2,4-dioxo-4-arylbutanoate. Once the reaction was complete, it was quenched with 1N HCl (5 mL). The organic layer was washed with brine (10 mL) and dried to a crude solid. The crude product was then directly treated with hydroxylamine hydrochloride (4 mmol) in MeOH at 50° C. for 4-6 hours. The resulting methyl 5-(aryl)isoxazole-3-carboxylate was isolated by direct crystallization using water as the anti-solvent (60-70% yield).

Hydrolysis of Isoxazole Esters:

From either Procedure A or B, the isoxazole esters obtained were hydrolyzed using 1N LiOH (2 equiv) in THF at 50° C. for the appropriate amount of time as indicated by LC/MS analysis. Once the reaction was complete, the reaction was extracted with toluene. The resulting aqueous layer was then acidified to pH=1 with 1H HCl and extracted with EtOAc. Concentration gave a crude solid that was taken directly into the next step.

Amide Coupling Step:

The crude isoxazole acids (1 mmol) were dissolved in dichloromethane (3 mL) along with 1-ethyl-3-(3-dimethylaminopropyl)-carbodiimide (EDC) (1.1 mmol) and 1-hydroxybenzotriazole hydrate (HOBt) (1.1 mmol). After stirring for 10 minutes at room temperature, the corresponding amine (1.2 mmol) was added in dropwise. The reaction was monitored by LC/MS for amide formation. Once the reaction was complete, the solvent was removed the crude reaction was partitioned between water (2 mL) and EtOAc (3 mL). The EtOAc layer was washed with brine (2 mL) and concentrated to give the crude product. The products can either be purified by silica gel chromatography or by crystallization from ethanol/water. Typical yields were 60-80%.

Example 3

Synthesis of Particular Compounds of the Present Invention

N-cyclopropyl-5-(thiophen-2-yl)isoxazole-3-carboxamide

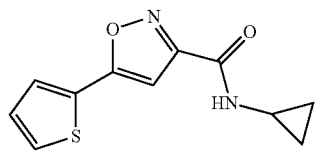 [SMILES: O=C(NC1CC1)c1cc(-c2cccs2)on1]

To a solution of ethyl 5-(thiophen-2-yl)isoxazole-3-carboxylate (220 mg, 1 mmol) in absolute ethanol (5 mL) was added cyclopropylamine (285 mg, 5 mmol). The reaction was sealed and heated to 80° C. for 24 hours. The reaction was allowed to cool to room temperature and water (1 mL) was added. The product was collected by vacuum filtration as a white crystalline solid (150 mg, 64% yield). $\delta_H$ (400 MHz, $d^6$ DMSO): 8.85 (1H, d), 7.83 (1H, d), 7.76 (1H, d), 7.24 (1H, d), 7.18 (1H, s), 2.83 (1H, m), 0.58-0.71 (4H, m).

Synthesis of Certain Isoxazoles and Pyrazoles of the Present Invention

Generally:

The synthesis of certain isoxazoles and pyrazoles starts with the reaction of an aromatic ketone (i.e., acetophenone) with an appropriate base (i.e., potassium tertbutoxide) to generate the corresponding enolate in a suitable solvent such as tetrahydrofuran. This enolate is trapped in situ with an electrophile such as dimethyloxalate to yield the corresponding methyl-2,4-dioxo-phenylbutanoate derivative. This derivative can then be reacted with hydroxylamine hydrochloride to generate the corresponding isoxazole or hydrazine to generate the corresponding pyrazole usually in a polar protic solvent (i.e., methanol). The methyl ester of either the isoxazole or pyrazole can be hydrolyzed to the carboxylic acid using an appropriate base such as aqueous lithium hydroxide and suitable organic solvent (i.e., tetrahydrofuran). Under standard peptide type coupling conditions (EDC, HOBt, amine), the acid can be converted to the desired amide using a suitable aprotic solvent such as dichloromethane. The products can then be purified using standard protocols that would be familiar to those of ordinary skill in the art.

Synthesis of N-cyclopropyl-5-(2-hydroxyphenyl-isoxazole-3-carboxamide

Step 1. Synthesis of methyl 4-(2-hydroxyphenyl)-2,4-dioxobutanoate (2)

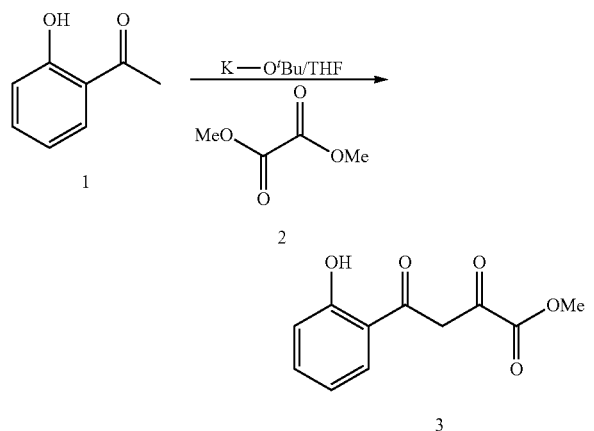

To a stirred solution of 2-hydroxyacetophenone (1, 2.0 mmol) and dimethyloxalate (2, 2.2 mmol) in toluene (10 mL) was added dropwise a solution of potassium tert-butoxide in THF (4.5 mL of a 1.0 M solution in THF) at room temperature. The reaction was monitored by HPLC analysis for complete consumption of the starting acetophenone. Once the reaction was complete (~60 min), it was quenched with a 1.0 N solution of HCl (5.0 mL) and the resulting biphasic mixture was stirred for ~10 minutes. After phase separation, the aqueous layer was removed. The organic layer was then washed with water (2 mL) and brine (2 ml) then dried over Na₂SO₄. The dried organic layer was then concentrated in vacuo to give a light yellow solid (350 mg, 79% yield) that was used "as is" in the next step.

Step 2. Synthesis of methyl 5-(2-hydroxyphenyl)isoxazole-3-carboxylate (4)

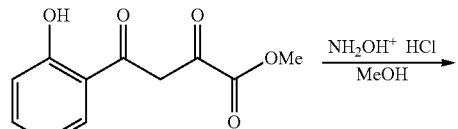

-continued

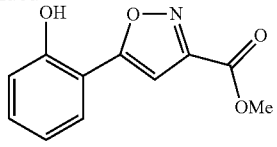

To a 20 mL flask was added the diketone 3 (110 mg, 0.5 mmol) and hydroxylamine hydrochloride (35 mg, 0.5 mmol). Methanol was then added (7 mL) and the mixture was heated to reflux. The reaction was monitored by HPLC for product formation. Once the reaction was complete (~18 hours), the reaction was concentrated in vacuo to a crude yellow oil. This oil was partitioned between EtOAc (5 mL) and water (2 mL). The aqueous layer was discarded and the organic layer was washed with water (2 mL), brine (2 mL) and then dried over Na₂SO₄. The solution was then concentrated to an oil which solidified upon standing to give the desired product 4 (85 mg, 77.6% yield) and used "as is" in the next step.

Step 3. Synthesis of 5-(2-hydroxyphenyl)isoxazole-3-carboxylic acid (5)

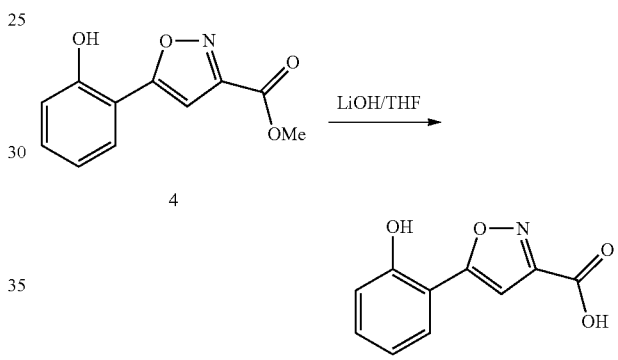

To a stirred solution of methyl ester 4 (32 mg, 0.15 mmol) in THF (2 mL) was added a solution of 1.0 M LiOH (2 mL) in one portion. The corresponding reaction was monitored by HPLC for consumption of the starting material. After 3 hours at room temperature, the reaction was complete. To the reaction was added EtOAc (2 mL) and water (2 mL) and the layers were allowed to separate. The aqueous layer was transferred to clean flask and then acidified to pH=1 using 2.0 N HCl. This was then extracted with EtOAc (5 mL) and the aqueous layer was discarded. The organic layer was washed with water (2 mL) and brine (2 mL) followed by drying over Na₂SO₄. Concentration gave 20 mg (65% yield) of the desired product 5 that was used "as is" in the next step.

Step 4. Synthesis of N-cyclopropyl-5-(2-hydroxyphenyl)isoxazole-3-carboxamide (6)

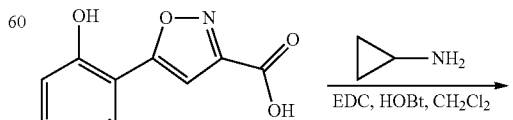

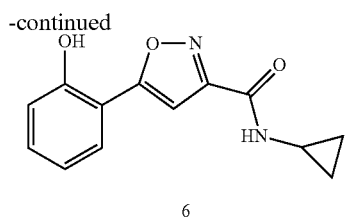

6

To a 20 mL flask was added the crude acid from step 3 (20 mg, 0.1 mmol), HOBt (16 mg, 0.12 mmol), and EDC (23 mg, 0.12 mmol). To this was added dichloromethane (3 mL) and the resulting heterogeneous mixture was stirred for 30 minutes at room temperature. To the resulting solution was added cyclopropylamine (9.0 mg, 0.15 mmol) and the reaction was monitored by HPLC for product formation. After 2 hours, the reaction was complete and concentrated to a thick oil. This oil was partitioned between EtOAc (3 mL) and water (2 mL) with stiffing for 10 minutes. The layers were then allowed to separate and the aqueous layer was discarded. The organic layer was then washed with water (2 mL), brine (2 ml) and dried over $Na_2SO_4$. Concentration gave an oil that was purified by column chromatography (30% EtOAc in hexanes) to give 6.1 mg (25% yield) of the desired isoxazole 6; $^1$H NMR (400 MHz, d6-DMSO) S 8.85 (d, 1H), 7.78 (d, 1H), 7.32 (t, 1H), 7.08 (s, 1H), 7.01 (d, 1H), 6.94 (t, 1H), 2.82 (m, 1H), 0.67 (m, 2H), 0.59 (m, 2H). LC/MS (electrospray ionization, positive mode) M+H=245.0.

Example 4

Materials and Methods

Reporter Gene Assay.

All reporter gene assays were done in 96-well format, and each data point represents the average of 12 replicates. Reporter genes included neuroD-, gIuR2-, MREx3-, NR1-, and pHDAC5:14-3-3-luciferase and each well contained ~25,000 cells in a volume of 100 μl. $5 \times 10^6$ HCN cells were transfected with 5 μg DNA by electroporation (Amaxa) and plated in growth media overnight. In the case of pHDAC5:/4-3-3-luciferase, cells were transfected with 2 μg of each plasmid. Compounds were added the day following transfection and luciferase assays were performed 24 or 48 h later. The typical dose of Isx-9 in reporter assays was 20 μM unless noted otherwise.

Neural Stem Cell Culture, In Vitro Differentiation, and CaMK Inhibitor Studies.

The hippocampal neural stem/progenitor (NSC) line used in this study (HCN cells) were originally isolated from adult (8-10 wks old) female Fisher 344 rats and have been characterized previously (Gage et al., 1995; Palmer et al., 1997). HCN cells were cultured in DMEM:F12 (Omega Scientific) with N2 supplement (Invitrogen) and basic fibroblast growth factor (20 ng/ml FGF-2) (PeproTech). The mouse whole brain neural stem/progenitors (MWB) were derived from adult (8-10 wks old) C57BL/6 mice that have been characterized previously (Ray and Gage, 2006). The P19CL6 cells is a sub-line of P19EC cells, originally generated by the late Dr. Habara-Ohkubo (Habara-Ohkubo, 1996), were grown in MEM-α (Invitrogen) containing 10% fetal bovine serum (Omega). HCN cells or MWB neural progenitors were trypsinized and plated into N2 medium (Invitrogen) containing FGF-2 (HCN cells) or FGF-2/EGF/heparin (MWB) overnight, and switched to fresh N2 medium without FGF-2 and Isx-9 (20 μM for HCN cells and 5 μM for MWB) was added for 4 d. To test if Isx-9 could block competing astrocyte or oligodendrocyte differentiation, standard gliogenic conditions were used as described previously (Hsieh et al., 2004). To induce neuronal differentiation of P19CL6 cells, 1 μM all-trans retinoic acid (RA) was added to the culture media to form P19CL6 aggregates for 2-4 d, then media was replaced with fresh N2 medium and 10 μM Isx-9 was added for 4 d. In some cultures, BrdU (10 μM, Sigma) was added to label dividing cells 1 h prior to fixation, propidium iodide (1 μg/ml, Molecular Probes) or Hoescht 33342 (1 μg/ml, Sigma) were added to label dead or all cells, and Q-VD-OPh (2 μM, Enzyme Systems Products) was used to block caspase-mediated apoptosis. Staining of live (rather than fixed) cultures was used to avoid underestimating cell death because of possible detachment of dying and/or dead cells from culture substrates. For CaMK/PKC inhibitor experiments, HCN cells were pre-treated with inhibitors (KN93 [10, 5, and 1 μM], KN92 [10, 5, and 1 μM] or G66976 [200 nM]) for 2 h, and 20 μM Isx-9 was added for 24 or 48 h.

RT-PCR and Protein Blotting.

Total RNA was isolated by Trizol reagent (Invitrogen) and RT-PCR was carried out as previously described (Hsieh et al., 2004b). Primer sequences are available upon request. For protein blotting, whole cell lysates were prepared from HCN cells cultured in undifferentiated conditions (FGF-2 or DMSO vehicle control) or from differentiating conditions (Isx-B).

Protein Blotting, Immunoprecipitation, and Gel Shift Assay.

For protein blotting analysis, whole cell lysates were prepared from HCN cells using RIPA buffer (Tris-HCl, 50 mM, pH 7.4; NP-40, 1%; Na-deoxycholate, 0.25%; NaCl, 150 mM; EDTA, 1 mM; PMSF, 1 mM; aprotinin, leupeptin, pepstatin, 1 mg/ml; $Na_3VO_4$, 1 mM; NaF, 1 mM). For nuclear and cytoplasmic extracts, HCNs were lysed in hypotonic buffer (Hepes, 10 mM, pH 8; $MgCl_2$, 1.5 mM; KCl, 10 mM; DTT, 1 mM). Nuclei was then isolated and resuspended in the same buffer with NaCl, 420 mM; EDTA, 0.2 mM; glycerol, 25%; NP-40, 1%; PMSF, 1 mM; aprotinin, leupeptin, pepstatin, 1 mg/ml. Protein concentration in centrifugation-clarified cell lysates were measured by the BCA Protein Assay Kit (Pierce) and equal amounts of protein were separated on a 4-12% SDS-PAGE and transferred to Hybond PVDF (Amersham Biosciences). Protein blots were done using the NuPage gel and transfer system with 4-20% Tris-Bis gels (Invitrogen). Primary Abs for protein blotting included: rabbit anti-βTubIII (1:1000; Covance), mouse anti-Map2AB (1:100; Sigma); goat anti-doublecortin (DCX) (1:100; Chemicon), mouse anti-GAPDH (1:5000; Chemicon), rabbit anti-MEF2A (1:500; Upstate), rabbit anti-MEF2C (1:500; Santa Cruz); rabbit anti GluR2/3 (1:250; Chemicon); rabbit anti-phosphorylated HDAC5 (1:500; gift from T. McKinsey); rabbit anti-HDAC5 (1:500; Upstate), rabbit anti-HDAC4 (1:500; Cell Signaling), rabbit anti-CREB (1:100; Cell Signaling); mouse anti-FLAG (1:5000; Sigma), mouse anti-GFP (1:500; Invitrogen); rabbit anti-phosphorylated CamKII (1:200; Cell Signaling). Immunoreactive bands were visualized using HRP- or AP-conjugated secondary antibodies, followed by ECL (Amersham Biosciences) or BCIP/NBT detection (KPL, Gaithersburg, Md.). Immunoprecipitation of FLAG-tagged HDAC5 was done with the FLAG antibody and blotting for phospho-HDAC5 and Flag antibodies, or CREB and GFP as a normalization control. For electrophoretic mobility shift assay (EMSA) experiments, labeling of 10 pmol double-stranded oligonucleotides was performed by Klenow fill in of overhanging 5' ends with $^{32}$P-dCTP and purification with a Sephadex G50 column. Binding reactions of 1× binding buffer (40 mM KCl, 15 mM HEPES pH 7.0, 1 mM EDTA, 5% glycerol), 0.5 mM DTT, 10 µg lysate, 1 µg poly dI-dC and competitor DNA (100-fold excess) were incubated at room temperature for 10 min before addition of probe, incubated an additional 20 min and electrophoresed on a 6% polyacrylamide-TBE gel. For visualization, the gel was dried and exposed with an intensifying screen for 6 hours at −80° C.

Immunostaining, GFP-HDAC5 Visualization, and Fluorescence Microscopy.

Labeled cells were visualized using a Nikon TE2000-U inverted microscope (Nikon, Inc.) and a CoolSnap digital camera (Photometrics, Inc.). Quantification of cell phenotype was done by sampling 6-8 random fields in each well and counting a total of 250-500 cells at 20× magnification. 4',6-diamidino-2-phenylindole (DAPI) was used to identify individual cells. For quantification of live/dead cells, images were taken of cultures live-stained with propidium iodide and Hoescht 33342 at 20× magnification, and 500-1000 cells were counted by sampling 6-8 random fields in each well. For quantification of HDAC5 subcellular localization, 20× images were taken of live cultures, and 40-50 GFP+ cells were counted by sampling 3 random fields in each well. The following primary antibodies were used: rabbit anti-Tuj1 (1:7500; Covance), mouse anti-Map2ab (1:250; Sigma); guinea pig anti-GFAP (1:2500; Advanced Immunochemical, Inc.) and rat anti-BrdU (1:400; Accurate). Secondary antibodies were all from Jackson ImmunoResearch and used at 1:250 dilution. The detection of BrdU in cultured cells required treatment in 2N HCl at 37° C. for 30 min (Palmer et al., 1999).

Adenoviral Infection.

NPCs or Cos cells were infected with adenovirus at a multiplicity of infection of 10 particles/cell for 24 or 48 hours. For reporter gene experiments, NPCs were electroporated with luciferase constructs and mixed with virus before plating in N2 medium with FGF-2. After 48 hours, cells were replaced with N2 medium containing Isx compounds and cultured for an additional 24 hours. To visualize GFP on glass slides, NPCs were plated in N2 medium with FGF-2 and infected with adenovirus for 48 hours, then media was replaced with N2 medium plus vehicle or Isx, and cultured for an additional 24 hours. In some experiments, Cos cells were plated in IMDM medium (Invitrogen) containing 10% FBS and infected with adenovirus, and cultured for an additional 24 hours.

$Ca^{2+}$ Imaging.

HCN cells were loaded with 5 µM Fura2-AM (Molecular Probes) in artificial cerebrospinal fluid (ACSF) (140 mM NaCl, 5 mM KCl, 1 mM $MgCl_2$, 2 mM $CaCl_2$, 10 mM HEPES (pH 7.3) for 45 min at 37° C. For imaging experiments the coverslips were mounted onto a recording/perfusion chamber (RC-26G, Warner Instrument) maintained at 37° C. (PH1, Warner Instrument) positioned on the movable stage of an Olympus IX-70 inverted microscope, and perfused with ACSF media by gravity flow. Compounds (Isx 20 µM) or DMSO (vol/vol) were added and recording was started (time 0). For Isx-9 plus inhibitor experiments, HCNs were pre-treated with a "cocktail" inhibitor (5 µM each of AP5/CNQX/Nifedipine) or 2 µM MK801 for 5 minutes before Isx-9 treatment. Cells were intermittently excited by 340 nm and 380 nm UV light (DeltaRAM illuminator, PTI) using a Fura-2 dichroic filter cube (Chroma Technologies) and a 60×UV-grade oil-immersed objective (Olympus) and collected at 10 sec intervals and shown as 340/380 ratios at timepoints as indicated in FIG. 3.

GFP-HDAC5 and MEF2C-Engrailed Experiments.

For GFP-HDAC5 experiments, HCN cells were infected with adenovirus at a multiplicity of infection of 10 particles/cell for 24 or 48 h. For reporter gene experiments, HCN cells were electroporated with luciferase constructs and mixed with virus (GFP-HDAC5 (SA) or CMV-GFP control virus) before plating in N2 medium with FGF-2. After 48 h, cells were replaced with N2 medium containing 20 µM Isx-9 and cultured for an additional 24 h. To visualize GFP on glass slides, HCNs were plated in N2 medium with FGF-2 and infected with adenovirus for 48 h, then media was replaced with N2 medium plus vehicle or 20 µM Isx-9, and cultured for an additional 24 h. For MEF2C-engrailed experiments, HCN cells were co-electroporated with two DNA constructs: 3 µg of the MEF2C-engrailed plasmid (CAG-MEF2C-engrailed-IRES-GFP) or GFP control plasmid (CAG-GFP) plus 2 µg of the NR1-luc reporter plasmid. GFP expression was visualized 48 h after electroporation to confirm >50% transduction efficiency before adding compounds and luciferase assays were performed an additional 24 h later.

Statistical Analysis.

Results were analyzed for statistical significance using two-tailed Student's t test and all error bars are expressed as standard deviations (SD). Values of $p<0.05$ were considered significant.

Example 5

Results Relating to Example 4

Isoxazole-Induced Neuronal Differentiation in Adult Hippocampal Neural Stem/Progenitor Cells.

The inventors screened a pre-selected collection of synthetic small organic molecules (Sadek et al., manuscript submitted) for compounds that could chemically activate the neuronal gene program in P19 embryonal carcinoma cells using semi high-throughput luciferase assays as described in Examples 1 and 3. Among the candidate small molecules capable of inducing our neuronal reporter gene, neuroD, a key bHLH transcription factor involved in neuronal cell fate determination and differentiation, the inventors identified several compounds belonging to the structural class of 3,5-disubstituted isoxazole (Isx), molecules not previously associated with biological activity. Isx treatment induced at least a 8-fold increase in both NeuroD and GluR2 luciferase reporters, compared to a modest 2-fold increase in reporter activity with the pleiotropic chemical inducers retinoic acid and forskolin, until now gold standards for neuronal induction.

Isoxazoles at 20 µM concentration were effective inducers of neuronal differentiation in NPCs within 4 days, inducing morphological changes such as cell clustering, cell flattening and extension of processes, and induction of neuronal lineage-specific markers like TuJ1 and Map2ab, when compared to control cells treated with vehicle alone. Morphological changes became evident within hours of drug exposure, while an increase in the percentage of Tuj1+ neurons dramatically increased between 1 and 4 days compared to vehicle alone. NPCs that differentiated into definitive neuronal cells were scored on the basis of morphological criteria (elaboration of neuronal processes), as well as immunoreactivity with various neuronal markers (e.g., Tuj1). Isx treatment could also efficiently convert undifferentiated pluripotent embryonic stem cells (P19 embryonal carcinoma) as well as adult mouse whole brain (MWB) neural progenitors, suggesting that neuronal differentiation by isoxazoles is not just specific to adult rat hippocampal NPCs.

In addition to promoting neuronal differentiation, Isx dominantly suppressed glial differentiation in NPCs, even in the presence of strong gliogenic signals such as LIF and BMP2. 50 ng/ml LIF and 50 ng/ml BMP2 normally induced the differentiation of NPCs in 4-day cultures into Tuj1+ neurons and GFAP+ astrocytes, however treatment of cells with Isx completely suppressed astrocyte differentiation, and instead promoted neuronal differentiation. Moreover, Isx treatment also suppressed IGF-I induced oligodendrocyte differentiation. Taken together, these data suggest that Isx is a potent activator of the neurogenic lineage in stem cells.

Using semi-quantitative reverse transcriptase polymerase chain reaction (RT-PCR), the inventors observed increased neuroD, GluR2, β III-tubulin (Tuj1) and NMDA receptor subunit 1 (NR1) mRNA levels, all genes associated with neuronal commitment, differentiation, and/or maturation. Indeed, by mRNA, significant changes in gene expression were evident even after 3 hours of Isx treatment. Notably, many of these neuronal transcripts tested were highest at 1 day, with lower levels by 4 days, suggesting a temporal regulation of neuronal gene expression by Isx. Gapdh levels did not change with Isx treatment and was used as an internal control. Furthermore, the inventors never observed the expression of astrocytic and oligodendrocytic markers in the presence of Isx Isx treatment also induced a gradual increase in the level of neuronal protein expression over time, including βTUBIII and Doublecortin (DCX), which are expressed in immature neurons, as well as microtubule associated protein-2AB (Map2AB), which is expressed in more mature neurons. Neuronal protein expression was normalized for total protein concentration as well as to GAPDH. These data strongly support that Isx small molecules acts specifically and dominantly to induce neuronal differentiation and suppress glial differentiation.

Isoxazole-Induced Neuronal Differentiation is Due to Instructive Effects and a Subsequent Proliferation of Committed Neuroblasts.

Although these results established Isx as an inducer of neuronal differentiation of multipotent NPCs, it is important to assess the instructive versus selective effects of Isx. Stem cells can self-renew to give rise to more stem cells, or commit to a particular lineage and differentiate into cells of a mature phenotype, or die, and Isx may mediate a net increase in neuronal cells by acting at multiple levels. The results suggest a biphasic response of NPCs to Isx treatment: (1) the initial cell death associated with Isx-treatment and FGF-2 withdrawal does not distinguish between neuronal and non-neuronal cells within the first two days, and (2) continued Isx treatment might additionally promote the survival of differentiated neurons, in addition to inducing neuronal cell fate choice.

Next, the inventors determined whether proliferation of progenitors might contribute to the Isx-mediated neuronal differentiation. There was a gradual decrease in dividing cells in vehicle-treated cultures over time, most likely due to FGF-2 withdrawal. In contrast, Isx-treatment exhibited an initial drop in BrdU incorporation compared to vehicle controls (~10% compared to ~40% on the first day), suggesting that Isx does not have a major proliferation effect on NPCs. Interestingly, Isx-treated progenitor cells did show a slight increase in BrdU cells between 1 and 2 days, suggesting that there might be a secondary effect of Isx on NPC proliferation.

To determine if Isx has an effect on cells already committed to the neuronal lineage but still retained the ability to divide (neuroblasts), the inventors assessed the proliferation of Tuj1+ cells with Isx treatment. Indeed, an increase in the number of Tuj1+ cells that were also BrdU+ with Isx during the 4-day period was observed. Vehicle treated cultures did not produce BrdU+ cells that were also Tuj1+, while a significant number of Tuj1+ cells in Isx-treated cultures were BrdU+, suggesting that Isx-mediated neuronal differentiation is due to instructive effects on neuronal cell fate, as well as a subsequent proliferation of committed neuroblasts.

Isoxazole Treatment Triggers the Release of Intracellular $Ca^{2+}$ in NPCs.

At the core of the 3,5-disubstituted Isx small molecule is a chemical structure shared by molecules known to affect neurotransmission, such as α-amino-3-hydroxy-5-methyl isoxazole-4-proprionic acid (AMPA) and 5-aminomethyl-3-hydroxy-isoxazole (Muscimol). Treatment of NPCs with 25 µM AMPA or 50 µM Muscimol failed to induce morphologic neuronal differentiation, although there was some neuronal gene activation as evidenced by an increase in neuroD-luciferase activity and GluR2/3 protein expression with 15 or 50 µM Muscimol, respectively, suggesting that there may be a degree of specificity of Isx neurotransmitter-like effects in stem/progenitor cells. Based on studies by others, the inventors hypothesized that Isx might also regulate $[Ca^{2+}]_i$ levels in NPCs. The relatively slow kinetics of $[Ca^{2+}]_i$ release after Isx treatment, compared to other strong inducers of $[Ca^{2+}]_i$ such as ionomycin, was reminiscent of transcription factor activation consistent with "excitation" of NPCs leading to neuronal gene expression and neurogenesis. Indeed, the inventors did observe a small but significant decrease in NeuroD-luciferase in NPCs treated for 24 hours with Isx plus cocktail inhibitor (P=0.0002) as well as Isx plus MK801 (P=0.0003), suggesting that the Isx-mediated $Ca^{2+}$ release involved the concerted actions of high-voltage $Ca^{2+}$ channels as well as NMDA receptors.

Isx-Mediated Neuronal Differentiation is Coupled to MEF2 Activation in NPCs.

A number of transcription factors, including CREB, NFAT, and MEF2 are activated by a slow and sustained release of intracellular $Ca^{2+}$ in neuronal cells. Thus, the inventors next assessed Isx effects on a set of $Ca^{2+}$-activated reporter transgenes. NFAT and MCIP are two cellular transcription factors regulated by the $Ca^{2+}$-activated phosphatase, calcineurin. To monitor NFAT and MCIP activities, they used luciferase reporters bearing the NFAT and MCIP regulatory regions (NFAT- and MCIP-luc). They observed a strong induction of both NFAT- and MCIP-luc with 24 hours of Isx treatment. The induction of NFAT and MCIP by Isx was dependent on calcineurin activity, since treatment of NPCs with two calcineurin inhibitors, FK506 (1.25-20 µM) and CsA (1.25-20 µM), blocked Isx activation in a dose-dependent manner.

Isoxazoles were originally identified in a cardiogenic small molecule screen of pluripotent embryonal carcinoma cells (P19CL6), based on the activation of the NK-2 class homeodomain protein (Nkx2.5) (Sadek et al., manuscript submitted). In light of Nkx2.5 role in neuronal cell differentiation, the inventors confirmed that Isx treatment triggered the activation of a rat Nkx2.5-luciferase transgene in NPCs. Recently, it was suggested that Nkx2.5 and myocyte enhancer factor-2C (MEF2C) could reciprocally regulate each other's expression and induce cardiogenesis in P19EC cells, as well as neurogenesis in P19 cells. Moreover, $Ca^{2+}$ signaling strongly influences the activity of MEF2 proteins through voltage-sensitive $Ca^{2+}$ channels triggering phosphorylation and calcineurin-mediated dephosphorylation leading to MEF2-dependent transcription, and calcineurin has recently been shown to control neuronal synapse formation via a MEF2-regulated transcriptional mechanism. The inventors thus examined whether there was a connection between Isx-mediated neuronal differentiation and MEF2. Indeed, Isx treatment induced a MEF2 promoter as compared to vehicle alone, and was blocked by calcineurin inhibitors FK506 and CsA in a dose-dependent manner similar to what was seen with NFAT and MCIP.

To further examine the role of MEF2 proteins in NPCs, the inventors determined the levels of MEF2 isoforms in NPCs treated with Isx for 2- and 4-days, compared to vehicle treatment. There are four MEF2 isoforms in all, with MEF2A, 2C, and 2D having the highest expression in the adult brain. MEF2C mRNA levels, and to a lesser extent MEF2A, appeared to be up-regulated with Isx treatment, suggesting a possible role of MEF2A and 2C in neuronal lineage progression of NPCs. Despite the increase in mRNA levels, the inventors did not observe an induction of MEF2A or 2C protein after Isx treatment up to 64 hours, which is the timeframe that neuronal differentiation is occurring as evident the expression of two mature neuronal markers Map2AB and GluR2/3.

MEF2 Activation is Due to Phosphorylation and Export of HDAC5.

Post-transcriptional/translational regulation of MEF2 is commonly mediated by CaMK-mediated phosphorylation, calcineurin-dependent dephosphorylation, calreticulin-dependent translocation into the nucleus, and/or through its interaction with class II histone deacetylases (HDACs). Unlike MEF2A and 2C mRNA levels that were induced with Isx treatment, the activation of MEF2 by isoxazoles did not appear to be regulated at the level of phosphorylation or dephosphorylation or translocation since MEF2A and MEF2C protein levels are relatively unchanged between nuclear or cytoplasmic fractions with drug treatment. The inventors thus considered the possibility that MEF2 activity was controlled by epigenetic mechanisms, held in a repressed state in NPCs through its interaction with class II HDACs.

There are three classes of histone deacetylases (HDACs) expressed in vertebrates. Class I HDACs are ubiquitously expressed, whereas class II HDACs have tissue-specific patterns of expression with highest levels in brain, heart and skeletal muscle. Class III HDACs are related to the Sir2 family proteins in yeast. Importantly, recent findings show that class IIa HDACs (HDAC-4, -5, -7, and -9) act as signal-responsive repressors of cardiac hypertrophy and that hypertrophic stimulus induced phosphorylation of class II HDACs in a $Ca^{2+}$/calmodulin kinase (CaMK) dependent fashion that causes export from the nucleus resulting in derepression of target gene expression. To examine the subcellular distribution of HDAC5 in NPCs, the inventors took advantage of a phospho-specific HDAC5 antibody. NPCs treated with vehicle or Isx for 1 day have similar levels of phos-HDAC5 in the nucleus, whereas higher levels of phos-HDAC5 in the cytoplasm are observed with Isx treatment while total HDAC5 levels are unchanged. Next, the inventors observed that Isx treatment slightly increased cytoplasmic accumulation of HDAC4, whereas phospho-HDAC4 (using an antibody that cross-reacts with phospho XX of HDAC4) did not appear to change or increase with drug treatment and remained cytoplasmic, suggesting that phosphorylation of HDAC5 compared to HDAC4 was more sensitive to Isx effects.

In addition to MEF2 proteins, another key transcription factor that is activated by $Ca^{2+}$-dependent signaling in neuronal cells is the nuclear CREB transcription factor, which remained unchanged between vehicle and Isx-treated cells, and served as normalization controls for nuclear extracts. GAPDH was used as a loading control for cytoplasmic extracts.

To visualize the subcellular distribution of HDAC5, NPCs were infected with an adenovirus expressing GFP-HDAC5 (AdGFP-HDAC5) and stimulated with vehicle or Isx for 1 day. In unstimulated cells, 80-90% of the cells contained GFP-HDAC5 in both nuclear and cytoplasmic compartments, reflecting a basal level of nuclear export consistent with what is observed in other cell types. In contrast, Isx triggered nuclear export of HDAC5 (60% cytoplasmic localization versus 35% both nuclear and cytoplasmic). Phosphorylation of serines 259 and 498 in HDAC5 creates docking sites for 14-3-3 chaperone proteins, which shuttle HDAC5 to the cytoplasm. Conversely, HDAC5 S259/498A (S-A mutant) was found mostly in the nuclear compartment regardless of Isx treatment. To further confirm the subcellular distribution of phospho-HDAC5, NPCs were co-infected with adenovirus expressing HDAC5-Flag and CMV-GFP (to monitor transgene expression in live cells). NPC lysates were immunoprecipitated with a Flag antibody and protein blotted with phospho-HDAC5 and Flag antibody. Indeed the majority of overexpressed Flag-HDAC5 was found in the cytoplasmic fraction after a 2-day Isx treatment, when probed with both the phospho-HDAC5 and Flag antibodies. Total lysates was also immunoblotted with CREB and GFP antibodies to verify the separation of nuclear and cytoplasmic fractions. Finally, to determine whether Isx treatment could induce hyperphosphorylation of HDAC5 in a different cell type, the inventors also found a significant increase in the percentage of Cos cells that exhibited cytoplasmic localization of HDAC5 after drug treatment (from 80.9% Nuc and 13.6% Cyto in vehicle-treated cells to 39.5% Nuc and 46.2% Cyto in Isx-treated cells).

The inventors next directly examined HDAC5 and MEF2 effects on an endogenous MEF2 target gene, NR1, since the inventors did observe an induction of NR1 mRNA with Isx treatment. Indeed an NR1 promoter luciferase construct that contains a functional MEF2-binding site (SEQ ID NO: 1 (TTATTTATTTAG, −805 to −796)) was induced with Isx treatment in a dose-dependent manner. Adenovirus over-expression of HDAC5 suppressed NR1-luciferase activity by at least two-fold compared to infection of a control GFP adenovirus (AdCMV-GFP), in both vehicle- and Isx-treated NPCs. The HDAC5 S-A mutant also suppressed NR1 activity in vehicle- and Isx-treated NPCs. Similar results were seen with an additional MEF2 reporter 3XMRE-luc. NPCs were infected with a control GFP adenovirus at equivalent titers to the HDAC5-GFP WT and S-A adenoviruses to confirm a transduction efficiency of nearly 80-90%. These data suggest Isx de-repression/activation of MEF2 in NPCs is associated with class II HDAC, such as HDAC5, transcriptional regulation of neuronal target genes.

To further confirm this, the inventors co-transfected NPCs with a construct encoding a repressor form of MEF2C in NPCs, where the repressor domain of engrailed is fused to MEF2C(CAG-MEF2C-ENG), there was significantly less activation of NR1-luciferase in vehicle-treated cultures compared to over-expression of a CAG-GFP control plasmid. More interestingly, this was sufficient to block Isx-activation of NR1-luciferase. In addition, the inventors measured the neuronal reporter gene NeuroD-luciferase. As with NR1-luciferase, there was significantly less NeuroD activity in both vehicle- and Isx-treated NPCs when HDAC5 (WT), HDAC5 (S-A), or the dominant repressor MEF2C-eng was over-expressed, compared to NPCs that expressed a control GFP plasmid. Taken together, these results suggest that the initial up-regulation of NR1 and NeuroD, and potentially other $Ca^{2+}$-activated neuronal genes after Isx treatment is coupled to MEF2 activation in NPCs.

Isx Triggered HDAC5 Export and Neuronal Differentiation is CamK-Dependent.

As mentioned previously, Class II HDACs are considered signal-responsive repressors during cardiac hypertrophy and nucleocytoplasmic shuttling of HDACs enables MEF2 to associate with HATs. Shuttling of class II HDACs is dependent on phosphorylation of two serine-containing motifs found at their N-termini, when phosphorylated, these motifs are associated with 14-3-3 that masks a nuclear localization sequence. The kinase(s) that phosphorylate class II HDACs and transmit various extracellular signals down to the genome have been mainly attributed to CaM kinases (CaMK) and protein kinase D (PKD), which is phosphorylated and activated by protein kinase C(PKC). To further define the signaling pathways leading to phosphorylation and nuclear export of HDAC5, the inventors tested inhibitors of CaMK and PKC for their abilities to block Isx-induced neuronal differentiation. A specific inhibitor of CaMK (KN93) was extremely effective in blocking Isx-mediated reporter gene expression (3XMRE- and NeuroD-luciferase). In contrast, G66976, a specific inhibitor of the $Ca^{2+}$-dependent PKC isozymes did not significantly affect Isx-induced reporter gene expression. Most importantly, KN93 blocked HDAC5 phosphorylation in Isx-treated NPCs, while G66976 did not. Autophosphorylation of CaMK is usually required for maximal activity and results in the formation of $Ca^{2+}$-independent enzymes that is usually associated with its ability to respond to different frequencies of $Ca^{2+}$ spikes, which is critical in neuronal cells for learning and memory processes.

Example 6

Figure 9:
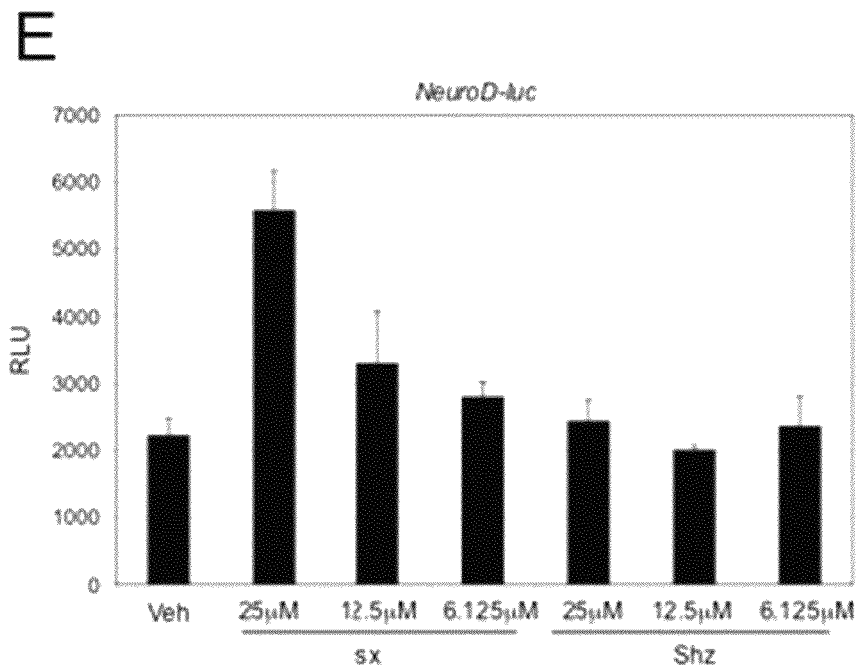
Figure 9:
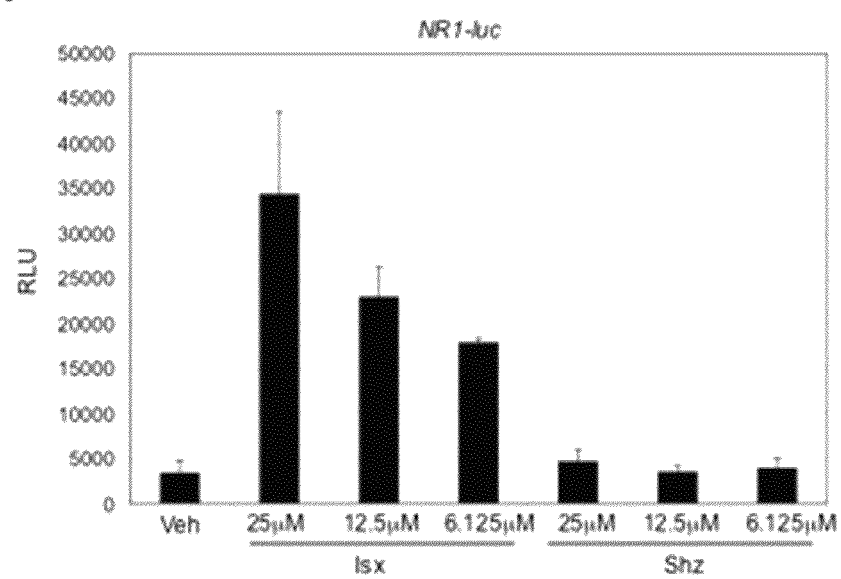
Figure 9:
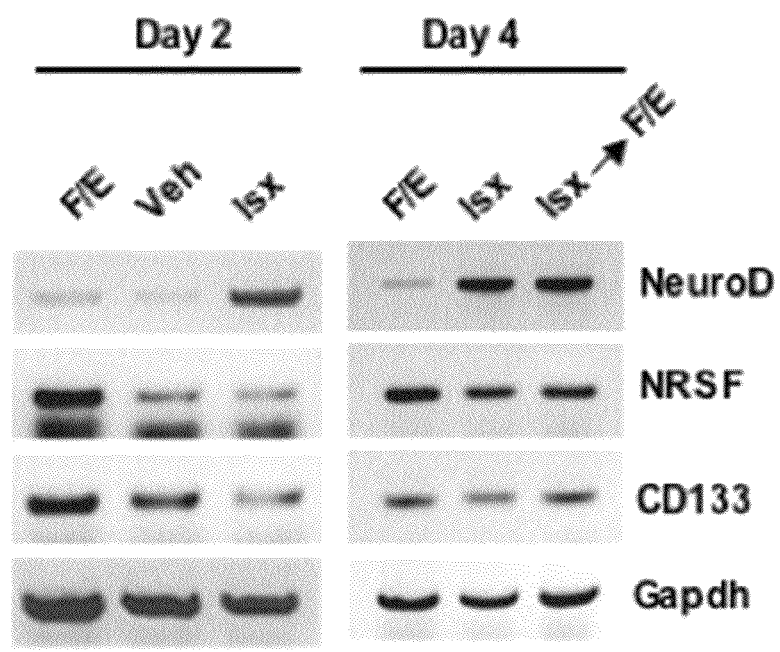
Figure 9:
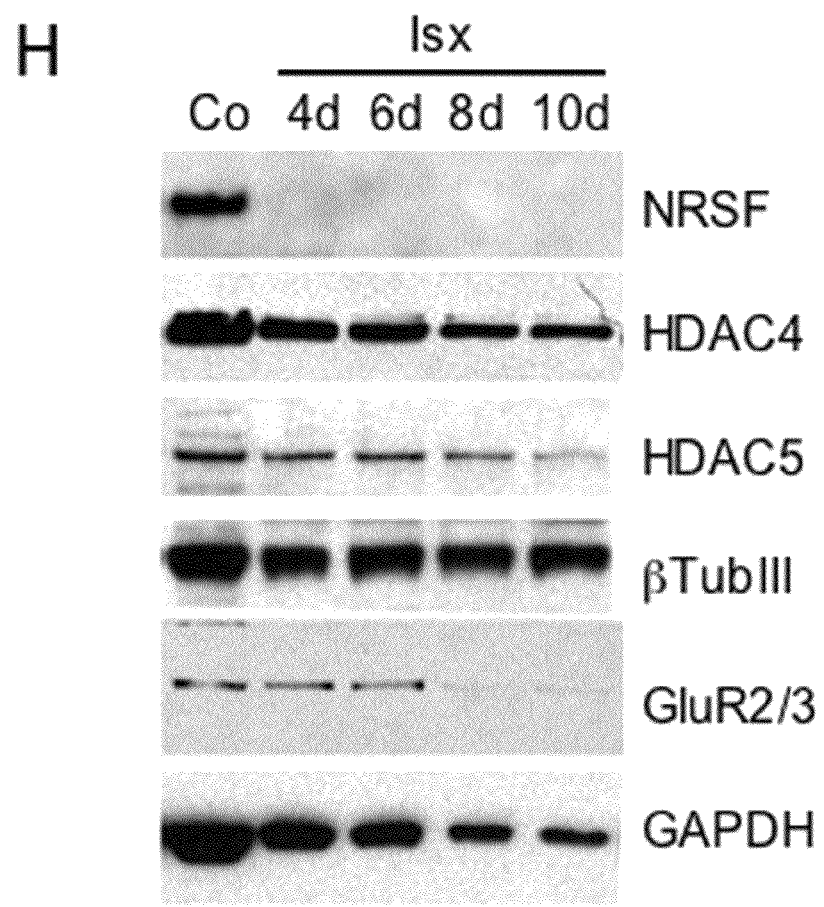

Isx-9 Treatment Induces Differentiation and Affects Neuron-Specific Gene and Protein Expression in Brain Tumor Stem Cells CD133+ glioblastoma brain tumor stem cells (BTSCs) from an explanted human tumor specimen were treated with 20 μM Isx-9 (FIG. 9C) or vol/vol DMSO (vehicle) control (FIG. 9B). FIG. 9D shows staining of the Isx-9-treated cells. Dose-dependent activation of two neuron-specific reporter genes, NeuroD- and NMDA receptor 1-luciferase was observed with Isx-9-treated BTSCs as opposed to vehicle control-treated cells (FIGS. 9E and 9F). The effect of 20 ng/mL FGF/EGF growth factors on BTSC differentiation is shown in FIG. 9A. A compound from an unrelated class of small molecules (sulfonyl hydrazone, Shz) did not significantly induce reporter gene activity (FIG. 9F).

Up-regulation of NeuroD was observed in BTSCs treated with Isx-9 for 2 days (FIG. 9G). This activity remained following addition of FGF/EGF without additional Isx-9 addition. The Kruppel-family zinc finger transcriptional regulator and proto-oncogene neuron-restrictive silencer factor (NRSF) (FIG. 9H) and CD133 are both downregulated with Isx-9-treatment.

Despite a dramatic change in cell morphology and attachment mediated by Isx-9 treatment, overall levels of neuronal proteins, such as 13TujIII and glutamate receptor 2 (GluR2) do not significantly differ between control and Isx-9-treated BTSCs (FIG. 9H).

Example 7

Isoxazoles Induce Growth Arrest and Inhibit the Tumorigenic Potential of Human BTSCs In Vitro and In Vivo CD133(+) brain tumor stem cells (BTSCs) from an explanted human tumor specimen were treated with EGF/FGF (FIG. 10A) or Isx-9 (20 μM) (FIG. 10B) for 7 days before returning to EGF/FGF (FIG. 10C) or EGF/FGF plus Isx-9 conditions (FIG. 10D) for an additional 2 days. FIGS. 10A-D demonstrate the growth inhibition effects of Isx-9 on these cells. A 7-day exposure to Isx-9 promotes an irreversible state of cell attachment and differentiation, even when challenged with growth factors.

The number and size of neurospheres observed in 7-day pretreated BTSCs with DMSO (vehicle), EGF/FGF, or Isx-9 that were dissociated and re-plated to faun secondary neurospheres (1000 cells/well) under various conditions is shown in FIG. 10F. Isx-9 pre-treatment mediates a decrease in the average number and size of each secondary neurosphere (an indicator of stem cell self-renewal activity) compared to EGF/FGF pre-treatment, even when growth factors are added back for an additional 7 days.

Isx-9 pre-treatment for 7 days leads to decreased DNA synthesis/proliferation (BrdU uptake with a 1 hour pulse prior to fixation) compared to EGF/FGF or vehicle pre-treatment, even when EGF/FGF is added back for 24 hours (FIGS. 10G-J).

Seven-day exposure of RFP-labeled human CD133(+) BTSCs to 20 ng/ml EGF/FGF (FIGS. 10K and 10L) or Isx-9 (20 μM) (FIGS. 11M and 11N) in vitro, before transplantation into the striatum of NOD/scid mice, dramatically reduces tumor-initiating ability. Isx-9 pre-treatment significant reduced the number of RFP-labeled BTSCs in the striatum after 1 month (n=3 mice/group, 30,000 cells injected/striatum). BTSC transplantation was performed by stereotactic surgery into the left striatum (coordinates from Bregma AP –0 mm, ML +2.5 mm, DV –3.5 mm) with a 33-gauge Hamilton syringe at a flow rate of 30,000 cells/10 minutes.

All of the methods and apparatuses disclosed and claimed herein can be made and executed without undue experimentation in light of the present disclosure. While the compositions and methods of this invention have been described in terms of preferred embodiments, it will be apparent to those of skill in the art that variations may be applied to the methods and apparatuses and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,826,364
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,284,412

U.S. Pat. No. 4,366,241
U.S. Pat. No. 4,411,990
U.S. Pat. No. 4,472,509
U.S. Pat. No. 4,498,766
U.S. Pat. No. 4,661,913
U.S. Pat. No. 4,680,338
U.S. Pat. No. 4,714,682
U.S. Pat. No. 4,767,206
U.S. Pat. No. 4,774,189
U.S. Pat. No. 4,857,451
U.S. Pat. No. 4,938,948
U.S. Pat. No. 4,989,977
U.S. Pat. No. 5,021,236
U.S. Pat. No. 5,141,648
U.S. Pat. No. 5,160,974
U.S. Pat. No. 5,196,066
U.S. Pat. No. 5,478,722
U.S. Pat. No. 5,563,250
U.S. Pat. No. 5,856,456
U.S. Pat. No. 5,880,270
U.S. Publ. Appl. No. 2005/0164382
U.S. Publ. Appl. No. 2005/0277162
Abeyta et al., *Hum. Mol. Genet.*, 13(6):601-608, 2004.
Al-Hajj et al., *Proc. Natl. Acad. Sci. USA*, 100:3983-3988, 2003.
Antibodies: A Laboratory Manual, Cold Spring Harbor Laboratory, 1988.
Atherton et al., *Biol. of Reproduction*, 32:155-171, 1985.
Berberian et al., *Science*, 261:1588-1591, 1993.
Bergsagel et al. *Cancer Res.*, 28:2187-2196, 1968.
Bonnet and Dick, *Nature Med.*, 3, 730-737, 1997.
Bruce et al., *Nature*, 199:79-80, 1963.
Bundgaard, *Drugs of the Future*, 16:443-458, 1991.
Bundgaard, In: *Design of Prodrugs*, 7-9; 21-24, Elsevier, Amsterdam, 1985.
Cicchi et al., In: *Progress in Heterocyclic Chemistry*, Elsevier, 2003.
Cleary et al., *Trends Microbiol.*, 4:131-136, 1994.
Cooper, In: *Elements Of Human Cancer*, Jones and Bartlett Publishers, ISBN: 0867201916, 1992.
Dholakia et al., *J. Biol. Chem.*, 264, 20638-20642, 1989.
Dontu et al., *Genes Dev.*, 17:1253-1270, 2003.
Gage et al., *Proc. Natl. Acad. Sci. USA*, 92:11879-11883, 1995.
Gage, *Science*, 287:1433-1438, 2000.
Greene and Wuts, In: *Protecting Groups in Organic Synthesis*, 3rd ed., John Wiley & Sons, Inc., 1999.
Grunanger and Vita-Finzi, In: *The Chemistry of Heterocyclic Compounds: Isoxazoles*, Wiley-Interscience, NY, 1991.
Gudjonsson et al., *Genes Dev.*, 16:693-706, 2002.
Habara-Ohkubo, A., *Cell Struct Funct.*, 21, 101-110, 1996.
Hamburger and Salmon, *Science*, 197: 461-463, 1977.
*Handbook of Pharmaceutical Salts: Properties, Selection and Use*, Stahl and Wermuth (Eds.), Verlag Helvetica Chimica Acta, 2002.
Hsieh et al., *J. Cell Biol.*, 164:111-122, 2004.
Hsieh et al., *Proc. Natl. Acad. Sci. USA* 101, 16659-16664, 2004.
Kang et al., *Science*, 240:1034-1036, 1988.
Khatoon et al., *Ann. of Neurology*, 26, 210-219, 1989.
King et al., *J. Biol. Chem.*, 269, 10210-10218, 1989.
Kohler et al., *Methods Enzymol.*, 178:3, 1989.
Kreier et al., In: *Infection, Resistance and Immunity*, Harper and Row, New York, 1991.
Lagasse et al. *Immunity*, 14:425-436, 2001.
Lenert et al., *Science*, 248:1639-1643, 1990.
O'Shannessy et al., *J. Immun. Meth.*, 99, 153-161, 1987.
Owens and Haley, *J. Biol. Chem.*, 259:14843-14848, 1987.
Palmer et al., *Mol. Cell. Neurosci.*, 8:389-404, 1997.
Palmer et al., *Nature*, 411(6833):42-43, 2001.
Park et al., *J. Nat. Cancer Inst.*, 46:411-422, 1971.
Perez-Losada and Balmain, *Nat. Rev. Cancer*, 3:434-443, 2003.
Potter and Haley, *Meth. in Enzymol.*, 91, 613-633, 1983.
Ramalho-Santos et al., *Science*, 298:597-600, 2002.
Ray and Gage, *Mol. Cell. Neurosci.*, 31(3):560-573, 2006.
Reya et al., *Nature*, 414:105-111, 2001.
Sasso et al., *J. Immunol.*, 142:2778-2783, 1989.
Shorki et al., *J. Immunol.*, 146:936-940, 1991.
Silvermann et al., *J. Clin. Invest.*, 96:417-426, 1995.
Tumbar et al., *Science*, 303(5656):359-363, 2004.
Welm et al., *Develop. Biology*, 245:42-56, 2002.
Wodinsky et al., *Cancer Chemother. Rep.*, 51:415-421, 1967.
Zepeda et al., *Somat. Cell Mol. Genet.*, 21:61-73, 1999.
Zhang et al., *J. Biomol. Screen*, 4:67-73, 1999.

What is claimed is:

1. A method of inducing Mef2 expression in a stem cell comprising contacting said stem cell with a compound of formula (II):

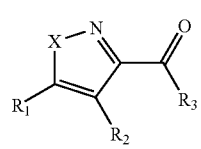

wherein:
R₁ is substituted or unsubstituted thiophenyl or a substituent of formula (A):

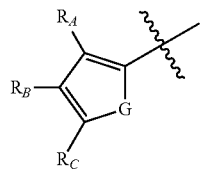

(A)

wherein:
$R_A$, $R_B$ and $R_C$ are each independently selected from the group consisting of hydrogen, halogen, alkyl, aralkyl, aryl, cyano, or nitro, and a heteroatom unsubstituted $C_1$-$C_{10}$ acyl; and
G is O, —NH, or S;
$R_2$ is hydrogen, hydroxy, halogen, nitro, aryl, alkyl, alkoxy, alkenyl, alkenyloxy, alkynyl, alkynyloxy, aralkyl, —CHO, —C(O)$R_9$, —OC(O)$R_9$, —OC(O)O$R_9$, —O(CN)O$R_9$, —C(O)N$R_9R_{10}$, —OC(O)N$R_9R_{10}$, —N$R_9$O$R_5$, or —SO₃$R_9$; wherein
$R_9$ and $R_{10}$ are each independently hydrogen, alkyl, aryl, or aralkyl;
$R_3$ is —NH—O-alkyl, —NH—OH, —OR₁₁ or —NR₁₁R₁₂, wherein
$R_{11}$ and $R_{12}$ are each independently hydrogen, alkyl, alkenyl, alkynyl, aryl, or aralkyl; or
$R_{11}$ is H and $R_{12}$ is a cyclic group; or
$R_{11}$ and $R_{12}$ together with the nitrogen to which they are bound form a cyclic group;
X is O or —NR₁₃, wherein $R_{13}$ is hydrogen, alkyl, aryl, or aralkyl;
or a stereoisomer, solvate, hydrate, or pharmaceutically acceptable salt thereof.

2. The method of claim 1, wherein any alkyl group comprised in any of $R_2$, $R_9$, $R_{10}$, $R_{11}$, $R_{12}$, or $R_{13}$ is lower alkyl.

3. The method of claim 2, wherein $R_{11}$ is H and the $R_{12}$ cyclic group is cyclopropyl, cyclobutyl, or cyclopentyl.

4. The method of claim 1, wherein the compound of formula (II) is further defined as a compound of formula (III):

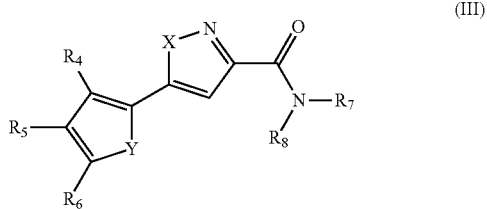

(III)

wherein:
$R_7$ and $R_8$ are both hydrogen; or
$R_7$ is hydrogen and $R_8$ is selected from the group consisting of unsubstituted or heteroatom-substituted $C_1$-$C_6$ alkyl, $C_3$-$C_6$ cycloalkyl, $C_2$-$C_6$ alkenyl, $C_2$-$C_6$ alkynyl and benzyl; or
$R_7$ and $R_8$ may be joined together to form a ring selected from azetidinyl, pyrrolidinyl, piperidinyl, piperazinyl and morpholinyl;
$R_4$, $R_5$ and $R_6$ are independently selected from the group consisting of hydrogen, halogen, $C_1$-$C_6$ alkyl, $C_3$-$C_6$ cycloalkyl, unsubstituted or heteroatom-substituted aromatic or heteroaromatic ring, cyano, nitro, and a heteroatom unsubstituted $C_1$-$C_{10}$ acyl;
X is O or NH; and
Y is O, NH, or S,
or a stereoisomer, solvate, hydrate, or pharmaceutically acceptable salt thereof.

5. The method of claim 4, wherein Y is S and $R_8$ is a unsubstituted or heteroatom-substituted $C_1$-$C_6$ alkyl.

6. The method of claim 4, wherein Y is S and $R_8$ is a unsubstituted or heteroatom-substituted $C_3$-$C_6$ cycloalkyl.

7. The method of claim 4, wherein Y is O and $R_8$ is a unsubstituted or heteroatom-substituted $C_3$-$C_6$ cycloalkyl.

8. The method of claim 4, wherein Y is O and $R_8$ is a unsubstituted or heteroatom-substituted $C_1$-$C_6$ alkyl.

9. The method of claim 4, wherein Y is S and $R_8$ is a unsubstituted or heteroatom-substituted $C_2$-$C_6$ alkenyl, $C_2$-$C_6$ alkynyl or benzyl.

10. The method of claim 4, wherein Y is O and $R_8$ is a unsubstituted or heteroatom-substituted $C_2$-$C_6$ alkenyl, $C_2$-$C_6$ alkynyl or benzyl.

11. The method of claim 4, wherein $R_7$ is H.

12. The method of claim 4, wherein said stem cell is located in an animal subject.

13. The method of claim 4, wherein said stem cell is contacted ex vivo.

14. The method of claim 1, wherein alkyl is $C_1$-$C_6$ alkyl or $C_3$-$C_6$ cycloalkyl.

15. A method of inducing Mef2 expression in a stem cell comprising contacting said stem cell with a compound of formula (IV):

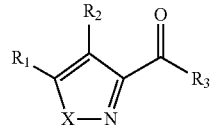

(IV)

wherein:
$R_1$ is selected from $C_{1-6}$alkyl and a 5- or 6-membered ring containing atoms independently selected from the group consisting of C, N, O and S,
wherein $R_1$ is optionally substituted with one or more substituents selected from the group consisting of hydroxy, halo, nitro, aryl, heteroaryl, $C_{1-6}$alkylhalo, $OC_{1-6}$alkylhalo, $OC_{1-6}$alkyl, $C_{2-6}$ alkenyl, $OC_{2-6}$alkenyl, $C_{2-6}$alkynyl, $OC_{2-6}$alkynyl, $C_{0-6}$alkyl$C_{3-6}$cycloalkyl, $OC_{0-6}$alkyl$C_{3-6}$cycloalkyl, $C_{1-6}$alkylaryl, $OC_{0-6}$alkylaryl, CHO, (CO)$R^4$, O(CO)$R^4$, O(CO)OR$^4$, O(CN)OR$^4$, $C_{1-6}$alkylOR$^4$, $OC_{2-6}$ alkylOR$^4$, $C_{1-6}$alkyl(CO)R$^4$, $OC_{1-6}$alkyl(CO)R$^4$, $C_{0-6}$alkylCO$_2$R$^4$, $OC_{1-6}$alkylCO$_2$R$^4$, $C_{0-6}$alkylcyano, $OC_{2-6}$alkylcyano, $C_{0-6}$alkylNR$^4$R$^5$, $OC_{2-6}$alkylNR$^4$R$^5$, $C_{1-6}$alkyl(CO)NR$^4$R$^5$, $OC_{1-6}$alkyl(CO)NR$^4$R$^5$, $C_{0-6}$ alkylNR$^4$(CO)R$^5$, $OC_{2-6}$alkylNR$^4$(CO)R$^5$, $C_{0-6}$alkylNR$^4$(CO)NR$^4$R$^5$, $C_{0-6}$ alkylSR$^4$, $OC_{2-6}$alkylSR$^4$, $C_{0-6}$alkyl(SO)R$^4$, $OC_{2-6}$alkyl(SO)R$^4$, $C_{0-6}$ alkylSO$_2$R$^4$, $OC_{2-6}$alkylSO$_2$R$^4$, $C_{0-6}$alkyl(SO$_2$)NR$^4$R$^5$, $OC_{1-6}$ alkyl(SO$_2$)NR$^4$R$^5$, $C_{0-6}$alkylNR$^4$(SO$_2$)R$^5$, $OC_{2-6}$alkylNR$^4$(SO$_2$)R$^5$, $C_{0-6}$alkylNR$^4$(SO$_2$)NR$^4$R$^5$, $OC_{2-6}$alkylNR$^4$(SO$_2$)NR$^4$R$^5$, (CO)NR$^4$R$^5$, O(CO)NR$^4$R$^5$, NR$^4$OR$^5$, $C_{0-6}$alkylNR$^4$(CO)OR$^5$, $OC_{2-6}$ alkylNR$^4$(CO)OR$^5$ and SO$_3$R$^4$;

$R_2$ is selected from the group consisting of hydrogen, hydroxy, halo, nitro, aryl, heteroaryl, $C_{1-6}$alkylhalo, $OC_{1-6}$alkylhalo, $C_{1-6}$alkyl, $OC_{1-6}$alkyl, $C_{2-6}$ alkenyl, $OC_{2-6}$alkenyl, $C_{2-6}$alkynyl, $OC_{2-6}$alkynyl, $C_{0-6}$alkyl$C_{3-6}$ cycloalkyl, $OC_{0-6}$alkyl$C_{3-6}$cycloalkyl, $C_{1-6}$alkylaryl, $OC_{0-6}$alkylaryl, CHO, $(CO)R^4$, $O(CO)R^4$, $O(CO)OR^4$, $O(CN)OR^4$, $C_{1-6}$alkylOR$^4$, $OC_{2-6}$alkylOR$^4$, $C_{1-6}$alkyl$(CO)R^4$, $OC_{1-6}$alkyl$(CO)R^4$, $C_{0-6}$alkylCO$_2R^4$, $OC_{1-6}$alkylCO$_2R^4$, $C_{0-6}$alkylcyano, $OC_{2-6}$alkylcyano, $C_{0-6}$alkylNR$^4R^5$, $OC_{2-6}$alkylNR$^4R^5$, $C_{1-6}$alkyl(CO)NR$^4R^5$, $OC_{1-6}$alkyl(CO)NR$^4R^5$, $C_{0-6}$ alkylNR$^4$(CO)R$^5$, $OC_{2-6}$alkylNR$^4$(CO)R$^5$, $C_{0-6}$alkylNR$^4$(CO)NR$^4R^5$, $C_{0-6}$ alkylSR$^4$, $OC_{2-6}$alkylSR$^4$, $C_{0-6}$alkyl(SO)R$^4$, $OC_{2-6}$alkyl(SO)R$^4$, $C_{0-6}$ alkylSO$_2R^4$, $OC_{2-6}$alkylSO$_2R^4$, $C_{0-6}$alkyl(SO$_2$)NR$^4R^5$, $OC_{2-6}$ alkyl(SO$_2$)NR$^4R^5$, $C_{0-6}$alkylNR$^4$(SO$_2$)R$^5$, $OC_{2-6}$ alkylNR$^4$(SO$_2$)R$^5$, $C_{0-6}$alkylNR$^4$(SO$_2$)NR$^4R^5$, $OC_{2-6}$ alkylNR$^4$(SO$_2$)NR$^4R^5$, (CO)NR$^4R^5$, O(CO)NR$^4R^5$, NR$^4$OR$^5$, $C_{0-6}$alkylNR$^4$(CO)OR$^5$, $OC_{2-6}$alkylNR$^4$(CO)OR$^5$ and $SO_3R_4$;

$R_3$ is selected from the group consisting of OR$^4$, NR$^4R^5$, and NR$^7R^8$, wherein R$^7$ and R$^8$, together with the nitrogen atom to which they are bound, combine to form a 5- to 6-member ring optionally containing one or more of S, O, and NH;

$R^4$ and $R^5$ are independently selected from the group consisting of hydrogen, $C_{1-6}$alkyl, $C_{1-6}$alkylaryl, $C_{1-6}$alkylheteroaryl, $C_{3-7}$cycloalkyl and aryl; and X is O or NR$^6$, wherein R$^6$ is selected from the group consisting of hydrogen, $C_{1-6}$alkyl, $C_{1-6}$alkylaryl, $C_{1-6}$alkylheteroaryl, $C_{3-7}$cycloalkyl and aryl;

or a stereoisomer, solvate, hydrate, or pharmaceutically acceptable salt thereof.

\* \* \* \* \*